US012680102B2

(12) United States Patent
Zakharenko et al.

(10) Patent No.: US 12,680,102 B2
(45) Date of Patent: Jul. 14, 2026

(54) miRNAS FOR REDUCING VENTRICLE ENLARGEMENT

(71) Applicant: St. Jude Children's Research Hospital, Inc., Memphis, TN (US)

(72) Inventors: Stanislav S. Zakharenko, Collierville, TN (US); Tae-Yeon Eom, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1209 days.

(21) Appl. No.: 17/629,211

(22) PCT Filed: Jul. 23, 2020

(86) PCT No.: PCT/US2020/043208
§ 371 (c)(1),
(2) Date: Jan. 21, 2022

(87) PCT Pub. No.: WO2021/016425
PCT Pub. Date: Jan. 28, 2021

(65) Prior Publication Data
US 2022/0290159 A1     Sep. 15, 2022

Related U.S. Application Data

(60) Provisional application No. 62/878,267, filed on Jul. 24, 2019.

(51) Int. Cl.
| | |
|---|---|
| *C07H 21/02* | (2006.01) |
| *A61K 9/00* | (2006.01) |
| *A61K 31/7088* | (2006.01) |
| *A61K 45/06* | (2006.01) |
| *A61P 25/00* | (2006.01) |
| *C07H 21/04* | (2006.01) |
| *C12N 15/113* | (2010.01) |

(52) U.S. Cl.
CPC ........ *C12N 15/1138* (2013.01); *A61K 9/0085* (2013.01); *A61K 31/7088* (2013.01); *A61K 45/06* (2013.01); *A61P 25/00* (2018.01); *C12N 2310/141* (2013.01); *C12N 2320/30* (2013.01)

(58) Field of Classification Search
CPC ...................... C12N 2310/141; C12N 15/113
See application file for complete search history.

(56) References Cited

PUBLICATIONS

Bourne, James A., Sch 23390: The First Selective Dopamine D-Like Receptor Antagonist, CNS Drug Reviews, vol. 7, No. 4, pp. 399-414, 2001 Neva Press, Branford, Connecticut.
Lewis, M M, et al., Asymmetrical lateral ventricular enlargement in Parkinson's disease, Eur J Neurol. Apr. 2009; 16 (4):475-81.doi: 10.1111/j.1468-1331.2008.02430.x.
Li, Jingyuan, et al., MicroRNA expression profile and functional analysis reveal that miR-382 is a critical novel gene of alcohol addiction, EMBO Mol Med (2013) 5, 1402-1414.doi 10.1002/emmm.201201900.
Tomé, M., et al., Presence of D1- and D2-like dopamine receptors in the rat, mouse and bovine multiciliated ependyma, J Neural Transm (2007) 114:983-994. doi 10.1007/s00702-007-0666-z.
International Search Report and Written Opinion mailed Jan. 6, 2021 for International Patent Application No. PCT/ US2020/ 043208, which was filed Jul. 23, 2020 and published as WO 2021/016425 on Jan. 28, 2021 (Applicant: St. Jude Children's Research Hospital, Inc. // Inventor: Zakharenko, et al.) (17 pages).

*Primary Examiner* — Amy Rose Hudson
(74) *Attorney, Agent, or Firm* — Troutman Pepper Locke LLP

(57) ABSTRACT

The invention is directed to methods and compositions for treating a disease associated with ventricular enlargement such as 22q11 deletion syndrome (22q11 DS) and schizophrenia (SCZ) by replenishment of decreased levels of miR-382-3p and/or miR-674-3p or inhibition of dopamine receptor Drd1 in ependymal cells.

17 Claims, 35 Drawing Sheets

Specification includes a Sequence Listing.

Fig. 2C
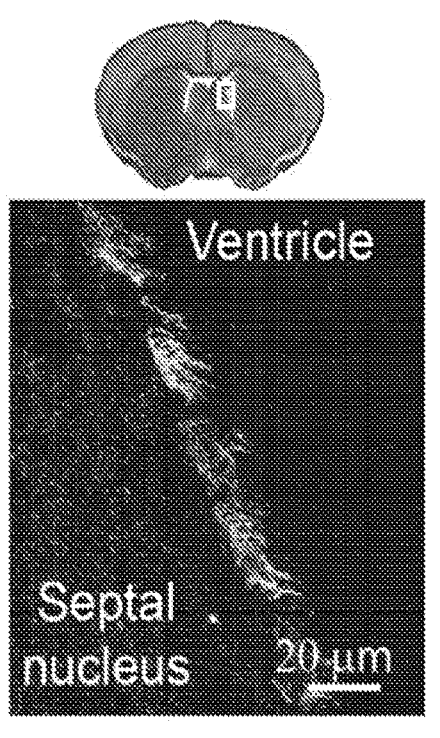
Fig. 2D
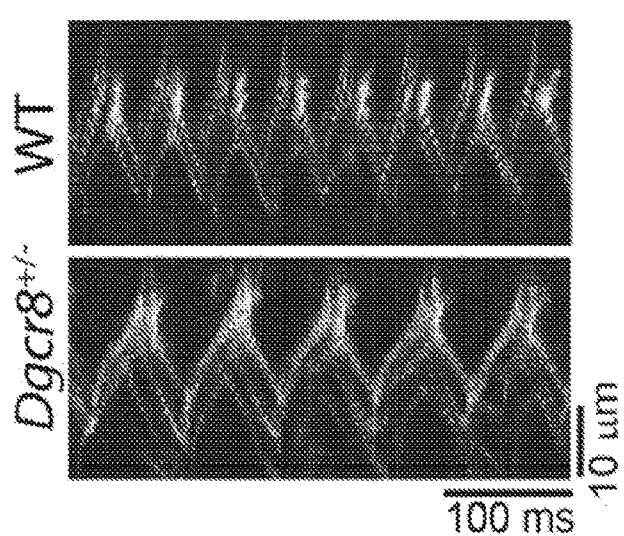
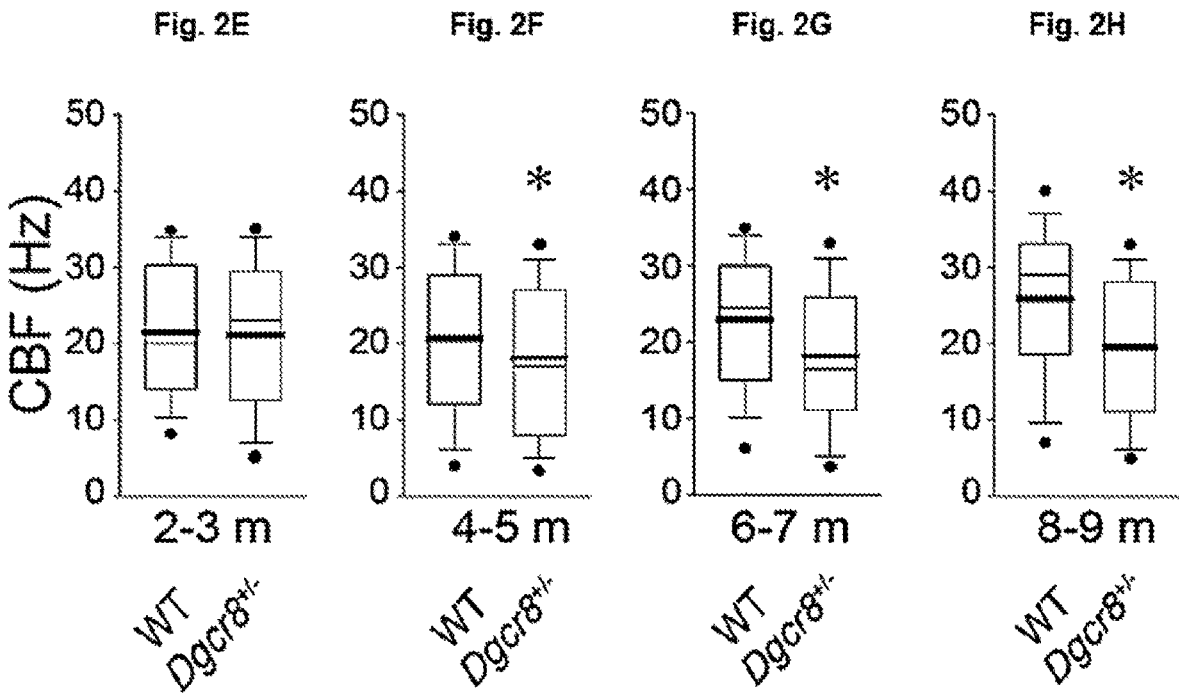
Fig. 2E  Fig. 2F  Fig. 2G  Fig. 2H

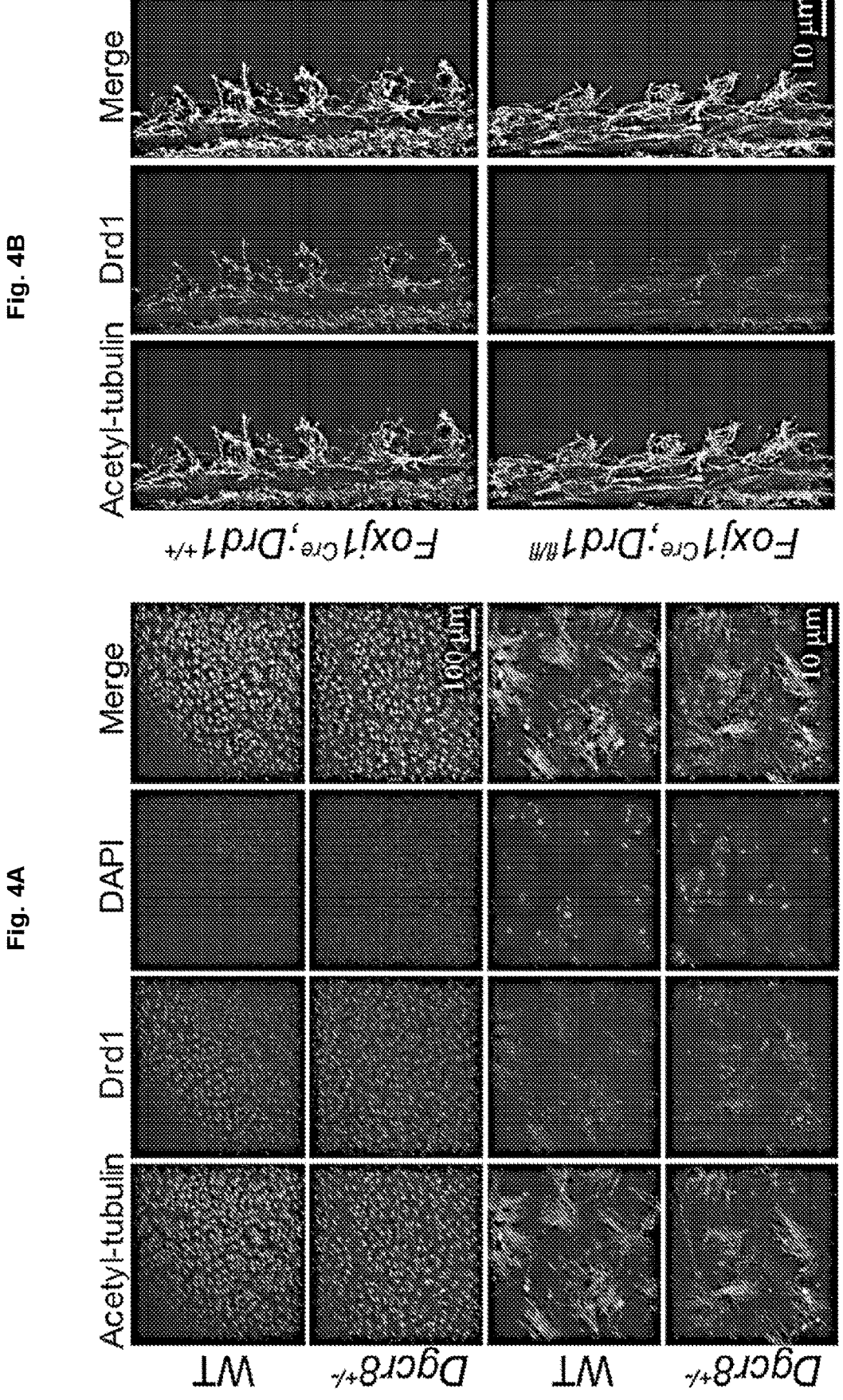

Fig. 5F            Fig. 5G

Fig. 6A
AAV1:miRNA-GFP → *Foxj1^Cre^;Ai14*
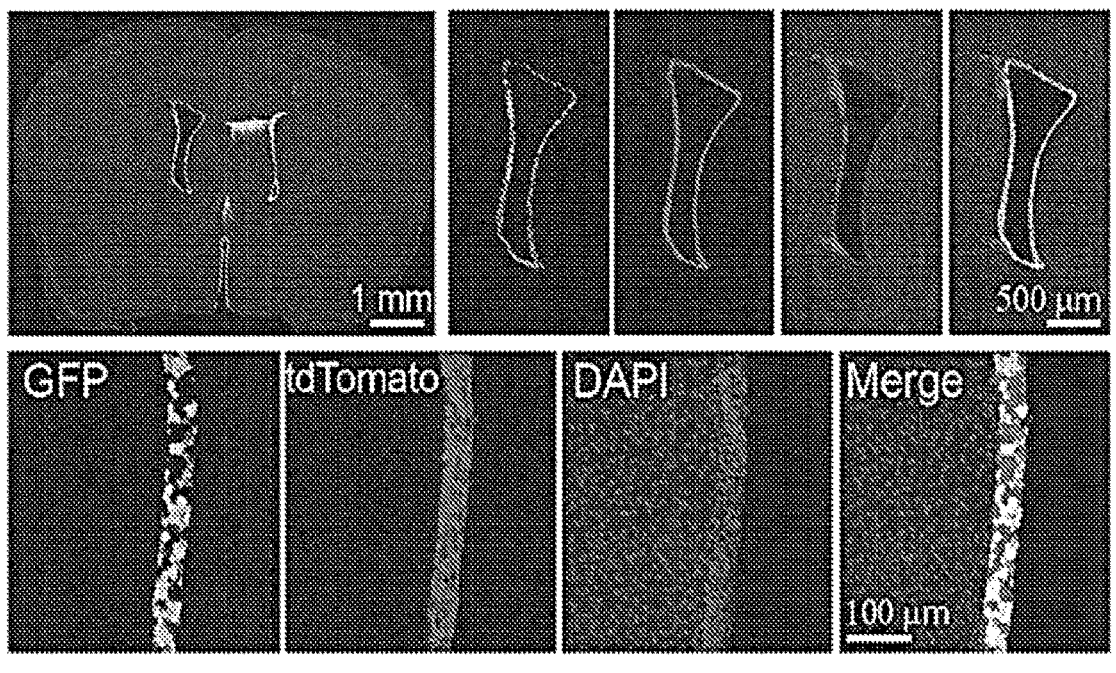
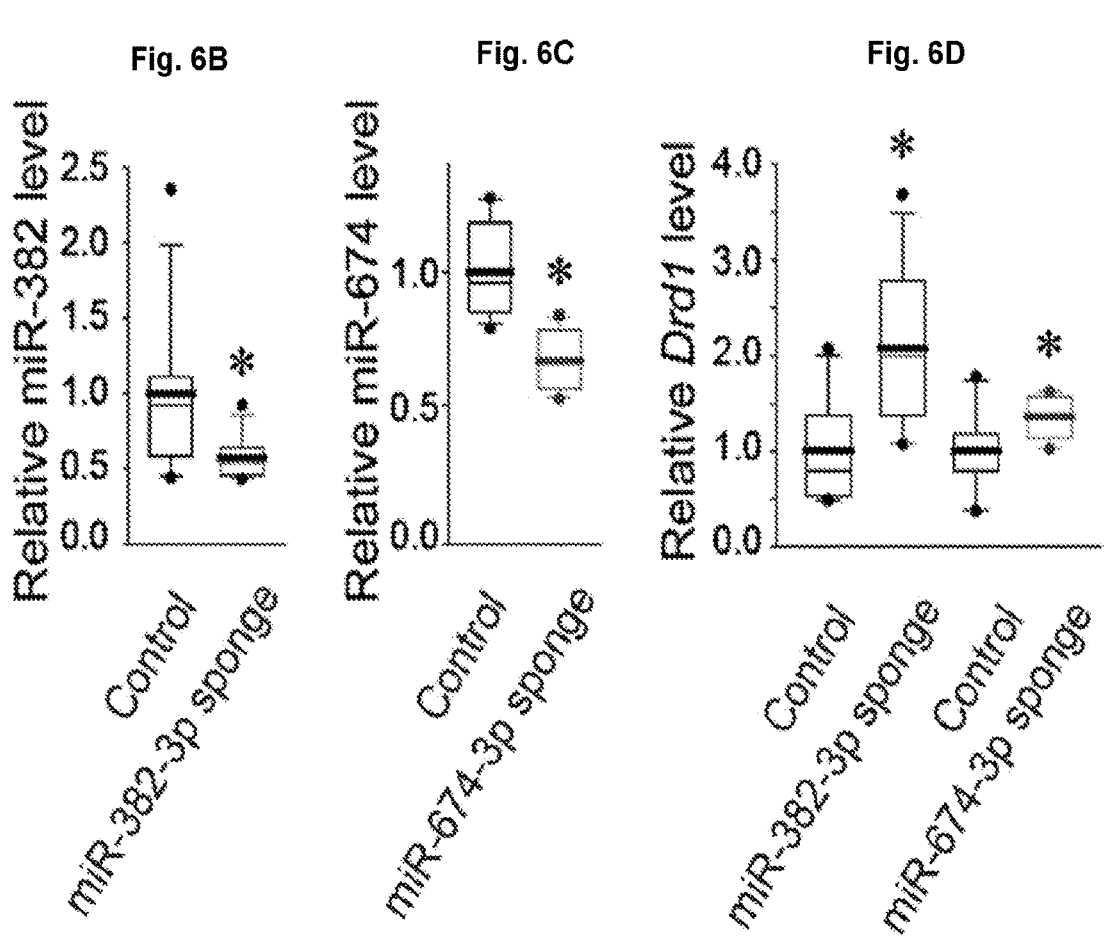
Fig. 6B Fig. 6C Fig. 6D Control    miR-382-3p sponge    miR-674-3p sponge Rostral Caudal

Fig. 8A
Fig. 8B
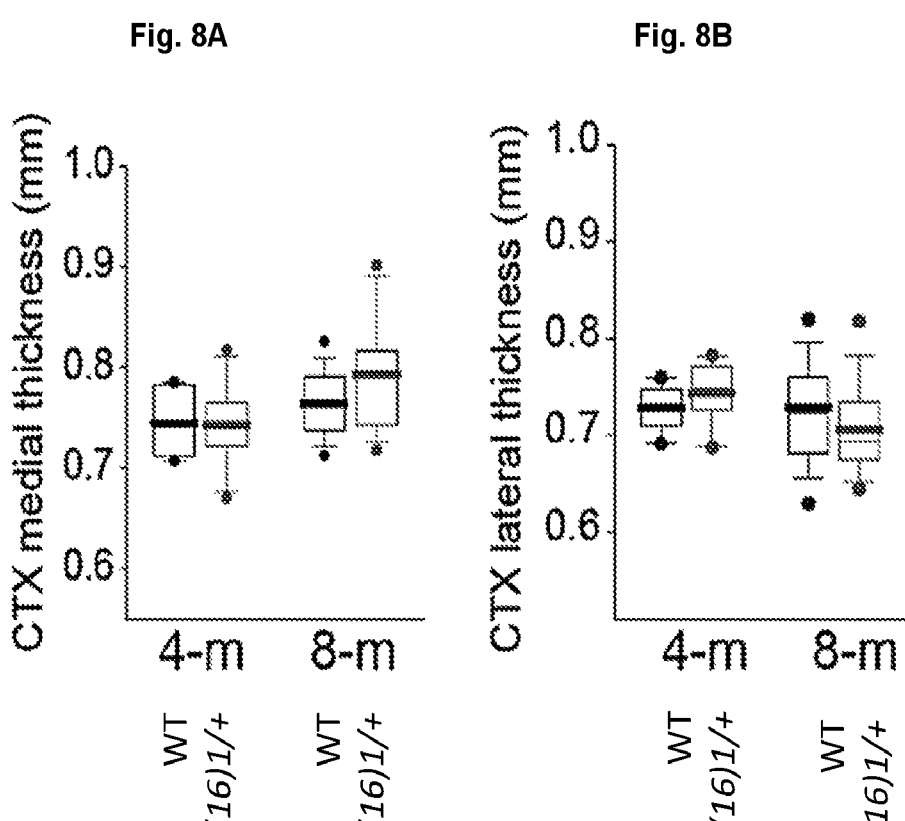
Fig. 8C
Fig. 8D
Fig. 8E
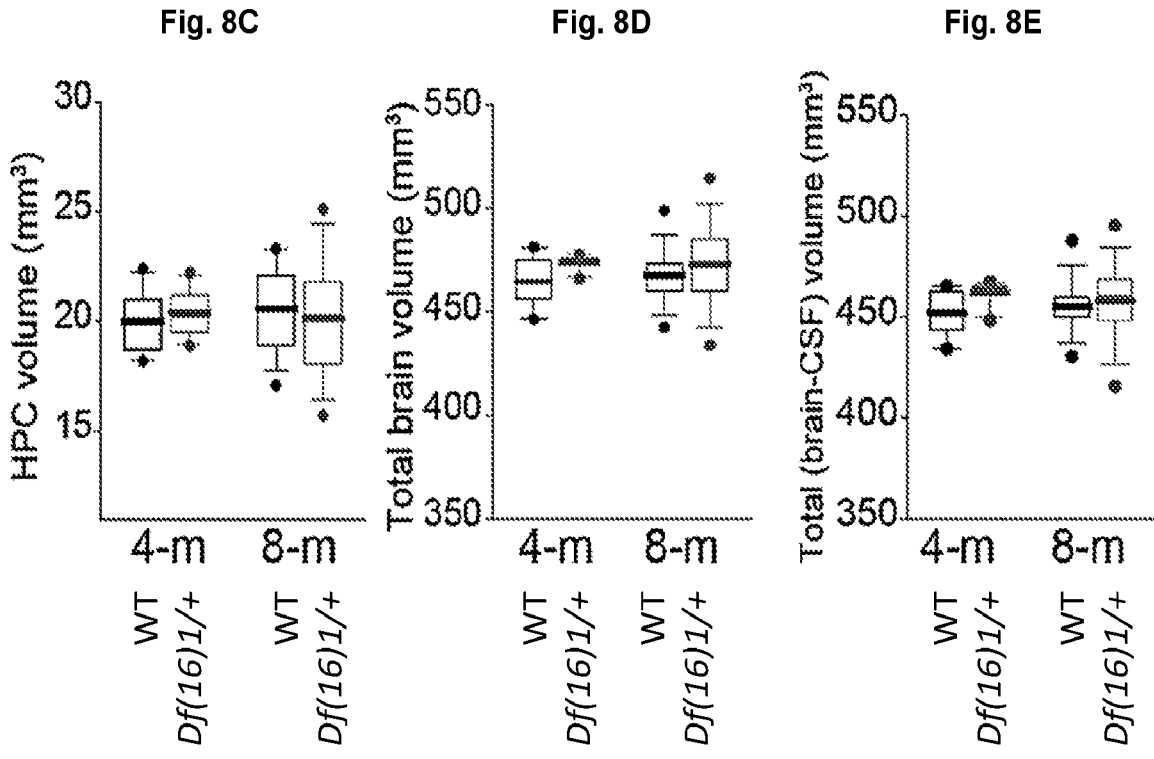

Fig. 8F
Fig. 8G
Fig. 8H
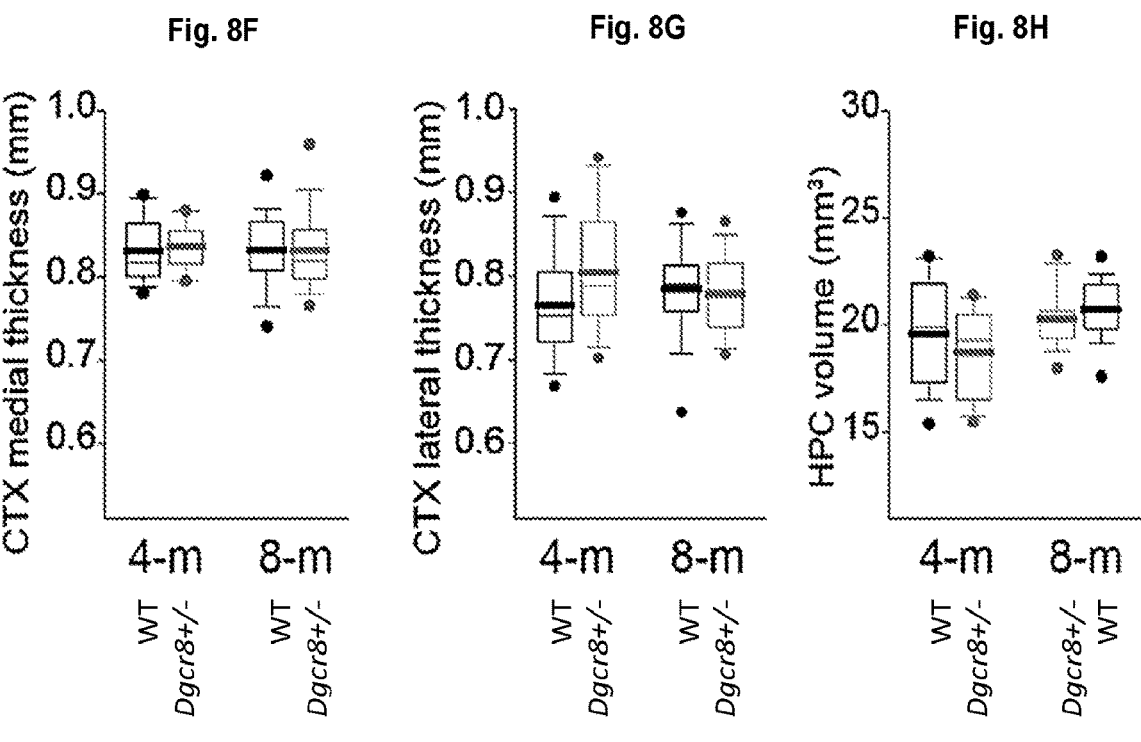
Fig. 8I
Fig. 8J
Fig. 8K
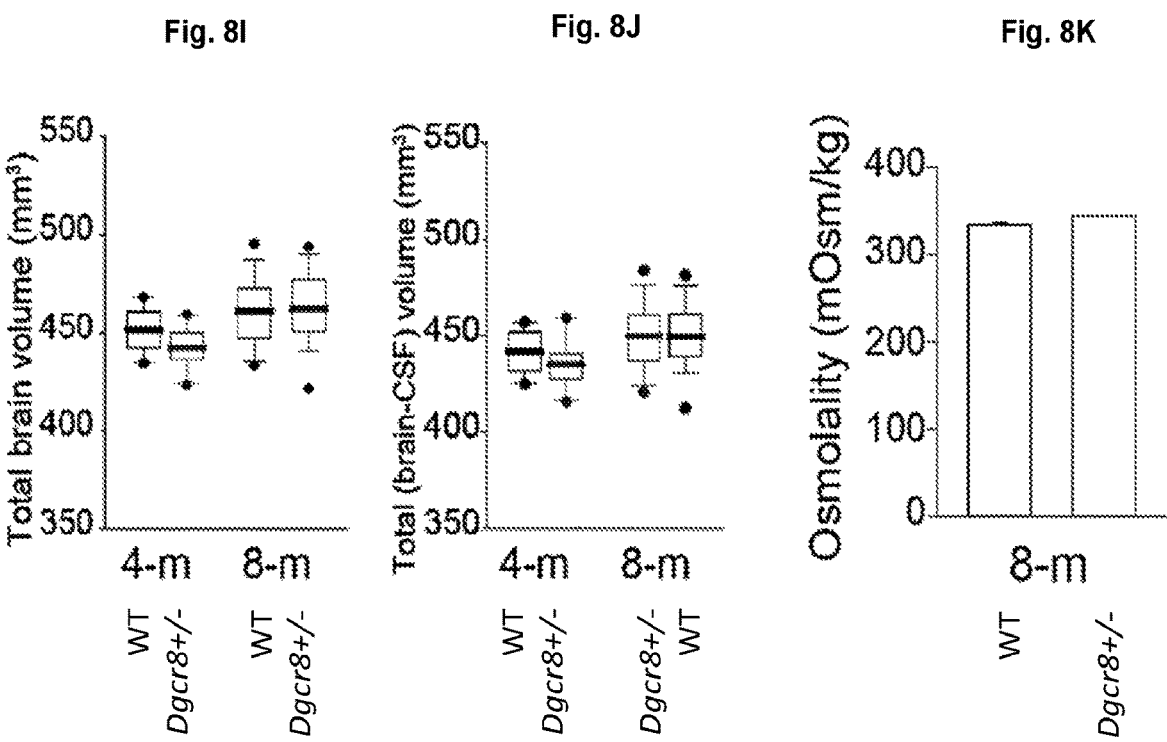

Fig. 9B                                    Fig. 9C

Fig. 10H
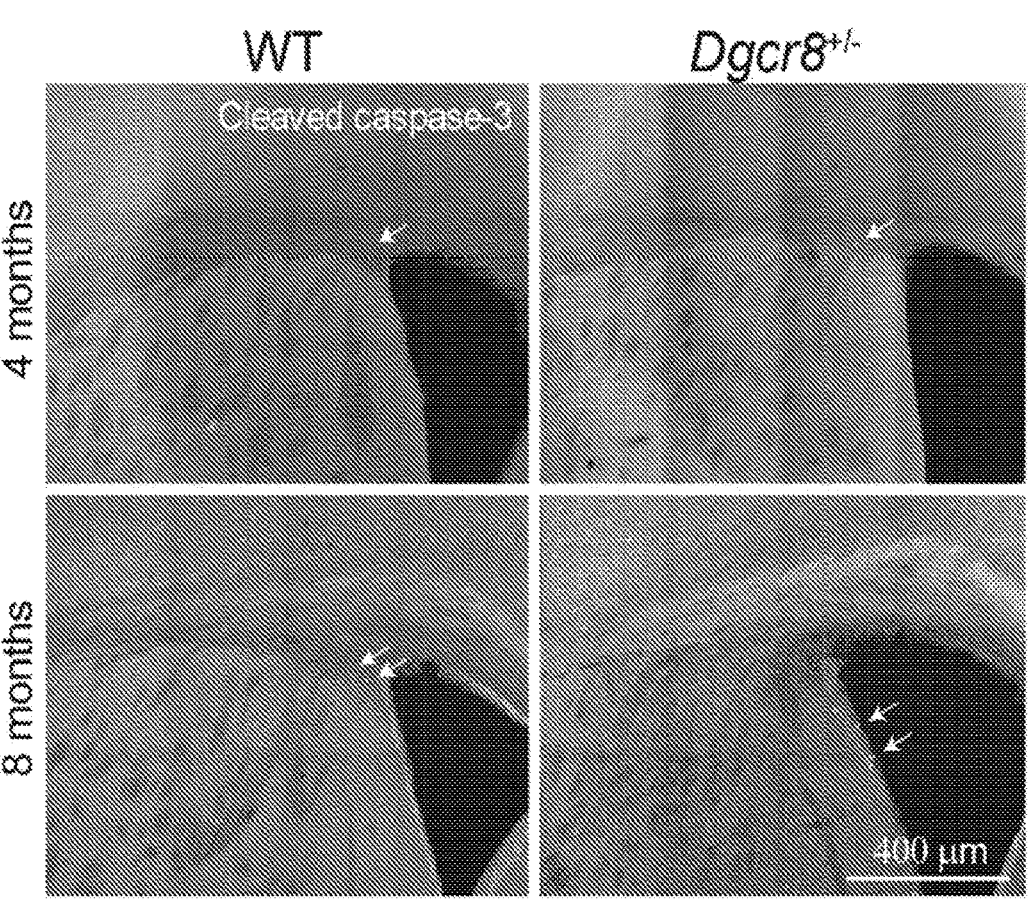
Fig. 10I
Fig. 10J
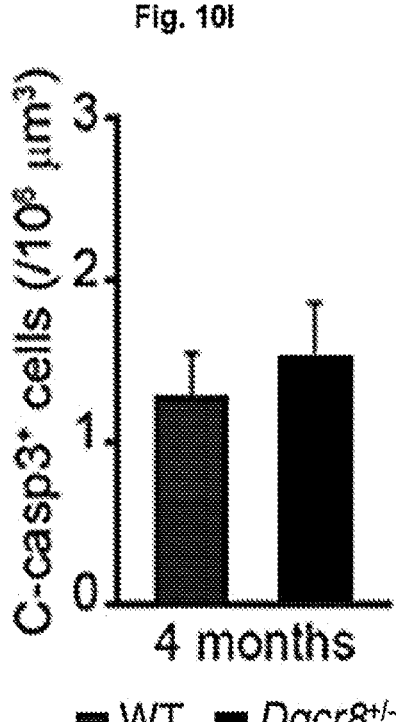
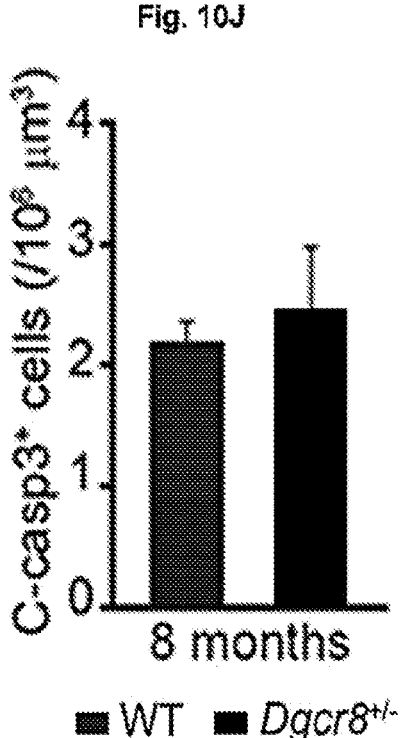

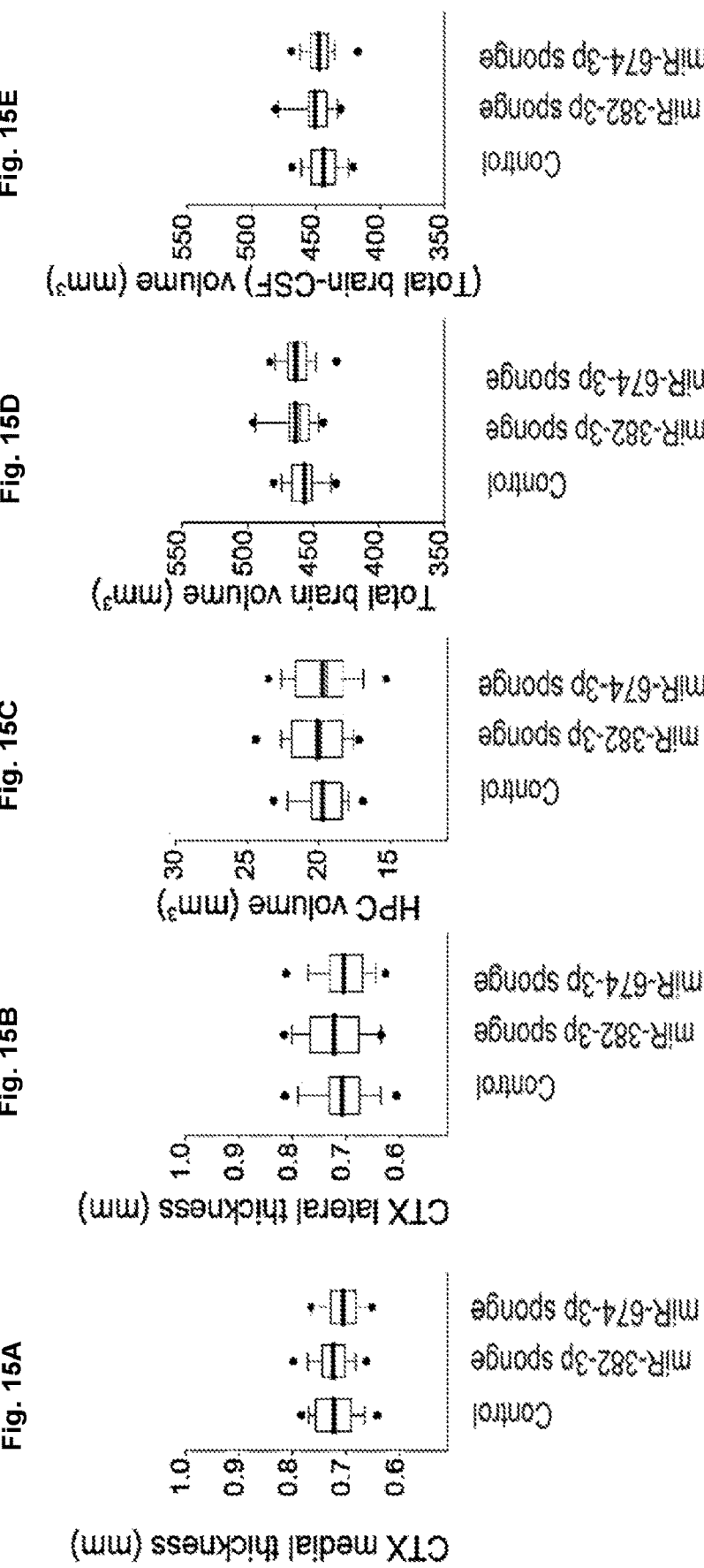

β-catenin γ-tubulin

1 miRNAS FOR REDUCING VENTRICLE ENLARGEMENT

CROSS-REFERENCE TO RELATED APPLICATIONS

This application is a National Stage Application of International Application No. PCT/US2020/043208, filed Jul. 23, 2020 which claims priority to U.S. Provisional Application No. 62/878,267, filed Jul. 24, 2019, all of which are herein incorporated by reference in their entireties.

STATEMENT AS TO FEDERALLY SPONSORED RESEARCH

This invention was made with government support under grant number MH097742 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 21, 2020, is named 243734_000138_SL.txt and is 10,606 bytes in size.

FIELD OF THE INVENTION

The invention is directed to a method for treating a disease associated with ventricular enlargement (e.g., schizophrenia and/or 22q11.2 deletion syndrome) by replenishment of decreased levels of miR-382-3p and/or miR-674-3p or inhibition of dopamine receptor Drd1 in ependymal cells.

BACKGROUND OF THE INVENTION

Progressive ventricular enlargement, the most frequently observed neuroanatomical abnormality in schizophrenia, is mediated by unknown mechanisms. The diagnosis of neurodevelopmental diseases such as schizophrenia (SCZ) is challenging due to the lack of robust and replicable neuroanatomical features. One of the most common and replicable findings in individuals with SCZ is enlarged brain ventricles (or ventriculomegaly) (van Erp et al., 2014, 2016; Franke et al., 2016; Honea et al., 2005; Johnstone et al., 1976; Kempton et al., 2008, 2010; Lawrie and Abukmeil, 1998; Narr et al., 2004; Olabi et al., 2011; Shenton et al., 2001; Styner et al., 2005; Vita et al., 2006; Wright et al., 2000). The progressive increase in the total or regional ventricular volumes usually becomes evident at the first episode of disease (Steen et al., 2006; Vita et al., 2006). Although not specific to SCZ, ventriculomegaly is consistently and frequently observed in schizophrenic patients (more than 80% of SCZ studies) (Shenton et al., 2001). Despite this strong linkage, the cause of ventricular enlargement in SCZ is unknown. Therefore, identifying the underlying mechanisms of this neuroanatomical feature may provide important insight into the pathogenesis of the disease.

SCZ is a polygenic disease that is difficult to reproduce in animal models. Substantial progress has been made in studying SCZ pathologies by modelling well-defined genomic lesions that increase the risk of the disease. For instance, 22q11.2 deletion syndrome (22q11DS) is a genetic disorder that increases the risk of SCZ approximately 30 fold (Bassett and Chow, 1999; Gothelf et al., 1999; Green et al., 2009; Murphy, 2002; Murphy et al., 1999; Pulver et al., 1994; Shprintzen et al., 1992). The 22q11DS is caused by a hemizygous 1.5- to 3-megabase (Mb) microdeletion on chromosome 22. Symptoms are indistinguishable between SCZ patients who have the 22q11.2 deletion and those who do not (Chow et al., 2006; Murphy et al., 1999; Pulver et al., 1994), suggesting the existence of a common pathogenic mechanism between 22q11DS and SCZ. The 1.5-Mb deletion is thought to be the minimal region containing the genes that account for the increased risk of SCZ among individuals with 22q11DS (Karayiorgou et al., 2010). Ventricular enlargement is a common neuroanatomical finding in individuals who have a chromosomal microdeletion, especially those with SCZ. The most frequent changes are seen in the lateral ventricles (LVs) and third ventricle (TV) (Chow et al., 1999, 2002; Eliez et al., 2000; Kempton et al., 2010; Shenton et al., 2001; Simon et al., 2005). As in SCZ, 22q11DS is associated with abnormally dilated LVs (Campbell et al., 2006; Kempton et al., 2010; Machado et al., 2007; Simon et al., 2005; Sztriha et al., 2004). Mouse models of 22q11DS (22q11DS mice) have similar robust changes in ventricular volume compared with human 22q11DS carriers (Ellegood et al., 2014). This finding indicates that 22q11DS mice are a valid model of SCZ-associated ventricular enlargement. However, the specific gene(s) within the microdeletion and pathogenic mechanisms responsible for ventricular enlargement remain unknown.

Several recent studies have linked the SCZ-related phenotypes in 22q11DS mice to the Dgcr8 (DiGeorge critical region 8) gene (Chun et al., 2014, 2017; Earls et al., 2012; Eom et al., 2017; Stark et al., 2008). Dgcr8 is important for synthesizing microRNAs (miRNAs), which are negative regulators of mRNA translation (Bartel, 2009). Haploinsufficiency of Dgcr8 leads to miRNA depletion and abnormally elevated expression of important proteins such as dopamine receptors in various brain regions, thus contributing to SCZ-related phenotypes in 22q11DS mice (Chun et al., 2014, 2017, Earls et al., 2010, 2012; Eom et al., 2017; Lindsay et al., 1999; Stark et al., 2008). Here the inventors describe a pathogenic mechanism involving Dgcr8-dependent miRNA depletion in ependymal cells that leads to decelerated motile ciliary beating and progressive ventricular enlargement in 22q11DS mouse models. This finding leads to potential treatments for ventricular enlargement and related diseases.

SUMMARY OF THE INVENTION

There is a great need in the art to develop effective treatments for diseases associated with ventricular enlargement, including schizophrenia and/or 22q11DS. The present disclosure addresses these and other needs by providing methods and compositions based on inhibitors of Drd1 or microRNAs miR-382-3p and miR-674-3p.

In one aspect, the disclosure provides a method for treatment and/or prevention of a disease associated with ventricular enlargement in a subject in need thereof, said method comprising administering to the subject a therapeutically effective amount of an inhibitor of Drd1, wherein said inhibitor inhibits an activity or expression of Drd1 in ependymal cells of the subject. Non-limiting examples of diseases associated with ventricular enlargement include, e.g., schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging. In one embodiment, the inhibitor of Drd1 is selected from the compounds listed in Table 1 or is an analog and/or derivative thereof. In one specific embodiment, the inhibitor of Drd1 is SCH23390.

In another aspect, the disclosure provides a method for treatment and/or prevention of a disease associated with ventricular enlargement in a subject in need thereof, said method comprising administering to the subject a therapeutically effective amount of (i) miR-382-3p and/or miR-674-3p or a mimic or a functional derivative thereof, or (ii) a vector expressing miR-382-3p and/or miR-674-3p or a mimic or a functional derivative thereof, or (iii) an agent capable of increasing the level or activity of miR-382-3p and/or miR-674-3p. Non-limiting examples of diseases associated with ventricular enlargement include, e.g., schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging. In one embodiment, miR-382-3p comprises the sequence AAUCAUUCACGGACAACACUU (SEQ ID NO: 1) or UCAUUCACGGACAACACUUUUU (SEQ ID NO: 2). In one specific embodiment, miR-382-3p consists of the sequence AAUCAUUCACGGACAACACUU (SEQ ID NO: 1) or UCAUUCACGGACAACACUUUUU (SEQ ID NO: 2). In one embodiment, the miR-674-3p comprises the sequence CACAGCUCCCAUCUCAGAACAA (SEQ ID NO: 3). In one specific embodiment, miR-674-3p consists of the sequence CACAGCUCCCAUCUCAGAACAA (SEQ ID NO: 3).

In one embodiment of any of the above methods of the disclosure, the administration is inside the ventricles of the subject (e.g., by intracerebroventricular injection).

In one embodiment of any of the above methods of the disclosure, the administration results in a decrease in ventricular enlargement. In one specific embodiment, the administration results in a decrease in ventricular enlargement of one or more of the brain lateral ventricles (LVs) and/or third ventricle (TV) of the subject.

In one embodiment of any of the above methods of the disclosure, the administration results in an increase in ciliary beating on ependymal cells lining the walls of lateral ventricles (LVs) of the subject.

In one embodiment of any of the above methods of the disclosure, the administration results in a decrease of dopamine receptor (Drd1) expression and/or function in ependymal cells lining the walls of ventricles of the subject.

In one embodiment of any of the above methods of the disclosure, the administration results in an increase in the level of miR-382-3p and/or miR-674-3p in ependymal cells lining the walls of ventricles of the subject.

In one embodiment of any of the above methods of the disclosure, the subject has an increased size of one or more brain ventricles (e.g., lateral ventricles (LVs) and/or third ventricle (TV)) as compared to a control (e.g., a predetermined standard, or the size in a healthy age- and gender-matched subject, or an average value for several such subjects).

In one embodiment of any of the above methods of the disclosure, the subject has a decreased ciliary beating on ependymal cells lining the walls of lateral ventricles (LVs) as compared to a control (e.g., a predetermined standard, or the beating in a healthy age- and gender-matched subject, or an average value for several such subjects).

In one embodiment of any of the above methods of the disclosure, the subject has an increased dopamine receptor (Drd1) expression and/or function in ependymal cells lining the walls of ventricles as compared to a control (e.g., a predetermined standard, or the dopamine receptor (Drd1) expression and/or function in a healthy age- and gender-matched subject, or an average value for several such subjects).

In one embodiment of any of the above methods of the disclosure, the subject has a decreased level of miR-382-3p and/or miR-674-3p in ependymal cells lining the walls of ventricles as compared to a control (e.g., a predetermined standard, or the level in a healthy age- and gender-matched subject, or an average value for several such subjects).

In one embodiment of any of the above methods of the disclosure, the method further comprises determining the size of brain ventricles (e.g., lateral ventricles (LVs) and/or third ventricle (TV)) of the subject.

In one embodiment of any of the above methods of the disclosure, the method further comprises assessing ciliary beating on ependymal cells lining the walls of lateral ventricles (LVs) of the subject. Non-limiting examples of the methods for assessing ciliary beating on ependymal cells include, e.g., measuring the average velocity of fluorescent microbead movement at the apical surface of ependymal cells, measuring motile cilia beating frequency (CBF) by linescan imaging, and measuring ependymal motile cilia beating frequency (CBF) by 2-photon imaging at the surface of LV walls (one or more methods can be used).

In one embodiment of any of the above methods of the disclosure, the method further comprises determining dopamine receptor (Drd1) expression in ependymal cells of the subject.

In one embodiment of any of the above methods of the disclosure, the method further comprises determining the level of miR-382-3p and/or miR-674-3p in ependymal cells of the subject. Non-limiting examples of the methods which can be used for determining the level of miR-382-3p and/or miR-674-3p include, e.g., hybridization, array-based assays, PCR-based assays (e.g., qPCR), and sequencing. In one specific embodiment, the level of miR-382-3p and/or miR-674-3p is determined prior to the administration of the treatment. In another specific embodiment, the level of miR-382-3p and/or miR-674-3p is determined both prior and after the administration of the treatment.

In one embodiment of any of the above methods of the disclosure involving the use of a vector expressing miR-382-3p and/or miR-674-3p or a mimic or a functional derivative thereof, the vector is selected from adeno-associated virus (AAV) vectors, lentivirus vectors, adenoviral vector, retroviral vectors, alphaviral vectors, vaccinia virus vectors, herpes simplex virus (HSV) vectors, rabies virus vectors, and Sindbis virus vectors.

In one embodiment of any of the above methods of the disclosure, the method further comprises administering to the subject an additional treatment agent. In one specific embodiment, the additional treatment agent is an antipsychotic (e.g., haloperidol, clozapine, olanzapine, etc.).

In another aspect, the disclosure provides a method for determining efficacy of a treatment for a disease associated with ventricular enlargement in a subject, the method comprising:

(a) determining the level of miR-382-3p and/or miR-674-3p in ependymal cells, or a CSF or a blood sample obtained from the subject before the treatment, (b) determining the level of miR-382-3p and/or miR-674-3p in ependymal cells, or the CSF or a blood sample obtained from the subject after the treatment, (c) comparing the levels determined in steps (a) and (b), and (d) determining that the treatment is effective if the level of miR-382-3p and/or miR-674-3p in ependymal cells, or the CSF or the blood of the subject has increased after the treatment. In one embodiment, the level of miR-382-3p and/or miR-674-3p is determined using a method selected from hybridization, array-based assays, PCR-based assays (e.g., qPCR), and sequencing. In one embodiment, the method comprises administering the treatment to the subject before or after step (a). In one embodiment, the method comprises obtaining ependymal cells, or a CSF or a blood sample from the subject before and after the treatment.

In one embodiment of any of the above methods of the disclosure involving determining the level of miR-382-3p and/or miR-674-3p, prior to determining miR-382-3p and/or miR-674-3p level, miRNA is purified from the sample isolated from the subject.

In one embodiment of any of the above methods of the disclosure involving determining the level of miR-382-3p and/or miR-674-3p, the method further comprises the step of reducing or eliminating degradation of miRNA.

In a further aspect, the disclosure provides a method for determining the likelihood of developing a disease associated with ventricular enlargement in a subject, the method comprising:

(a) determining one or more of the following: i) the level of miR-382-3p and/or miR-674-3p in ependymal cells, or a CSF or a blood sample obtained from the subject, ii) the presence of one or more mutations in Dgcr8 gene in ependymal cells, or a CSF or a blood sample obtained from the subject, iii) the Dgcr8 mRNA or protein level in ependymal cells, or a CSF or a blood sample obtained from the subject, and iv) the level of Drd1 or another dopamine receptor in ependymal cells, or a CSF or blood sample obtained from the subject, (b) comparing the level determined in step (a) to a control level, and (c) determining that the subject is at risk of developing a disease associated with ventricular enlargement if i) the level of miR-382-3p and/or miR-674-3p is decreased as compared to the control, ii) one or more mutations is present in Dgcr8 gene as compared to the control, iii) the Dgcr8 mRNA or protein level is decreased as compared to the control, and/or iv) the level of Drd1 or another dopamine receptor is increased as compared to the control. In one embodiment, the control is a predetermined standard, or a healthy age- and gender-matched subject, or an average value for several such subjects. In one embodiment, the level of Drd1 or another dopamine receptor in ependymal cells is determined by immunostaining of the LV wall or measuring intracellular cAMP in the LV wall.

In one embodiment of any of the above methods for determining efficacy of a treatment or determining the likelihood of developing a disease associated with ventricular enlargement, the disease associated with ventricular enlargement is selected from schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging.

In one embodiment of any of the above methods of the disclosure, the subject is human.

In another aspect, the disclosure provides a kit for determining efficacy of a treatment for a disease associated with ventricular enlargement comprising primers and/or probes specific for miR-382-3p and/or miR-674-3p. In one embodiment, the kit further comprises miRNA isolation and/or purification means. In one embodiment, the kit further comprises instructions for use. Non-limiting examples of the diseases associated with ventricular enlargement include, e.g., schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging.

In another aspect, the disclosure provide use of (i) miR-382-3p and/or miR-674-3p or a mimic or a functional derivative thereof, or (ii) a vector expressing miR-382-3p and/or miR-674-3p or a mimic or a functional derivative thereof, (iii) an agent capable of increasing the level or activity of miR-382-3p and/or miR-674-3p, or (iv) an inhibitor of Drd1, wherein said inhibitor inhibits an activity or expression of Drd1 in ependymal cells, in the manufacture of a medicament in the treatment and/or prevention of a disease associated with ventricular enlargement. Non-limiting examples of the diseases associated with ventricular enlargement include, e.g., schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging.

In another aspect, the disclosure provides a pharmaceutical composition comprising miR-382-3p and/or miR-674-3p or a mimic or a functional derivative thereof and a pharmaceutically acceptable carrier or excipient. In one embodiment, said pharmaceutical composition is suitable for intracerebroventricular administration. In one embodiment, miR-382-3p comprises the sequence AAUCAUU-CACGGACAACACUU (SEQ ID NO: 1) or UCAUU-CACGGACAACACUUUU (SEQ ID NO: 2). In one specific embodiment, miR-382-3p consists of the sequence AAUCAUUCACGGACAACACUU (SEQ ID NO: 1) or UCAUUCACGGACAACACUUUU (SEQ ID NO: 2). In one embodiment, the miR-674-3p comprises the sequence CACAGCUCCCAUCUCAGAACAA (SEQ ID NO: 3). In one specific embodiment, miR-674-3p consists of the sequence CACAGCUCCCAUCUCAGAACAA (SEQ ID NO: 3).

In a related aspect, the disclosure provides a pharmaceutical dosage form comprising miR-382-3p and/or miR-674-3p or a mimic or a functional derivative thereof. In one embodiment, said dosage form is suitable for intracerebroventricular administration. In one embodiment, miR-382-3p comprises the sequence AAUCAUU-CACGGACAACACUU (SEQ ID NO: 1) or UCAUUCACGGACAACACUUUU (SEQ ID NO: 2). In one specific embodiment, miR-382-3p consists of the sequence AAUCAUUCACGGACAACACUU (SEQ ID NO: 1) or UCAUUCACGGACAACACUUUU (SEQ ID NO: 2). In one embodiment, the miR-674-3p comprises the sequence CACAGCUCCCAUCUCAGAACAA (SEQ ID NO: 3). In one specific embodiment, miR-674-3p consists of the sequence CACAGCUCCCAUCUCAGAACAA (SEQ ID NO: 3).

In another aspect, the disclosure provides a recombinant adeno-associated virus (rAAV) particle comprising a nucleic acid encoding miR-382-3p and/or miR-674-3p or a mimic or a functional derivative thereof. In one embodiment, the rAAV particle comprises a capsid derived from AAV1, AAV2, AAV5, AAV8, or AAV9. In one embodiment, the nucleic acid encoding miR-382-3p and/or miR-674-3p or a mimic or a functional derivative thereof is operably linked to a promoter selected from ubiquitin promoter, beta-actin promoter, and CMV promoter. In one embodiment, miR-382-3p comprises the sequence AAUCAUU-CACGGACAACACUU (SEQ ID NO: 1) or UCAUU-CACGGACAACACUUUUU (SEQ ID NO: 2). In one specific embodiment, miR-382-3p consists of the sequence AAUCAUUCACGGACAACACUU (SEQ ID NO: 1) or UCAUUCACGGACAACACUUUUU (SEQ ID NO: 2). In one embodiment, the miR-674-3p comprises the sequence CACAGCUCCCAUCUCAGAACAA (SEQ ID NO: 3). In one specific embodiment, miR-674-3p consists of the sequence CACAGCUCCCAUCUCAGAACAA (SEQ ID NO: 3).

In a related aspect, the disclosure provides a pharmaceutical composition comprising any of the above rAAV particles of the disclosure and a pharmaceutically acceptable carrier or excipient. In one embodiment, said pharmaceutical composition is suitable for intracerebroventricular administration.

In another related aspect, the disclosure provides a pharmaceutical dosage form comprising any of the above rAAV particles of the disclosure. In one embodiment, said dosage form is suitable for intracerebroventricular administration.

These and other aspects of the present invention will be apparent to those of ordinary skill in the art in the following description, claims and drawings.

BRIEF DESCRIPTION OF THE DRAWINGS

U.S. Provisional Application No. 62/878,267 contains copies of several of the drawing(s) below in color, which can be provided by the United States Patent and Trademark Office upon request and payment of the necessary fee.

(FIG. 1A) Map of 22q11DS orthologs deleted in Df(16)1/+ mice. (FIGS. 1B-1E) Representative MRIs of the rostral and caudal brains (FIGS. 1B, 1D) and total ventricle volumes (FIGS. 1C, 1E) of 4- and 8-month-old WT and Df(16)1/+ mice (FIGS. 1B, 1C) and WT and Dgcr8$^{+/-}$ mice (FIGS. 1D, 1E). Data from the 4-month-old WT (n=10) and Df(16)/+ (n=11) mice were analyzed using the Mann-Whitney rank-sum test (U=29, p=0.07), and that from 8-month-old WT (n=15) and Df(16)1/+ (n=14) mice were analyzed in the same manner (U=48, *p<0.05). Data from the 4-month-old WT (n=17) and Dgcr8$^{+/-}$ (n=18) mice were analyzed using the two-tailed Student's t-test (t$_{33}$=1.54; p=0.13), and that from 8-month-old WT (n=26) and Dgcr8$^{+/-}$ (n=33) mice were analyzed using the Mann-Whitney rank-sum test (U=231, *p<0.01). Scale bars, 8 mm Data in this and other figures that are graphed as box plots show the mean and median values as thick and thin lines, respectively. The box corresponds to 25$^{th}$ and 75$^{th}$ percentiles, the whiskers indicate the 10$^{th}$ and 90$^{th}$ percentiles, and the filled circles indicate the 5$^{th}$ and 95$^{th}$ percentiles.

FIGS. 2A-2K. Dgcr8 Haploinsufficiency Slows Ependymal Ciliary Beating. (FIG. 2A) Images of fluorescent beads at consecutive time points, which are shown in seconds. (FIG. 2B) The average bead speed is an indicator of the ependymal flow rate in 8-month-old whole mounts from WT (439 beads, 6 mice) and Dgcr8$^{+/-}$ (450 beads, 6 mice) animals. Data were analyzed using the Mann-Whitney rank-sum test (U=72837, *p<0.001). (FIG. 2C) A coronal section of the brain (top) with the magnified region of the LV wall (bottom) in Arl13b$^{eGFP}$ mice. Motile cilia were labeled with eGFP and depicted in grayscale mode. (FIG. 2D) Kymographs of cilia beating measured ex vivo brain slices from WT (Dgcr8$^{+/+}$;Arl13b$^{eGFP}$) and Dgcr8$^{+/-}$ (Dgcr8$^{+/-}$; Arl13b$^{eGFP}$) mice. (FIGS. 2E-2H) Ciliary beating frequency (CBF) in ex vivo brain slices from WT and Dgcr8$^{+/-}$ mice at 2-3 months (FIG. 2E), 4-5 months (FIG. 2F), 6-7 months (FIG. 2G), and 8-9 months (FIG. 2H) of age. In FIG. 2E, 82 ciliary bundles in 3 WT mice and 81 ciliary bundles in 3 Dgcr8$^{+/-}$ mice (U=3227, p=0.76) were assessed. In FIG. 2F, 132 ciliary bundles in 5 WT mice and 143 ciliary bundles in 5 Dgcr8$^{+/-}$ mice (U=8037, *p<0.05) were assessed. In FIG. 2G, 120 ciliary bundles in 4 WT mice and 112 ciliary bundles in 4 Dgcr8$^{+/-}$ mice (U=4709, *p<0.001) were assessed. In FIG. 2H, 145 ciliary bundles in 5 WT mice and 159 ciliary bundles in 5 Dgcr8$^{+/-}$ mice (U=7116, *p<0.001) were assessed (Mann-Whitney rank-sum test). (FIG. 2I) Experimental schematics for imaging ependymal CBF in vivo in an anesthetized mouse. (FIG. 2J) Representative images of motile cilia in the LV wall of an anesthetized mouse at consecutive time points. (FIG. 2K) Average CBF measured in vivo in WT and Dgcr8$^{+/-}$ mice (98 ciliary bundles in 3 WT mice, 88 ciliary bundles in 5 Dgcr8$^{+/-}$ mice; Mann-Whitney rank-sum test; U=2509, *p<0.001).

FIGS. 3A-3P. Normal Cilia Structure and Planar Polarity of Ependymal Cells in Dgcr8$^{+/-}$ Mice. (FIGS. 3A-3D) Representative TEM images of motile cilia in ependymal cells of WT and Dgcr8$^{+/-}$ mice. Cilia are transected at the levels of the axoneme (FIGS. 3A, 3B) or basal body (FIGS. 3C, 3D). In FIG. 3M, 105 cilia in 3 mice of each genotype were analyzed using the Mann-Whitney rank-sum test (U=5156, p=0.42). In FIG. 3N, 72 cilia in 3 mice of each genotype were analyzed in the same matter (U=2379, p=0.39). In FIG. 3O, 309 cells in 3 WT mice and 305 cells in 3 Dgcr8$^{+/-}$ mice were analyzed using the Normality Shapiro-Wilk test (U=44,160, p=0.18). (FIG. 3P) Distribution of the basal body patch is plotted on a polar histogram. Average angles of the individual vectors in each imaged section were normalized to 0°, and distributions of the angles were compared in WT (235 cells, 3 mice) and Dgcr8$^{+/-}$ (135 cells, 3 mice) animals. The data were analyzed using Watson's U2 two-sample test of homogeneity (t=0.13, p=0.13).

FIGS. 4A-4I. Dgcr8 Haploinsufficiency Increases the Expression of Dopamine Receptor Drd1 in the LV Wall. (FIG. 4A) Confocal images of Drd1 expression in the ependymal cells of whole-mount LV walls from WT or Dgcr8$^{+/-}$ mice. Acetyl-tubulin antibody is used as a marker of motile cilia and DAPI stains the nuclei. (FIG. 4B) Super-resolution microscopic images of coronal brain sections from the Foxj1$^{Cre}$;Drd1$^{+/+}$ and Foxj1$^{Cre}$;Drd1$^{β/β}$ mice show expression of Drd1 in motile cilia. Acetyl-tubulin antibody is used as a marker of motile cilia. (FIG. 4C) Immunogold EM images show localization of immunogold-tagged Drd1 in the cytoplasm of ependymal cells and near the microtubules of cilia, including the axoneme, basal body, and distal appendages of the basal body (arrows). (FIG. 4D) Representative immunoblotting of Drd1 and Drd2 in the LV wall of WT and Dgcr8$^{+/-}$ mice. (FIGS. 4E-4G) Quantification of Drd1 (FIG. 4E) and Drd2 (FIG. 4F) protein levels and the cAMP level (FIG. 4G) in the LV wall of WT and $Dgcr8^{+/-}$ mice. In FIG. 4E, the data represent 8 mice per group and were analyzed using the two-tailed Student's t-test ($t_{14}$=4.80, *p<0.001). In FIG. 4F, 8 mice per group were included, and the data were analyzed in the same manner ($t_{14}$=0.89, p=0.39). In FIG. 4G, 4 WT and 3 $Dgcr8^{+/-}$ mice were included in each experiment, which were run in triplicate and analyzed using the two-tailed Student's t-test ($t_5$=3.72, *p<0.05). (FIGS. 4H, 4I) Average CBF in ex vivo brain slices from 6-month-old WT and $Dgcr8^{+/-}$ mice in the absence (85 ciliary bundles in 3 WT mice and 88 ciliary bundles in 3 $Dgcr8^{+/-}$ mice) or presence of Drd1 antagonist SCH23390 (93 ciliary bundles in 3 WT mice and 85 ciliary bundles in 3 $Dgcr8^{+/-}$ mice). Data were analyzed using one-way ANOVA ($F_3$=24.99, *p<0.001) (FIG. 4H) and in slices from 4- to 5-month-old WT mice in the presence of vehicle (DMSO) (67 ciliary bundles in 3 mice) or the Drd1 agonist SKF81297 (60 ciliary bundles in 3 mice). Data were analyzed using the Mann-Whitney rank-sum test (U=1043, *p<0.001) (FIG. 4I).

FIGS. 5A-5G. Drd1-Targeting miRNAs Are Depleted in $Dgcr8^{+/-}$ Mice, and Deletion of miRNA Seed Site on Drd1 3'UTR Causes Ventriculomegaly. (FIG. 5A) A miRNA microarray volcano plot depicting changes in miRNA expression in the LV wall of male $Dgcr8^{+/-}$ mice compared to that in male WT mice. (FIG. 5B) Normalized relative levels of miR-153-5p, miR-382-3p, and miR-674-3p measured by qPCR in the LV wall in WT (8 mice) and $Dgcr8^{+/-}$ littermates (8 mice). The data were analyzed using Mann-Whitney rank-sum test (U=12, *p<0.001 for miR-153-5p; U=133, * p<0.001 for miR-382-3p; U=0, *p<0.001 for miR-674-3p). (FIG. 5C) Normalized relative expression of miR-153-3p (8 mice), miR-382-3p (8 mice), and miR-674-3p (8 mice) in cerebellum, cortex, hippocampus, LV wall, striatum, kidney, and liver, as measured by qPCR. Data were analyzed using Kruskal-Wallis one-way analysis ($H_6$=133.96, p<0.001 for miR-153-5p; $H_6$=127.59, p<0.001 for miR-382-3p; $H_6$=149.63, p<0.001 for miR-674-3p). (FIG. 5D) The predicted miRNA target sites of miR-382-3p (solid box) and miR-674-3p (dotted box) on the Drd1 3'UTR (NM_010076). The overlapped nucleotide G between the two miRNA seed sites within the 13-bp sequence is indicated with an arrow. Figure discloses SEQ ID NOS 2, 43, 44, 3, and 45, respectively, in order of appearance. (FIG. 5E) Validation of the 13-base deletion in the Drd1 3'UTR of the $Drd1^{\Delta13p-/-}$ mouse by cDNA sequencing. The blue shaded area indicates the 13-bp seed site in the WT Drd1 3'UTR, which is deleted in $Drd1^{\Delta13p-/-}$ mice. Figure discloses SEQ ID NOS 46 and 47, respectively, in order of appearance. (FIGS. 5F, 5G) Total ventricle volumes (FIG. 5F) and LV volumes (FIG. 5G) of 2-month (n=19/20), 4-month (n=18/16), and 8-month-old (n=12/11) WT and $Drd1^{\Delta13b+/-}$ mice. Data were analyzed using the two-way repeated-measures ANOVA. (FIG. 5F) Age: F(2,37)=21.7, p<0.001, genotype: F(1,37)=3.1, p=0.085. (FIG. 5G) Age: F(2,37)=20.5, p<0.001, genotype: F(1,37)=4.35, *p=0.04.

FIGS. 6A-6H. Knockdown of Drd1-Targeting miRNAs in the Ependymal Cells Mimics Ventricular Enlargement Seen in 22q11DS mice. (FIG. 6A) Confocal images of miRNA (GFP) expression in the coronal sections of $Foxj1^{Cre}$;Ai14 brains. Cre expression is marked with tdTomato, and DAPI counterstains the nuclei. (FIG. 6B-6D) Normalized levels of miR-382-3p (FIG. 6B), miR-674-3p (FIG. 6C), and Drd1 mRNA (FIG. 6D) in the LV wall injected with AAV1 expressing GFP or miR-382-3p sponge (FIGS. 6B and 6D) or miR-674-3p sponge (FIGS. 6C and 6D). In FIG. 6B, 3 mice per group were analyzed using the Mann-Whitney rank-sum test (U=42, *p<0.01). In FIG. 6C, 4 mice per group were analyzed using the two-tailed Student's t-test ($t_{22}$=5.60, *p<0.001). In FIG. 6D, the data were analyzed using the two-tailed Student's t-test ($t_{22}$=3.71, *p<0.001 for miR-382-3p sponge; $t_{20}$=2.47, *p<0.05 for miR-674-3p sponge). (FIG. 6E) Representative MRIs of the rostral and caudal brains injected with an AAV1 expressing a scramble control, miR-382-3p sponge, or miR-674-3p sponge. (FIGS. 6F-6H) The total ventricular volume (FIG. 6F), third ventricular volume (FIG. 6G), and CBF (FIG. 6H) of 8-month-old WT mice injected with AAV1 expressing scramble (control, 27 mice), miR-382-3p sponge (28 mice), or miR-674-3p sponge (28 mice) into the intracerebroventricular space at 2-3 months of age. Data were analyzed using one-way ANOVA, FIG. 6F: $F_3$=21.82, *p<0.001, FIG. 6G: $H_2$=35.98, *p<0.001, FIG. 6H: control (136 ciliary bundles in 4 mice), miR-382-3p sponge (124 ciliary bundles in 4 mice), and miR-674-3p sponge (120 ciliary bundles in 5 mice, $H_2$=15.69, *p<0.001). Scale bar, 8 mm.

FIGS. 7A-7F. Overexpression of Drd1-Targeting miRNAs in the Ependymal Cells Rescues 22q11DS-Mediated Ventriculomegaly. (FIG. 7A) Representative MRIs of the brains of WT or Df(16)+ mice injected with an AAV1 expressing scramble control, miR-382-3p (miR-382 OE), or miR-674-3p (miR-674 OE). (FIG. 7B) Mean total ventricular volume of 8-month-old WT and Df(16)/+ mice injected with an AAV1 expressing scramble control (Control: 9 WT mice, 9 Df(16)/+ mice; two-tailed Student's t-test; $t_{16}$=2.39, *p<0.05), miR-382-3p (miR-382 OE: 21 WT mice, 17 Df(16)/+ mice; two-tailed Student's t-test; $t_{36}$=1.14, p=0.26), or miR-674-3p (miR-674 OE: 20 WT mice, 16 Df(16)/+ mice; two-tailed Student's t-test; $t_{34}$=0.66, p=0.52) into the intracerebroventricular space at 2-3 months of age. (FIG. 7C) CBF measured in ex vivo brain slices from 8-month-old WT mice injected with an AAV1 expressing scramble control (Control: 111 ciliary bundles in 5 WT mice, 90 ciliary bundles in 5 Df(16)/+ mice; Mann-Whitney rank-sum test; U=3497, *p<0.001), miR-382-3p (miR-382 OE: 139 ciliary bundles in 5 WT mice, 156 ciliary bundles in 5 Df(16)/+ mice; Mann-Whitney rank-sum test; U=9962, p=0.23), or miR-674-3p (miR-674 OE: 151 ciliary bundles in 5 WT mice, 148 ciliary bundles in 5 Df(16)/+ mice; Mann-Whitney rank-sum test; U=10,622, p=0.46. (FIG. 7D) Representative MRIs of the brains of WT or $Dgcr8^{+/-}$ mice injected with an AAV1 expressing scramble (Control), miR-382-3p (miR-382 OE), or miR-674-3p (miR-674 OE). (FIG. 7E) Mean total ventricular volume of 8-month-old WT or $Dgcr8^{+/-}$ mice injected with AAV1 expressing scramble control (Control: 10 WT mice, 9 $Dgcr8^{+/-}$ mice; two-tailed Student's t-test; $t_{17}$=3.20, *p<0.01), miR-382-3p (miR-382 OE: 22 WT mice, 24 $Dgcr8^{+/-}$ mice; two-tailed Student's t-test; $t_{44}$=1.17, p=0.25), or miR-674-3p (miR-674 OE: 17 WT mice, 16 $Dgcr8^{+/-}$ mice; two-tailed Student's t-test; $t_{31}$=0.58, p=0.57). (FIG. 7F) CBF measured in ex vivo brain slices from 8-month-old WT mice injected with AAV1 expressing scramble control (Control: 153 ciliary bundles in 5 WT mice, 128 ciliary bundles in 5 $Dgcr8^{+/-}$ mice; Mann-Whitney rank-sum test; U=6736.5, *p<0.001), miR-382-3p (miR-382 OE: 134 ciliary bundles in 5 WT mice, 131 ciliary bundles in 4 $Dgcr8^{+/-}$ mice; Mann-Whitney rank-sum test; U=7640.5, p=0.07), or miR-674-3p (miR-674 OE: 162 ciliary bundles in 6 WT mice, 168 ciliary bundles in 6 $Dgcr8^{+/-}$ mice; Mann-Whitney rank-sum test; U=12,165, p=0.10). Scale bars, 8 mm.

FIGS. 8A-8K. Neuroanatomical Features in the Brains of Df(16)1/+ and $Dgcr8^{+/-}$ Mice, Related to FIGS. 1A-1E. (A-J) Cortical (CTX) thickness (FIGS. 8A, 8B, 8F, 8G), hippocampal (HPC) volume (FIGS. 8C, 8H), total brain volume with CSF (FIGS. 8D, 8I) and without CSF (FIGS. 8E, 8J) in 4- and 8-month-old Df(16)1/+ (FIGS. 8A-8E) and Dgcr8$^{+/-}$ (FIGS. 8F-8J) mice and their respective litter-mates. (FIGS. 8A-8E) 4-month-old: WT (10 mice) and Df(16)1/+ (11 mice); two-tailed Student's t-test; $t_{19}$=0.13, p=0.89 (FIG. 8A); $t_{19}$=1.25, p=0.23 (FIG. 8B); $t_{19}$=0.73, p=0.48 (FIG. 8C); Mann-Whitney rank-sum test; U=30, p=0.08 (FIG. 8D); U=21, p=0.02 (FIG. 8E), 8-month-old: WT (15 mice) and Df(16)1/+ (14 mice); $t_{27}$=1.82, p=0.08 (FIG. 8A); $t_{27}$=1.32, p=0.20 (FIG. 8B); $t_{27}$=0.51, p=0.61 (FIG. 8C); $t_{27}$=0.87, p=0.39 (FIG. 8D); $t_{27}$=0.46, p=0.65 (FIG. 8E), (FIGS. 8F-8J) 4-month-old: WT (10-17 mice) and Dgcr8$^{+/-}$ (11-18 mice); $t_{33}$=0.48, p=0.64 (FIG. 8F); $t_{33}$=1.81, p=0.08 (FIG. 8G); U=113, p=0.20 (FIG. 8H); $t_{19}$=1.92, p=0.07 (FIG. 8I); $t_{19}$=1.22, p=0.24 (FIG. 8J), 8-month-old: WT (26 mice) and Dgcr8$^{+/-}$ (32-33 mice); $t_{57}$=0.07, p=0.95 (FIG. 8F); $t_{57}$=0.43, p=0.67 (FIG. 8G); $t_{57}$=1.17, p=0.25 (FIG. 8H); $t_{56}$=0.27, p=0.79 (FIG. 8I); $t_{56}$=0.07, p=0.95 (FIG. 8J). (FIG. 8K) CSF osmolality in 8-month-old Dgcr8$^{+/-}$ (n=14) and WT (n=14) mice. Mann-Whitney rank-sum test; U=0, p=0.33. Data are shown as the mean±S.E.M. (FIGS. 8A-8J) Data graphed as box plots show the mean and median values as thick and thin lines, respectively. The box corresponds to $25^{th}$ and $75^{th}$ percentiles, the whiskers indicate the $10^{th}$ and $90^{th}$ percentiles, and the filled circles indicate the $5^{th}$ and $95^{th}$ percentiles.

FIGS. 9A-9C. The Effect of Conditional Deletion of Dgcr8 in Ependymal Cells on Ventricular Enlargement, Related to FIGS. 1A-1E. (FIG. 9A) Representative MRIs of the rostral and caudal brains from the Dgcr8-conditional knockout mice. (FIG. 9B) Normalized Dgcr8 mRNA levels in the LV wall (8 mice per group with duplicate experiment; Kruskal-Wallis one-way ANOVA on ranks: $H_2$=12.99, *p<0.01). (FIG. 9C) Total ventricular volume (Foxj1$^{Cre}$; Dgcr8$^{+/+}$ (20 mice), Foxj1$^{Cre}$;Dgcr8$^{fl/+}$ (30 mice), and Foxj1$^{Cre}$;Dgcr8$^{fl/fl}$ (13 mice) animals. Kruskal-Wallis one-way ANOVA on ranks: $H_2$=30.53, *p<0.001). All mice were 8 months old. Scale bar, 8 mm.

FIGS. 10A-10L. Normal Development of Neural Progenitors in the Subventricular Zone of Dgcr8$^{+/-}$ Mice, Related to FIGS. 2A-2K and FIGS. 3A-3P. (FIGS. 10A-10G) Proliferation of neural progenitors in the SVZ. (FIG. 10A) Confocal images of BrdU and Ki67 staining in the SVZ of 4- and 8-month-old Dgcr8$^{+/-}$ and WT mice. (FIGS. 10B-10G) Average numbers of Ki67-positive (FIGS. 10B, 10E), BrdU-positive (FIGS. 10C, 10F), and Ki67/BrdU-positive (FIGS. 10D, 10G) cells in the SVZ of 4- and 8-month-old Dgcr8$^{+/-}$ and WT mice. (FIGS. 10B-10G) Data from 4-month-old WT (12 brain sections, 4 mice) and Dgcr8$^{+/-}$ (12 brain sections, 4 mice); two-tailed Student's t-test; $t_{22}$=1.39, p=0.18 (FIG. 10B); $t_{22}$=0.60, p=0.56 (FIG. 10C); $t_{22}$=0.75, p=0.46 (FIG. 10D). Data from 8-month-old WT (12-23 brain sections, 5 mice) and Dgcr8$^{+/-}$ (11-17 brain sections, 5 mice) animals; $t_{38}$=0.69, p=0.50 (FIG. 10E); $t_{21}$=0.23, p=0.82 (FIG. 10F); $t_{21}$=0.26, p=0.80 (FIG. 10G). (FIGS. 10H-10J) Apoptotic cell death in the SVZ. Confocal images of cleaved caspase-3 staining (FIG. 10H: arrows indicate cleaved caspase-3-positive cells) and average numbers of caspase-3-positive cells in the SVZ of 4- and 8-month-old Dgcr8$^{+/-}$ and WT mice (FIGS. 10I, 10J). (FIG. 10I) Data from 4-month-old WT (14 brain sections, 4 mice) and Dgcr8$^{+/+}$ (15 brain sections, 4 mice) animals; Mann-Whitney rank-sum test; U=96, p=0.71. (FIG. 10J) Data from 8-month-old WT (11 brain sections, 3 mice) and Dgcr8$^{+/-}$ (9 brain sections, 3 mice) animals; U=68, p=0.47. (FIG. 10K) Confocal images of doublecortin (DCX) (red, top) and BrdU (green, bottom) staining. (FIG. 10L) Average numbers of BrdU-positive cells in the olfactory bulb of 8-month-old WT (18 brain sections, 3 mice) and Dgcr8$^{+/-}$ (13 brain sections, 3 mice) animals. Two-tailed Student's t-test; $t_{29}$=0.79, p=0.44. Data are shown as the mean±S.E.M.

(FIG. 12A) The qRT-PCR analysis of the levels of recombinant miR-153-5p (n=5, control n=6), miR-382-3p (n=3, control n=3), or miR-674-3p (n=3, control n=3) compared to respective controls (Mann-Whitney rank-sum test; miR-153-5p: U=0, *p<0.01, miR-382-3p: two-tailed Student's t-test; $t_4$=22.58, *p<0.001, miR-674-3p: two-tailed Student's t-test; $t_4$=24.41, *p<0.001) in the Neuro2A mouse cell line. (FIG. 12B) Luciferase assay (one-way ANOVA on Shapiro-Wilk normality test: $F_3$=20.54, *p<0.001) in HEK293 cells co-transfected with Drd1 3'UTR-containing luciferase vector and miR-153-5p OE (n=12), miR-382-3p OE (n=10), miR-674-3p OE (n=10), or control vectors (n=13). Data are shown as the mean±S.E.M.

(FIG. 13A) Luciferase activity measured in Neuro 2a cells transfected with luciferase reporter vector alone, luciferase reporter vector encoding miR-382-3p sponges (two-tailed Student's t-test; $t_4$=1.62, p=0.18) containing two ($t_4$=23.00, *p<0.001), four ($t_4$=24.35, *p<0.001), or six ($t_4$=9.17, *p<0.001) miRNA-binding sites or scrambled sites ($t_4$=2.36, p=0.08) in the presence of control pGIPZ vector or pGIPZ vector encoding miR-382-3p. Based on these experiments, the miR-382-3p sponge with six seed sites was chosen for in vivo experiments. (FIG. 13B) Luciferase activity in Neuro2a cells transfected with luciferase reporter vector alone, luciferase reporter vector encoding miR-674-3p sponges ($t_4$=14.13, *p<0.001) containing two ($t_4$=14.25, *p<0.001), four ($t_4$=80.70, *p<0.001), or six miRNA-binding sites ($t_4$=26.67, *p<0.001), or scrambled ($t_4$=1.11, p=0.33) sites in the presence of control pGIPZ vector or pGIPZ vector encoding miR-674-3p. Data are shown as the mean±S.E.M.

(FIG. 14A) Position of the LV wall in the sagittal brain (top) and fluorescent image of GFP in the whole mount excised from the LV wall after injection of AAV1-miRNA-GFP in WT mice (bottom). The adhesion region is denoted by an asterisk. (FIG. 14B) Confocal micrographs of AAV1-miRNA-GFP-expressing cell types in the SVZ. GFP-expressing cells that were also tdTomato-positive were stained with antibodies against the ependymal cell marker S100β but not with antibodies against the proliferating progenitor markers GFAP or Ki67. Abbreviations: A, anterior; D, dorsal; LV, lateral ventricle; OB, olfactory bulb; P, posterior; V, ventral.

FIGS. 15A-15H. miRNA Sponges Expressed in the Ependymal Cells Do Not Affect Other Neuroanatomical Features or Planar Polarity of Ependymal Cells, Related to FIGS. 6A-6H. (FIGS. 15A-15E) Cortical (CTX) thickness (Normality Shapiro-Wilk test, FIG. 15A: One-way ANOVA, $F_2$=2.20, p=0.12, FIG. 15B: $F_2$=0.93, p=0.40), hippocampal (HPC) volume (FIG. 15C: $F_2$=0.24, p=0.79), total brain volume with CSF (FIG. 15D: $F_2$=2.00, p=0.14) or without CSF (FIG. 15E: $F_2$=1.46, p=0.24) in 8-month-old WT mice

13

Figures 15F, 15G:
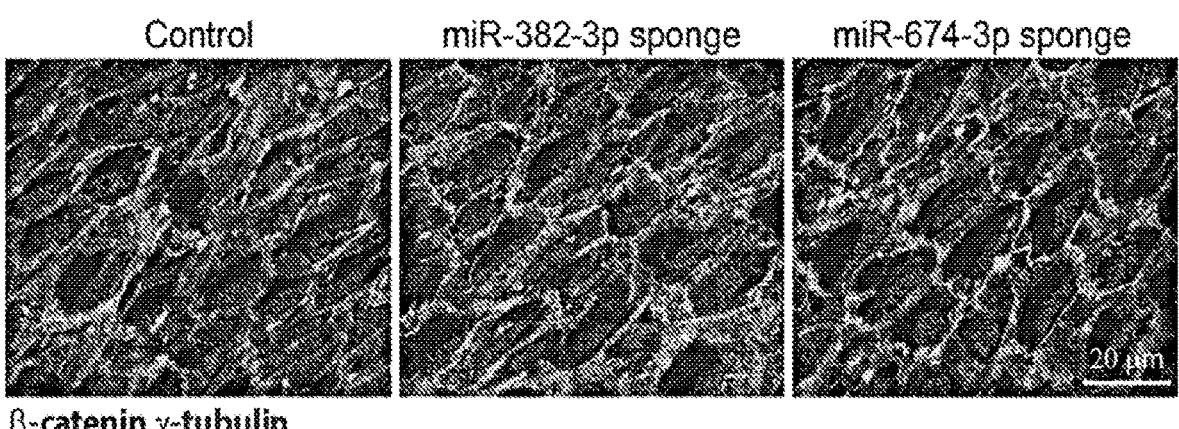
Figure 15H:
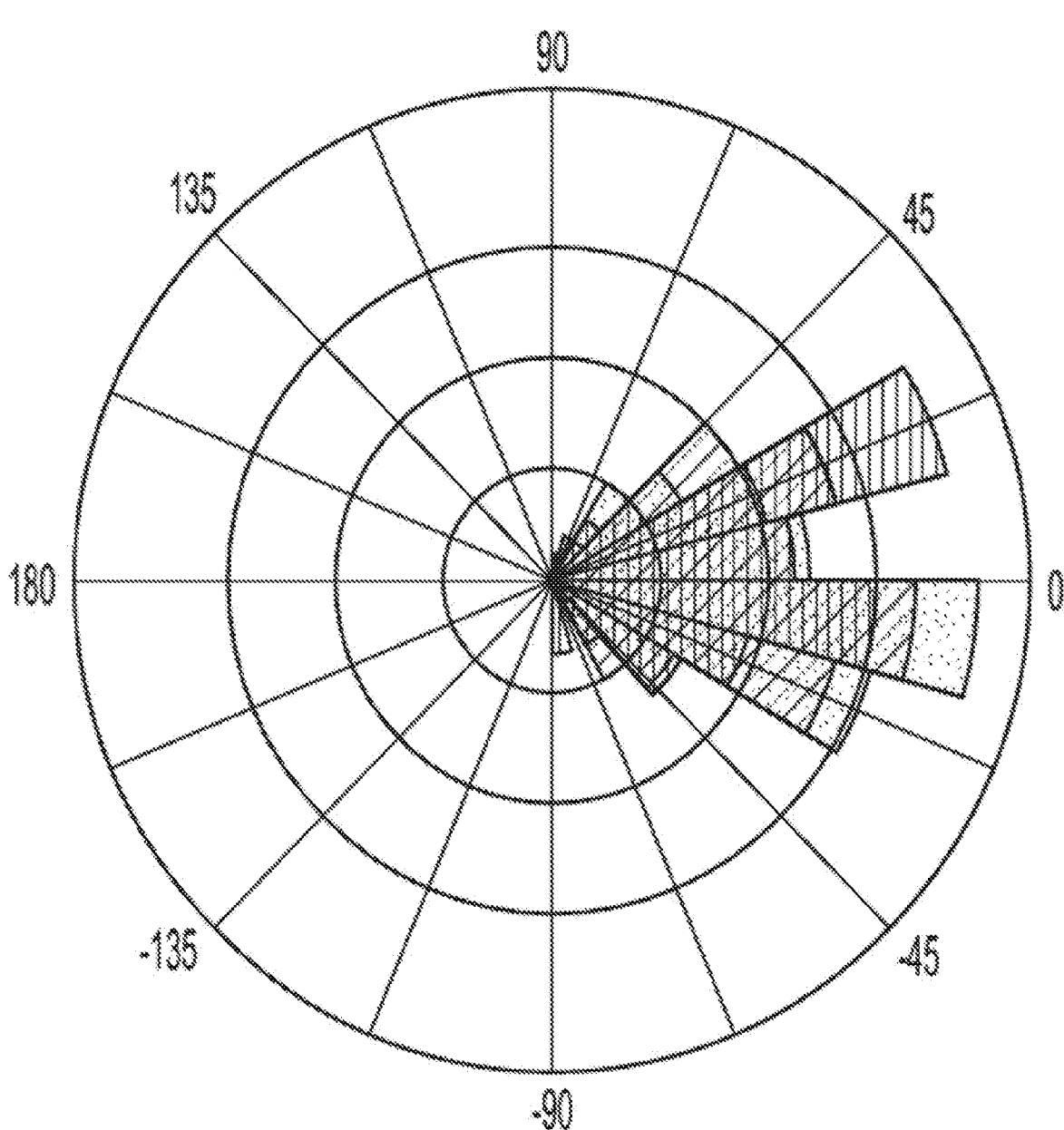

14 injected with AAV1-miR-382-3p sponge (28 mice), AAV1-miR-674-3p sponge (28 mice), or AAV1-scramble virus (Control: 27 mice) at 2-3 months of age. (FIG. 15F) Confocal images of basal body (BB) patch position (γ-tubulin, red) in ependymal cell junctions (β-catenin, green) in the LV wall of WT mice injected with control AAV1, AAV1-miR-382-3p sponge, or AAV1-miR-674-3p sponge virus. (FIG. 15G) Distance of BB displacement from the center of an ependymal cell (FIG. 15G: 129 cells from 3 control mice, 131 cells from 3 AAV1-miR-382-3p sponge-infected mice, or 131 cells from 3 AAV1-miR-674-3p sponge-infected mice; Normality Shapiro-Wilk test, FIG. 15A: One-way ANOVA, $H_2$=4.73, p=0.09). (FIG. 15H) Distribution of BB patch plotted on a polar histogram. Average angles of the individual vectors in each imaged section were normalized to 0° and distributions of the angles were compared to control (130 cells, 3 mice), AAV1-miR-382-3p sponge- (131 cells, 3 mice), or AAV1-miR-674-3p sponge- (147 cells, 3 mice) infected mice. Watson's U2 two-sample test of homogeneity; t=0.13, p>0.1 for control vs AAV1-miR-382-3p sponge and t=0.05, p>0.10 for control vs AAV1-miR-674-3p sponge.

Figures 16A, 16B, 16C:
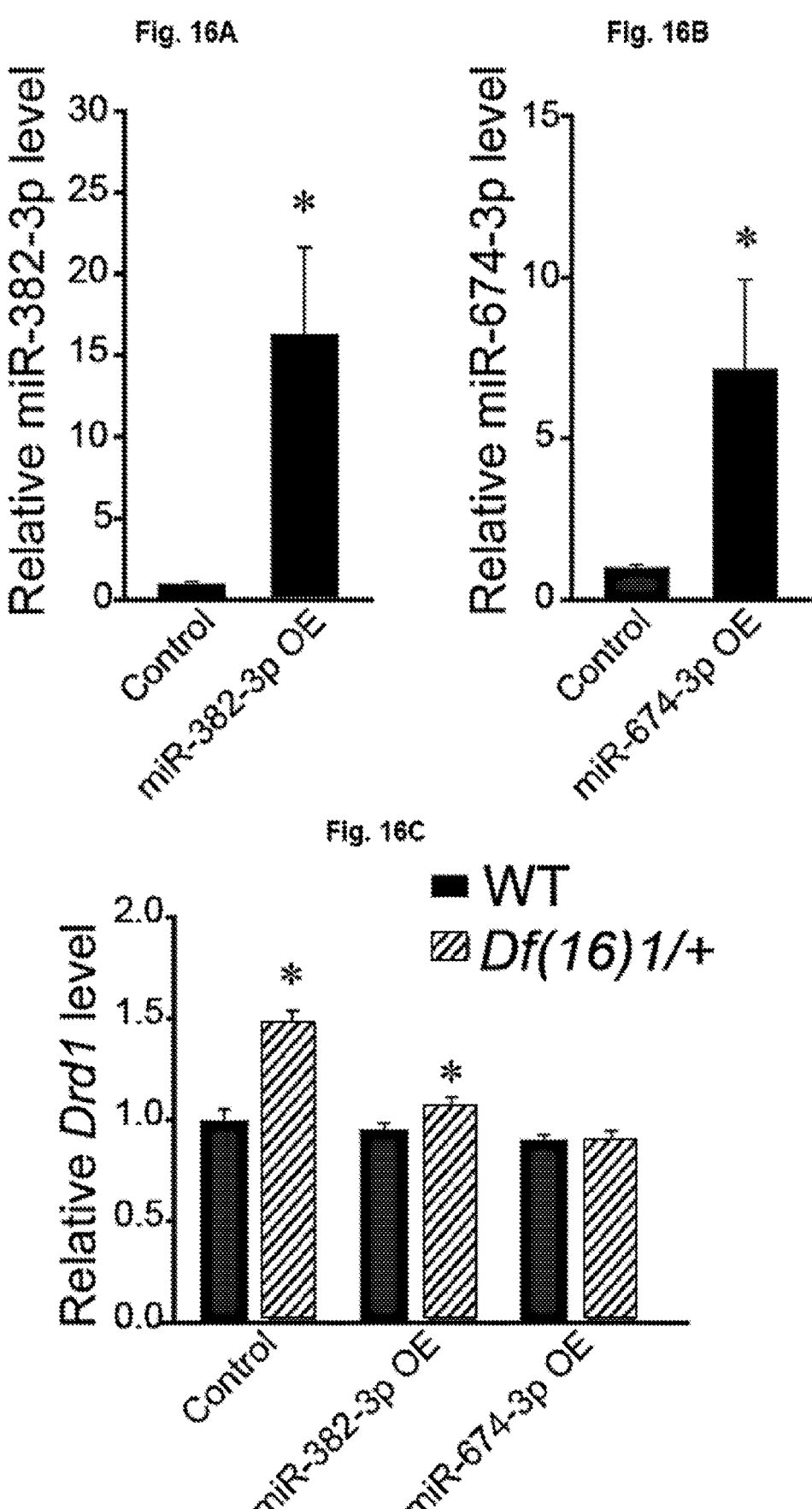

FIGS. 16A-16C. Validation of the Overexpression of miRNAs in Vivo, Related to FIGS. 7A-7F. (FIGS. 16A-16B) The levels of miR-382-3p (FIG. 16A) or miR-674-3p (FIG. 16B) in the LV wall extracted from WT mice infected with AAV1 expressing scramble-GFP (control), miR-382-3p (miR-382-3p OE), or miR-674-3p (miR-674-3p OE) (Mann-Whitney rank-sum test; miR-382-3p: U=0, *p<0.001, miR-674-3p: U=69, *p<0.001). (FIG. 16C) Normalized Drd1 mRNA in the LV wall extracted from WT (black) or Df(16) 1/+ (red) mice injected with AAV1 expressing control, miR-382-3p OE, or miR-674-3p OE. (Control: 8 mice per group; Mann-Whitney rank-sum test; U=63.5, *p<0.001, miR-382-3p OE: 8 WT mice, 8 Df(16)/+ mice; Mann-Whitney rank-sum test; U=158, *p<0.05, miR-674-3p OE: 7 WT mice, 8 Df(16)/+ mice; Mann-Whitney rank-sum test; U=229, p=0.61. Data are shown as the mean±S.E.M.

DETAILED DESCRIPTION OF THE INVENTION

The present disclosure is based on an unexpected discovery that miR-382-3p and/or miR-674-3p miRNAs are depleted in 22q11 deletion syndrome (which in 30% cases leads to schizophrenia) and this leads to abnormal elevation of dopamine receptors (Drd1) in the ependymal cells lining the ventricular walls.

Using murine models of schizophrenia-associated 22q11DS, it was found that progressive enlargement of the lateral and third ventricles and deceleration of ciliary beating on ependymal cells lining the ventricular walls. The cilia-beating deficit observed in brain slices and in vivo is caused by elevated levels of Drd1, which are highly expressed in motile cilia. Haploinsufficiency of the microRNA-processing gene Dgcr8 results in Drd1 elevation, which is brought about by a reduction in Drd1-targeting microRNAs miR-382-3p and miR-674-3p. Replenishing either microRNA in 22q11DS mice normalizes ciliary beating and ventricular size. Knocking down the microRNAs or deleting their seed sites on Drd1 mimicked the cilia-beating and ventricular deficits. These results suggest that the Dgcr8-miR-382-3p/miR-674-3p-Drd1 mechanism underlies deceleration of ciliary motility and progressive ventricular enlargement and infer a ciliopathic component of schizophrenia pathogenesis.

Based on these observations, the disclosure provides in certain embodiments a targeted therapy against progressive enlargement of brain ventricles, by replenishing miR-382-3p or miR-674-3p or inhibiting Drd1 in ependymal cells.

Definitions

As used herein, the term "schizophrenia" includes a condition generally described as schizophrenia or a condition having symptoms related thereto. Schizophrenia can be considered a disease with a spectrum of manifestations with various threshold levels. Symptoms of schizophrenia may appear in a range of related disorders including classical schizophrenia as well as dementia, bipolar disorder, obsessive compulsive disorder (OCD), panic disorder, phobias, acute stress disorder, adjustment disorder, agoraphobia without history of panic disorder, alcohol dependence (alcoholism), amphetamine dependence, brief psychotic disorder, cannabis dependence, cocaine dependence, cyclothymic disorder, delirium, delusional disorder, dysthymic disorder, generalized anxiety disorder, hallucinogen dependence, major depressive disorder, nicotine dependence, opioid dependence, paranoid personality disorder, Parkinson's disease, schizoaffective disorder, schizoid personality disorder, schizophreniform disorder, schizotypal personality disorder, sedative dependence, shared psychotic disorder, smoking dependence and social phobia.

In the present application, the terms "microRNA", "miRNA" and "miR" are used interchangeably to refer to a class of small approximately 20-25 nt long non-coding RNA molecules. They play important roles in the regulation of target genes through sequence-specific hybridization to the 3' untranslated region (UTR) of messenger RNAs (mRNA) to repress their translation or regulate degradation (Griffiths-Jones Nucleic Acids Research, 2006, 34, Database issue: D140-D144; Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28; all of which are incorporated herein by reference in their entirety). Most miRNAs are transcribed by RNA polymerase II from intergenic, intronic or polycistronic loci to long primary transcripts, called pri-miRNAs. vPri-miR-NAs are processed sequentially first in the nucleus (usually by the Drosha-DGCR8 complex) to approximately 70-100 nt pre-miRNA hairpin structures and then in the cytoplasm by the Dicer (ribonuclease III-like nuclease enzyme)-TRBP complex to approximately 2-25 nt miRNA duplexes (van Rooij and Kauppinen, EMBO Mol Med., 2014, 6(7): 851-864, which is incorporated herein by reference in its entirety). In the cytoplasm, miRNA duplexes are incorporated into an Argonaute protein-containing miRNA-induced silencing complex (miRISC), followed by unwinding of the duplex and retention of the mature miRNA strand in miRISC, while the complementary strand is released and degraded (van Rooij and Kauppinen, EMBO Mol Med., 2014, 6(7): 851-864, which is incorporated herein by reference in its entirety). miRNAs guide the miRISC to target mRNAs by base pairing imperfectly with their 3'-UTRs, leading to translational repression and/or degradation of the mRNA targets. The miRNA target sites, located in the 3'UTR of mRNAs, are often imperfectly matched to the miRNA sequence. Frequently, one miRNA can target multiple mRNAs and one mRNA can be regulated by multiple miRNAs targeting different regions of the 3' UTR. The 5' region of miRNA, also known as the "seed" region (nt 2-7), is the most critical sequence for targeting and function. Unless otherwise noted, the name of a specific miRNA refers to a mature miRNA sequence. Under current nomenclature rules, human miRNAs are preceded with the prefix "hsa-" (i.e., an abbreviation for *Homo sapiens*). Throughout the specification and figures the hsa- prefix may be dropped for purposes of abbreviation, thus, for example, "hsa-miR-382-3p" and "miR-382-3p" would represent the same RNA sequence.

In some embodiments, the present disclosure relates to miR-382-3p and/or miR-674-3p. The sequence of the mature human miR-382-3p is 5' AAUCAUU-CACGGACAACACUU 3' (SEQ ID NO: 1), which is encoded by human mir-382 gene (UAC-UUGAAGAGAAGUUGUUCGUGGUGGAUUCGC-UUUACUUAUGACGAAUCAUUC ACGGACAACAC-UUUUUUCAGUA, SEQ ID NO: 4). The sequence of the mature mouse miR-382-3p is 5' UCAUU-CACGGACAACACUUUUU 3' (SEQ ID NO: 2), which is encoded by mouse mir-382 gene (UAC-UUGAAGAGAAGUUGUUCGUGGUGGAUUCGC-UUUACUUGUGACGAAUCAUUC ACGGACAACAC-UUUUUUCAGUA, SEQ ID NO: 5). The sequence of the mature mouse miR-674-3p is 5' CACAGCUCCCAU-CUCAGAACAA (SEQ ID NO: 3), which is encoded by mouse mir-674 gene (GGCCUAGUCAUCACCCUGAGC-CUUGCACUGAGAUGGGAGUGGUGUAAGGCUCAG GUAUGCACAGCUCCCAUCUCAGAACAAGG-CUCGGGUGUGCUCAGCU, SEQ ID NO: 6).

As defined herein, the term "functional derivative" of a miRNA refers to a miRNA that has less than 100% identity to a corresponding wild-type miRNA and possesses one or more biological activities of the corresponding wild-type miRNA. Examples of such biological activities include, but are not limited to, inhibition of expression of a target RNA molecule (e g, inhibiting translation of a target mRNA molecule and/or modulating the stability of a target mRNA molecule) and inhibition of a cellular process associated therewith. These functional derivatives include species variants and variants that are the consequence of one or more mutations (e.g., a substitution, a deletion, an insertion) in a miRNA-encoding gene. In certain embodiments, the variant is at least about 70%, 75%, 80%, 85%, 90%, 95%, 98%, or 99% identical to a corresponding wild-type miRNA. Functional derivatives also encompass "functional fragments" of miRNA, i.e., portions of miRNA which are less than the full-length molecule (and their species and mutant variants) and that possess one or more biological activities of a corresponding wild-type miRNA. In certain embodiments, the biologically-active fragment is at least about 5, 7, 10, 12, 15, or 17 nucleotides in length.

As used herein, the term "miRNA mimic" refers to a double-stranded miRNA-like RNA fragment. Such miRNA mimic is designed to have its 5'-end bearing a partially complementary motif to the selected sequence in the 3'UTR unique to the target mRNA. Once introduced into cells, miRNA mimic, mimicking an endogenous miRNA, can bind to its target mRNA and inhibit its translation and/or modulate its stability. Unlike endogenous miRNAs, miR-mimics can be made to act in a gene-specific fashion by increasing the region of perfect complementarity with mRNA 3' UTR. Often, miRNA mimics are made to harbor chemical modifications to improve stability and/or cellular uptake (Rooij and Kauppinen, EMBO Mol Med., 2014, 6(7): 851-864, which is incorporated herein by reference in its entirety). In such double-stranded miRNA mimics, the strand identical to the miRNA of interest is the guide (antisense) strand, while the opposite (passenger or sense) strand is less stable and can be linked to a molecule, such as, e.g., cholesterol, to enhance cellular uptake. In addition, the passenger strand may contain chemical modifications to prevent RISC loading, while it is further left unmodified to ensure rapid degradation. Since the miRISC needs to recognize the guide strand as a miRNA, the chemical modifications that can be used for the guide strand are limited. For example, the 2'-fluoro (2'-F) modification helps to protect against exonucleases, hence making the guide strand more stable, while it does not interfere with RISC loading (Rooij and Kauppinen, EMBO Mol Med., 2014, 6(7): 851-864, which is incorporated herein by reference in its entirety).

The terms "vector", "expression vector", and "expression construct" are used interchangeably to refer to a composition of matter which can be used to deliver a nucleic acid of interest to the interior of a cell and mediate its expression within the cell. Most commonly used examples of vectors are autonomously replicating plasmids and viruses (such as, e.g., adenoviral vectors, adeno-associated virus vectors (AAV), lentiviral vectors, Sindbis virus vectors, etc.). An expression construct can be replicated in a living cell, or it can be made synthetically. In one embodiment, an expression vector comprises a promoter operably linked to a polynucleotide (e.g., a polynucleotide encoding miR-382-3p and/or miR-674-3p or its derivative or mimic) which promoter controls the initiation of transcription by RNA polymerase and expression of the polynucleotide. Typical promoters for mammalian cell expression include, e.g., SV40 early promoter, CMV immediate early promoter (see, e.g., U.S. Pat. Nos. 5,168,062 and 5,385,839, both of which are incorporated herein by reference in their entirety), mouse mammary tumor virus LTR promoter, adenovirus major late promoter (Ad MLP), herpes simplex virus promoter, murine metallothionein gene promoter, and U6 or H1 RNA pol III promoter. Non-limiting examples of promoters useful for expressing miR-382-3p and/or miR-674-3p in the methods of the present disclosure include, e.g., Synapsin promoter (neuron specific), CamKIIa promoter (specific for excitatory neurons), ubiquitin promoter, CAG promoter, CMV promoter, and β-actin promoter. These and other promoters can be obtained from commercially available plasmids, using techniques well known in the art. See, e.g., Sambrook et al., supra. Enhancer elements may be used in association with promoters to increase expression levels of the vectors. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777, which is incorporated herein by reference in its entirety, and elements derived from human CMV, as described in Boshart et al., Cell (1985) 41:521, which is incorporated herein by reference in its entirety, such as elements included in the CMV intron A sequence.

Typically, transcription terminator/polyadenylation signals will also be present in the expression vector. Examples of such sequences include, but are not limited to, those derived from SV40, as described in Sambrook et al., supra, as well as a bovine growth hormone terminator sequence (see, e.g., U.S. Pat. No. 5,122,458, which is incorporated herein by reference in its entirety). Additionally, 5'-UTR sequences can be placed adjacent to the coding sequence in order to enhance expression of the same. Such sequences include UTRs which include, e.g., an Internal Ribosome Entry Site (IRES) present in the leader sequences of picornaviruses such as the encephalomyocarditis virus (EMCV) UTR (fang et al. J. Virol. (1989) 63:1651-1660, which is incorporated herein by reference in its entirety). Other useful picornavirus UTR sequences include, e.g., the polio leader sequence, hepatitis A virus leader and the hepatitis C IRES.

In certain embodiments of the disclosure, the cells containing nucleic acid constructs of the present disclosure may be identified in vitro or in vivo by including a marker in the expression vector. Such markers would confer an identifiable change to the cell permitting easy identification of cells containing the expression vector. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., green fluorescent protein (GFP), EGFP, or Dronpa), or immunologic markers can also be employed. Further examples of selectable markers are well known to one of skill in the art.

In the context of the present disclosure insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease. Within the meaning of the present disclosure, the term "treat" also encompasses preventing and/or reducing a positive symptom associated with schizophrenia or 22q11 DS, such as, e.g., hallucinations, delusions, disorganized thought, or psychosis.

As used herein the term "therapeutically effective" applied to dose or amount refers to that quantity of a compound or pharmaceutical composition that is sufficient to result in a desired activity (e.g., decrease in positive symptoms associated with schizophrenia and/or 22q11DS) upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like. An appropriate "effective" amount in any individual case may be determined by one of ordinary skill in the art using routine experimentation, based upon the information provided herein.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "combination" of a composition of the disclosure and at least a second pharmaceutically active ingredient means at least two, but any desired combination of compounds can be delivered simultaneously or sequentially (e.g., within a 24 hour period). It is contemplated that when used to treat various diseases, the compositions and methods of the present disclosure can be utilized with other therapeutic methods/agents suitable for the same or similar diseases. Such other therapeutic methods/agents can be co-administered (simultaneously or sequentially) to generate additive or synergistic effects. Suitable therapeutically effective dosages for each agent may be lowered due to the additive action or synergy.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

An "individual" or "subject" or "animal", as used herein, refers to humans, veterinary animals (e.g., cats, dogs, cows, horses, sheep, pigs, etc.) and experimental animal models of schizophrenia or 22q11 DS. In a preferred embodiment, the subject is a human.

The term "associated with" is used to encompass any correlation, co-occurrence and any cause-and-effect relationship.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean within an order of magnitude, preferably within 50%, more preferably within 20%, still more preferably within 10%, even more preferably within 5%, and most preferably within 1% of a given value or range. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It must be noted that, as used in this specification and the appended claims, the singular forms "a," "an" and "the" include plural referents unless the content clearly dictates otherwise.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, NY: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-

492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 428-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14.3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Therapeutic Methods

In one aspect, the present disclosure provides a method for treatment and/or prevention of a disease associated with ventricular enlargement in a subject in need thereof, the method comprising administering to the subject a therapeutically effective amount of an inhibitor of Drd1, wherein the inhibitor inhibits an activity or expression of Drd1 in ependymal cells of the subject.

In some embodiments, the inhibitor of Drd1 is selected from a compound listed in Table 1, or an analog, a derivative, or a combination thereof.

TABLE 1

| | | |
|---|---|---|
| Non-limiting Examples of Drd1 Inhibitors | | |
| Compound | CAS Number | Chemical Name |
| Olanzapine/samidorphan | — | 2-methyl-4-(4-methylpiperazin-1-yl)-5H-thieno[3,2-c][1,5]benzodiazepine/17-(Cyclopropylmethyl)-4,14-dihydroxy-6-oxomorphinan-3-carboxamide |
| Lu AF35700 | — | — |
| Olanzapine | 132539-06-1 | 2-methyl-4-(4-methylpiperazin-1-yl)-5H-thieno[3,2-c][1,5]benzodiazepine |
| Olanzapine/fluoxetine | 250603-12-4 | — |
| Ecopipam | 112108-01-7 | (6aS,13bR)-11-Chloro-7-methyl-6,6a,7,8,9,13b-hexahydro-5H-benzo[d]naphtho[2,1-b]azepin-12-ol |
| Olanzapine transdermal | 132539-06-1 | 2-Methyl-4-(4-methyl-1-piperazinyl)-10H-thieno[2,3-b][1,5]benzodiazepine |
| Olanzapine | 132539-06-1 | 2-Methyl-4-(4-methyl-1-piperazinyl)-10H-thieno[2,3-b][1,5]benzodiazepine |
| Olanzapine controlled-release | 132539-06-1 | 2-methyl-4-(4-methylpiperazin-1-yl)-5H-thieno[3,2-c][l,5]benzodiazepine |
| Dopamine D3 receptor antagonists | — | 2,4-di-tert-Butyl-6-[4-[3-(4,5-dimethyl-4H-1,2,4-triazol-3-ylthio)propyl]piperazin-1-yl]pyrimidine hydrochloride |
| Olanzapine | 132539-06-1 | 2-Methyl-4-(4-methyl-1-piperazinyl)-10H-thieno[2,3-b][1,5]benzodiazepine |
| A 69024 | 58939-37-0 | 1-(2-Bromo-4,5-dimethoxyphenyl)-1,2,3,4-tetrahydro-7-hydroxy-6-methoxy-2-methylisoquinoline |
| BTS 73947 | — | (+)-1-[1-(2-Chlorophenyl)cyclopropyl]-7-hydroxy-6-methoxy-2-methyl-1,2,3,4-tetrahydroisoquinoline |
| Olanzapine/ondansetron | — | — |
| ZD 3638 | 152352-44-8 | (−)-4-[2-(Ethylsulfinyl)pyridin-3-yl]-1-(9,10-methano-9,10-dihydroanthracen-9-ylmethyl)piperidin-4-ol |
| ADX 10061 | 128022-68-4 | (+)-5-(2,3-Dihydrobenzofuran-7-yl)-3-methyl-8-nitro-2,3,4,5-tetrahydro-1H-3-benzazepin-7-ol |
| SDZ GLC 756 | 149328-94-9 | (−)-(3R,4aR,10aR)-6-Hydroxy-1-methyl-3,-(2-pyridylsulfanylmethyl)-l,2,3,4,4a,5,10,10a-octahydrobenzo[g] quinoline hydrochloride |
| CEE 03320 | — | (+)-7-Chloro-1-(5-,6-dichloro-2,3-dihydrobenzofuran-7-yl)-8-hydroxy-3-methyl-2,3,4,5-tetrahydro-1H-3-benzazepine |
| Odapipam | 131796-63-9 | (+)-8-Chloro-7-hydroxy-3-methyl-5-(2,3-dihydrobenzofuran-7-yl)-2,3,4,5-tetrahydro-1H-3-benzazepine |
| QF 1003B | — | N-[(4-oxo-4,5,6,7-tetrahydrobenzo[b]furan-6-yl)methyl]-4-(p-fluorobenzoyl)piperidine |
| QF 1004B | — | N-[(4-Oxo-4,5,6,7-tetrahydrobenzo[b]furan-6-yl)methyl]-4-(6-fluorobenzisoxazol-3-yl)piperidine |
| BIMG 80 | 160418-78-0 | 5-Methoxy-3-[N-(4-(4-fluoro-phenyl)-4-oxo-butyl)-1,2,5,6-tetrahydro-pyridin-3-ylmethyl]-1H-indole |
| LE300 | — | 7-Methyl-6,7,8,9,14,15-hexahydro-5H-indolo[2,3-f][3]-benzazecine |
| SDZ PSD 958 | 149811-12-1 | (−)-(4aR,10aR)-4-(4-chloro-2-methylphenyl)-1-methyl-1,2,3,4,4a,10,10a-octahydrobenzo[g]quinoxalin-6-ol |
| JHSI 136 | — | 8-Chloro-3-[4-(dimethylamino)butyl]-5-phenyl-2,3,4,5-tetrahydro-1H-3-benzazepin-7-ol |
| JHSII 198 | | 3-[6-(Dimethylamino)hexyl]-8-hydroxy-1-phenyl-2,3,4,5-tetrahydro-1H-3-benzazepin-7-carbonitrile |

TABLE 1-continued

Non-limiting Examples of Drd1 Inhibitors

| Compound | CAS Number | Chemical Name |
|---|---|---|
| JHS 271 | 171285-53-3 | — |
| GMC 1169 | — | 2-(Trifluoromethanesulfonyloxy)-11-(4-methylpiperazino)-5H-dibenzo[b,e][1,4]diazepine |
| GMC 306 | — | 2-(Trifluoromethylsulfonyloxy)-11-(4-methyl-1-piperazinyl)dibenzo[b,f][1,4]thiazepine |
| GMC 283 | — | 2-(Trifluoromethylsulfonyloxy)-11-(4-methyl-1-piperazinyl)dibenz[b,f][1,4]oxazepine |
| GMC 6139 | — | 2-(Trifluoromethylsulfonyloxy)-8-chloro-11-(4-methyl-1-piperazinyl)-5H-dibenzo[b,e][1,4] diazepine |
| BW 737C89 | 139485-39-5 | 6-Chloro-1(S)-(2,5-dimethoxy-4-propylbenzyl)-7-hydroxy-2-methyl-1,2,3,4-tetrahydroisoquinoline |
| Berupipam | 150490-85-0 | S(+)-1-(5-Bromo-2,3-dihydrobenzofuran-7-yl)-7-chloro-8-hydroxy-3-methyl-2,3,4,5-tetrahydro-1H-3-benzazepine maleate (2:1) |
| RGH 2721 | 133882-36-7 | 8-[4,4-Bis(4-fluorophenyl)-3-butenyl]-3-methyl-4-methylene-1-oxa-3,8-diazaspiro[4.5]decan-2-one |
| ORG 10490 | 83507-03-3 | (Z)-2-Butenedioate 6,7,8,9-tetrahydro-7-methyl-5H-dibenz[b,i][1,6]oxazecine |
| SKF R 105058 | 125375-79-3 | Carbamic acid, ethyl-, 6-chloro-1-(4-(((ethylamino)carbonyl)oxy)phenyl)-2,3,4,5-tetrahydro-1H-3-benzazepine-7,8-diyl ester, (R)-[4-[(5R)-9-chloro-7,8-bis(ethylcarbamoyloxy)-2,3,4,5-tetrahydro-1H-3-benzazepin-5-yl]phenyl] N-ethylcarbamate |
| SCH23390 hydrochloride | — | — |
| SCH39166 hydrobromide (Ecopipam) | — | — |
| SKF83566 hydrobromide | — | — |

In a specific embodiment, the inhibitor of Drd1 is SCH23390.

In some embodiments, the inhibitor of Drd1 is blood-brain barrier (BBB) permeable.

Gene editing of the Drd1 gene in ependymal cells is also contemplated by the present disclosure. The Drd1 gene in ependymal cells may be modified such that the expression and/or function of Drd1 in the ependymal cells is reduced or eliminated. In some embodiments, the Drd1 gene in the ependymal cells are modified with a site-specific nuclease. The term "site-specific nuclease" as used herein refers to a nuclease capable of specifically recognizing and cleaving a nucleic acid (DNA or RNA) sequence. Suitable site-specific nucleases for use in the present disclosure include, but are not limited to, clustered regularly interspaced short palindromic repeats (CRISPR)/Cas nucleases, zinc finger nucleases (ZFNs), transcription activator-like effector nucleases (TALENs), Meganucleases, and the like. These site-specific nucleases may reduce or eliminate the expression and/or function of the Drd1 gene by partially knocking down its expression or entirely knocking out the gene.

In one aspect, the present disclosure provides a method for treatment and/or prevention of a disease associated with ventricular enlargement in a subject in need thereof, the method comprising administering to the subject a therapeutically effective amount of (i) miR-382-3p and/or miR-674-3p or a mimic or a functional derivative (including functional fragments) thereof, or (ii) a vector expressing miR-382-3p and/or miR-674-3p or mimic or functional derivative thereof, or (iii) an agent capable of increasing the level or activity of miR-382-3p and/or miR-674-3p.

In various embodiments, diseases associated with ventricular enlargement include, but are not limited to, schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging.

In one embodiment, miR-382-3p comprises the sequence AAUCAUUCACGGACAACACUU (SEQ ID NO: 1). In another embodiment, miR-382-3p comprises the sequence UCAUUCACGGACAACACUUUU (SEQ ID NO: 2). In one embodiment, miR-382-3p consists of the sequence AAUCAUUCACGGACAACACUU (SEQ ID NO: 1). In another embodiment, miR-382-3p consists of the sequence UCAUUCACGGACAACACUUUU (SEQ ID NO: 2). In one embodiment, miR-674-3p comprises the sequence CACAGCUCCCAUCUCAGAACAA (SEQ ID NO: 3). In one embodiment, miR-674-3p consists of the sequence CACAGCUCCCAUCUCAGAACAA (SEQ ID NO: 3).

In one embodiment, the sequence coding for miR-382-3p comprises the sequence UACUUGAAGAGAAGUUGUUCGUGGUGGAUUCGCUUUACUUAUGACGAAUCAUUC ACGGACAACACUUUUUCAGUA (SEQ ID NO: 4), or a sequence having at least 80%, 85%, 90%, 95%, 96%, 97%, 98% or 99% identity to SEQ ID NO: 4. In another embodiment, the sequence coding for miR-382-3p comprises the sequence UACUUGAAGAGAAGUUGUUCGUGGUGGAUUCGCUUUACUUGUGACGAAUCAUUC ACGGACAACACUUUUUCAGUA (SEQ ID NO: 5), or a sequence having at least 80%, 85%, 90%, 95%, 96%, 97%, 98% or 99% identity to SEQ ID NO: 5. In one embodiment, the sequence coding for miR-674-3p comprises the sequence GGCCUAGUCAUCACCCUGAGCCUUGCACUGAGAUGGGAGUGGUGUAAGGCUCAGG UAUGCACAGCUCCCAUCUCAGAACAAGGCUCGG- GUGUGCUCAGCU (SEQ ID NO: 6), or a sequence having at least 80%, 85%, 90%, 95%, 96%, 97%, 98% or 99% identity to SEQ ID NO: 6. It is to be understood that the sequence encoding for miR-382-3p or miR-674-3p may be DNA or RNA, or modified version thereof. A skilled artisan will recognize that in the case of DNA, the sequences will comprise thymines (T) in lieu of uracils (U) in the sequences described above.

The therapeutic methods of the disclosure encompass over-expressing miR-382-3p and/or miR-674-3p, functional derivatives thereof or miR-382-3p and/or miR-674-3p mimics, e.g., using viral constructs, or using sense-based oligonucleotides or modified-oligonucleotide mimics (e.g., technologies from miRNA Therapeutics and miRagen Therapeutics), or inhibiting negative or activating positive miRNA regulators (transcriptionally or at epigenetic level), etc.

The miR-382-3p and/or miR-674-3p can be expressed from recombinant viral vectors. The recombinant viral vectors of the disclosure comprise sequences encoding the miR-382-3p and/or miR-674-3p and any suitable promoter for expressing the RNA sequences. Typical promoters for mammalian cell expression include, e.g., SV40 early promoter, CMV immediate early promoter (see, e.g., U.S. Pat. Nos. 5,168,062 and 5,385,839), mouse mammary tumor virus LTR promoter, adenovirus major late promoter (Ad MLP), herpes simplex virus promoter, murine metallothionein gene promoter, and U6 or H1 RNA pol III promoter. Non-limiting examples of promoters useful for expressing miR-382-3p and/or miR-674-3p in the methods of the present disclosure include, e.g., Synapsin promoter (neuron specific), CamKIIa promoter (specific for excitatory neurons), ubiquitin promoter, CAG promoter, CMV promoter, and β-actin promoter. Cell-type- or tissue-specific promoters can be used to express miRNA to allow for cell type- or tissue-specific expression. For example, the recombinant viral vectors of the disclosure can comprise inducible or regulatable promoters for expression of the miR-382-3p and/or miR-674-3p in ependymal cells.

Any viral vector capable of accepting the coding sequences for the miR-382-3p and/or miR-674-3p can be used. For example, vectors derived from adenovirus (AV), adeno-associated virus (AAV), retroviruses (e.g., lentiviruses (LV), Rhabdoviruses, murine leukemia virus), alphavirus, vaccinia virus, Sindbis virus, herpes virus, and the like. The tropism of the viral vectors can be modified by pseudotyping the vectors with envelope proteins or other surface antigens from other viruses, or by substituting different viral capsid proteins, as appropriate. For example, lentiviral vectors of the disclosure can be pseudotyped with surface proteins from vesicular stomatitis virus (VSV), rabies, Ebola, Mokola, and the like. AAV vectors of the disclosure can be made to specifically target certain cells or tissues by engineering the vectors to express certain capsid protein serotypes. Currently, there are several AAV serotypes available that can be used for tissue enrichment based on natural tropism toward specific cell types and interaction between different cellular receptors and serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), J Virol 76:791801, which is incorporated herein by reference in its entirety. A method for constructing the recombinant AV vector, and a method for delivering the vector into target cells, are also described in Xia et al. (2002), Nat. Biotech. 20:1006-1010, which is incorporated herein by reference in its entirety. Suitable AAV vectors for expressing the miR-NAs, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. Nos. 5,252,479; 5,139,941; International Patent Application No. WO 94/13788; and International Patent Application No. WO 93/24641, all of which are incorporated herein by reference in their entirety.

Alternatively, the miR-382-3p and/or miR-674-3p can be expressed from recombinant circular or linear DNA plasmids using any suitable promoter, including inducible/regulatable promoters. In one embodiment, the miR-382-3p and/or miR-674-3p is expressed as RNA precursor molecules from a plasmid, and the precursor molecules are processed into the functional mature miR-382-3p and/or miR-674-3p by a suitable processing system, including, but not limited to, processing systems existing within the ependymal cells. Other suitable processing systems include, e.g., the in vitro *Drosophila* cell lysate system (e.g., as described in U.S. Published Patent Application No. 2002/0086356 to Tuschl et al., which is incorporated herein by reference in its entirety) and the *E. coli* RNase III system (e.g., as described in U.S. Published Patent Application No. 2004/0014113 to Yang et al., which is incorporated herein by reference in its entirety).

Selection of plasmids suitable for expressing miR-382-3p and/or miR-674-3p, methods for inserting nucleic acid sequences into the plasmid to express miR-382-3p and/or miR-674-3p, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, all of which are incorporated herein by reference in their entirety.

In one embodiment, a plasmid expressing the miR-382-3p and/or miR-674-3p comprises a sequence encoding a miRNA precursor RNA under the control of the CMV and/or β-actin (ubiquitous) promoter. In another embodiment, a plasmid expressing the miR-382-3p and/or miR-674-3p comprises a sequence encoding a miR precursor RNA under the control of a ubiquitous CAG promoter.

In the therapeutic methods of the disclosure, miR-382-3p and/or miR-674-3p, mimics and functional derivatives thereof or can be also administered directly. Such miR-382-3p and/or miR-674-3p, mimics and functional derivatives can be chemically synthesized or recombinantly produced using methods known in the art. In one embodiment, miR-NAs are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

In some embodiments of the disclosure, a synthetic miRNA contains one or more design elements. These design elements include, but are not limited to: (i) a replacement group for the phosphate or hydroxyl of the nucleotide at the 5' terminus of the complementary region; (ii) one or more sugar modifications. In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. In particular embodiments, the sugar modification is a 2'O-Me modification. In further embodiments, there is one or more sugar modifications in the first or last 2 to 4 residues of the complementary region or the first or last 4 to 6 residues of the complementary region. In a particular embodiment, miR-382-3p and/or miR-674-3p, mimics and functional derivatives are made resistant to degradation by nucleases, e.g., by incorporating one or more ribonucleotides that are modified at the 2'-position with fluoro, amino, alkyl, alkoxy, and O-allyl.

Delivery of miR-382-3p and/or miR-674-3p, mimics and functional derivatives thereof or an inhibitor of Drd1 can be enhanced by complexing with liposome nanoparticles, exosomes, polyethyleneimine, or atelocollagen (Rooij and Kauppinen, EMBO Mol Med., 2014, 6(7): 851-864, which is incorporated herein by reference in its entirety).

Liposomes can increase the blood half-life of the nucleic acids. Liposomes suitable for use in the disclosure can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, all of which are incorporated herein by reference in their entirety. The liposomes for use in the present methods can comprise a ligand molecule that targets the liposome to thalamic neurons. The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In one embodiment, a liposome of the disclosure comprises both opsonization-inhibition moieties and a ligand.

Opsonization-inhibiting moieties for use in preparing the liposomes of the disclosure are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, which is incorporated herein by reference in its entirety. Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; animated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive animation using Na(CN) BH3 and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects will efficiently accumulate these liposomes; see Gabizon, et al. (1988), Proc. Natl. Acad. Sci., USA, 18:6949-53, which is incorporated herein by reference in its entirety. In addition, the reduced uptake by the RES lowers the toxicity of stealth liposomes by preventing significant accumulation of the liposomes in the liver and spleen.

In certain embodiments of the disclosure, the liposome may be complexed with a hemagglutinating virus (HVJ). This has been shown to facilitate fusion with the cell membrane and promote cell entry of liposome-encapsulated nucleic acids (Kaneda et al., 1989, which is incorporated herein by reference in its entirety). In other embodiments, the liposome may be complexed or employed in conjunction with nuclear non-histone chromosomal proteins (HMG-I) (Kato et al., 1991, which is incorporated herein by reference in its entirety). In yet further embodiments, the liposome may be complexed or employed in conjunction with both HVJ and HMG-I. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Exosomes are nano-sized vesicles (30-120 nm in size) produced by many cell types, including dendritic cells (DC), B cells, T cells, mast cells, epithelial cells, and tumor cells. These vesicles are formed by inward budding of late endosomes and are then released to the extracellular environment upon fusion with the plasma membrane. Exosomes can be isolated from cells (e.g., by centrifugation) and loaded with miRNA using, e.g., lipofectamine or electroporation.

Other expression constructs which can be employed to deliver miR-382-3p and/or miR-674-3p or a mimic or a functional derivative thereof into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, which is incorporated herein by reference in its entirety).

miR-382-3p and/or miR-674-3p or a mimic or a functional derivative thereof can be also administered in combination with a cationic lipid. Examples of cationic lipids include, but are not limited to, lipofectin, DOTMA, DOPE, and DOTAP. The publication of WO/0071096 describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, all of which are incorporated herein by reference in their entirety. Methods used for forming particles are also disclosed in U.S. Pat. Nos. 5,844,107, 5,877,302, 6,008,336, 6,077,835, 5,972,901, 6,200,801, and 5,972,900, all of which are incorporated herein by reference in their entirety.

It is contemplated that when used to treat various diseases, the compositions and methods of the present disclosure can be combined with other therapeutic agents suitable for the same or similar diseases. Also, two or more embodiments of the disclosure may be also co-administered to generate additive or synergistic effects. When co-administered with a second therapeutic agent, the embodiment of the disclosure and the second therapeutic agent may be simultaneously or sequentially (in any order). Suitable therapeutically effective dosages for each agent may be lowered due to the additive action or synergy. As a non-limiting example, the disclosure can be combined with other therapies that decrease the symptoms of ventricular enlargement, e.g., antipsychotics.

In some embodiments of the therapeutic methods described herein, the method further comprises increasing the expression and/or activity of Dgcr8 in ependymal cells of the subjects. Expression and/or activity of Dgcr8 may be increased by methods such as supplying additional Dgcr8, upregulating Dgcr8 expression (e.g., with an activator of Dgcr8), and/or genetically correcting the Dgcr8 gene. The Dgcr8 gene may be genetically corrected using a site-specific nuclease such as clustered regularly interspaced short palindromic repeats (CRISPR)/Cas nucleases, zinc finger nucleases (ZFNs), transcription activator-like effector nucleases (TALENs), and Meganucleases. A donor sequence encoding the correct Dgcr8 gene is provided along with the site-specific nuclease.

Compositions and Methods of Administration

In some embodiments, the disclosure provides that inhibitor of Drd1 can be administered to the subject to inhibit an activity or expression of Drd1 in ependymal cells of the subjects suffering from a disease associated with ventricular enlargement (e.g., schizophrenia and/or 22q11 DS). The disclosure further provides that the inhibitor of Drd1 can be used as pharmaceutical compositions and can be optionally combined with other antipsychotics, therapeutic molecules and/or treatments. In certain embodiments, inhibitor of Drd1, is used before, during, and after antipsychotics in combination therapies for treating a disease associated with ventricular enlargement (e.g., schizophrenia and/or 22q11 DS).

In some embodiments, the disclosure provides that miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p can be administered to the subject to replenish the endogenous miR-382-3p and/or miR-674-3p that is down-regulated in ependymal cells of the subjects suffering from a disease associated with ventricular enlargement (e.g., schizophrenia and/or 22q11 DS). The disclosure further provides that the isolated miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p can be used as pharmaceutical compositions and can be optionally combined with other antipsychotics, therapeutic molecules and/or treatments. In certain embodiments, miR-382-3p and/or miR-674-3p, or a mimic or a functional derivative thereof, or a vector expressing the miR-382-3p and/or miR-674-3p or mimic or functional derivative thereof, or an agent capable of increasing the level or activity of miR-382-3p and/or miR-674-3p, is used before, during, and after antipsychotics in combination therapies for treating a disease associated with ventricular enlargement (e.g., schizophrenia and/or 22q11 DS).

In various embodiments of the compositions and methods described herein, diseases associated with ventricular enlargement include, but are not limited to, schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, and normal aging.

The disclosure encompasses any now known or later developed antipsychotics for treating a disease associated with ventricular enlargement (e.g., schizophrenia and/or 22q11 DS). As a non-limiting example, the antipsychotic may be haloperidol, clozapine, olanzapine, or an analog, a derivative, or a combination thereof.

miR-382-3p and/or miR-674-3p molecules or mimics or functional derivatives thereof can include one or more modifications (e.g., to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and LNA. Where the miRNA molecule is produced synthetically, or by in vitro transcription, a modified ribonucleoside may be introduced during synthesis or transcription. Non-limiting examples of modified base moieties include inosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2- thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Non-limiting examples of modified sugar moieties include arabinose, 2-fluoroarabinose, xylulose, and hexose. Modified miRNAs may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified miRNAs may also have sugar mimetics such as cyclobutyls or other carbocyclics in place of the pentofuranosyl group. Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with $CH_2$—NH—O—$CH_2$, $CH_2$—N($CH_3$)—O—$CH_2$, $CH_2$—O—N($CH_3$)—$CH_2$, $CH_2$—N ($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437, which is incorporated herein by reference in its entirety, describes heteroaromatic oligonucleoside linkages. Nitrogen linkers or groups containing nitrogen can also be used to prepare oligonucleotide mimics (U.S. Pat. Nos. 5,792,844 and 5,783,682, all of which are incorporated herein by reference in their entirety). U.S. Pat. No. 5,637,684, which is incorporated herein by reference in its entirety, describes phosphoramidate and phosphorothioamidate oligomeric compounds. Also envisioned are modified miRNA molecules having morpholino backbone structures in which the bases are linked to 6-membered morpholine rings, which are connected to other morpholine-linked bases via non-ionic phosphorodiamidate intersubunit linkages. Morpholino miRNAs are highly resistant to nucleases and have good targeting predictability (U.S. Pat. No. 5,034,506; Summerton, Biochim Biophys. Acta 1999; 1489: 141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220, all of which are incorporated herein by reference in their entirety). Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497, which is incorporated herein by reference in its entirety). In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752, all of which are incorporated herein by reference in their entirety). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability.

Modified miRNAs can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810, all of which are incorporated herein by reference in their entirety) or blood-brain barrier (see, e.g., PCT Publication No. WO 89/10134, which is incorporated herein by reference in its entirety), etc.

miR-382-3p and/or miR-674-3p or mimics or functional derivatives thereof used in the present disclosure can be synthesized by standard methods known in the art, e.g., by use of an automated synthesizer. Following chemical synthesis, miRNA molecules are deprotected and purified (e.g., by gel electrophoresis or HPLC). Alternatively, standard procedures may be used for in vitro transcription of miRNA from DNA templates carrying RNA polymerase promoter sequences (e.g., T7 or SP6 RNA polymerase promoter sequences). See, e.g., Donzé and Picard, Nucleic Acids Res. 2002; 30:e46; and Yu et al., Proc. Natl. Acad. Sci. USA 2002; 99:6047-6052, both of which are incorporated herein by reference in their entirety. miRNA molecules may be also formed within a cell by transcription of RNA from an expression construct introduced into the cell. The expression constructs for in vivo production of miRNA molecules comprise miRNA encoding sequences operably linked to elements necessary for the proper transcription of the miRNA encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The miRNA expression constructs can further comprise vector sequences that facilitate the cloning of the expression constructs. Standard vectors that may be used in practicing the current disclosure are known in the art (e.g., pSilencer 2.0-U6 vector, Ambion Inc., Austin, TX).

In some embodiments, miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, is formulated into a suitable pharmaceutical preparation such as, e.g., solution, suspension, tablet, dispersible tablet, pill, capsule, powder, sustained release formulation or elixir, for oral administration; sterile solution or suspension for parenteral administration; powdered or liquid spray, nose drops, a gel or ointment for intranasal administration; powdered or liquid spray for administration by inhalation; films for sublingual administration; patch for transdermal administration, etc. miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, can be formulated into pharmaceutical compositions using any of the techniques and procedures known in the art (see, e.g., Ansel Introduction to Pharmaceutical Dosage Forms, Fourth Edition 1985, 126, which is incorporated herein by reference in its entirety).

In the compositions, effective concentrations of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 is (are) mixed with a suitable pharmaceutical carrier or vehicle.

Pharmaceutically acceptable derivatives include acids, bases, enol ethers and esters, salts, esters, hydrates, solvates and prodrug forms. A suitable derivative is selected such that its pharmacokinetic properties are superior with respect to at least one characteristic to the corresponding parent agent. The miR-382-3p and/or miR-674-3p, or its mimics, or an inhibitor of Drd1 may be derivatized prior to formulation.

In one embodiment of the disclosure, compositions of the present disclosure are administered inside the ventricles of the subject. In a particular embodiment, the administration is by intracerebroventricular injection.

In one embodiment of the disclosure, miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 is administered intranasally. Compositions for intranasal administration can comprise one or more nasal delivery-enhancing agents. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity such as the brain) of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1. Enhancement of mucosal delivery can thus occur by any of a variety of mechanisms, for example by increasing the diffusion, transport, persistence or stability of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, enzyme inhibition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and arc further described hereafter.

The pharmaceutical compositions of the present disclosure can be administered intranasally as a powdered or liquid spray, nose drops, a gel or ointment, through a tube or catheter, by syringe, packtail, pledget or by submucosal infusion. The compositions for intranasal administration can be simple aqueous (e.g., saline) solutions. Alternatively, they can contain various additional ingredients which enhance stability and/or nasal delivery of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1. Such additional ingredients are well known in the art. Non-limiting examples of useful additional ingredients for enhancing nasal delivery include, e.g., (a) aggregation inhibitory agents (e.g., polyethylene glycol, dextran, diethylaminoethyl dextran, and carboxy methyl cellulose), (b) charge modifying agents, (c) pH control agents, (d) degradative enzyme inhibitors (e.g., amastatin and bestatin [see, e.g., O'Hagan et al., Pharm. Res. 1990, 7: 772-776 and WO 05/120551, both of which are incorporated herein by reference in their entirety]; pegylation with PEG molecules, preferably low molecular weight PEG molecules [e.g. 2 kDa; Lee et al., Calcif Tissue Int. 2003, 73: 545-549, which is incorporated herein by reference in its entirety]); (e) mucolytic or mucus clearing agents (e.g., n-acetyl-cysteine, propylgallate and cysteine methionine dimmers, chaotropes [see, e.g., WO 04/093917, which is incorporated herein by reference in its entirety]), (f) ciliostatic agents; (g) membrane penetration-enhancing agents, (h) modulatory agents of epithelial junction physiology, such as nitric oxide (NO) stimulators, chitosan, and chitosan derivatives; (i) vasodilator agents, (j) selective transport-enhancing agents, and (k) stabilizing delivery vehicles, carriers, supports or complex-forming agents. See, e.g., EP 037943, EP 094157, EP 173990, EP 214898, EP 215697, EP 327756, EP 490806, U.S. Pat. Nos. 4,476,116, 5,759,565, WO 04/093917 and WO 05/120551, all of which are incorporated herein by reference in their entirety.

The activity or physical stability of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 in aqueous solutions or lyophilized preparations can be enhanced by various additives such as, e.g., polyols (including sugars [e.g., sucrose and Ficoll 70]), amino acids, and various salts. For example, miR-382-3p and/or miR-674-3p or a mimic or a functional derivative thereof microparticles can be prepared by simply lyophilizing or spray drying a solution containing various stabilizing additives described above. A wide non-limiting range of suitable methods and anti-aggregation agents are available for incorporation within the compositions of the disclosure such as disclosed in WO 05/120551, Breslow et al. (J. Am. Chem. Soc. 1996; 118: 11678-11681), Breslow et al. (PNAS USA 1997; 94: 11156-11158), Breslow et al. (Tetrahedron Lett. 1998; 2887-2890), Zutshi et al. (Curr. Opin. Chem. Biol. 1998; 2: 62-66). Daugherty et al. (J. Am. Chem. Soc. 1999; 121: 4325-4333), Zutshi et al. (J. Am. Chem. Soc. 1997; 119: 484-4845), Ghosh et al. (Chem. Biol. 1997; 5: 439-445), Hamuro et al. (Angew. Chem. Int. Fd. Fngl. 1997; 36: 2680-2683), Alberg et al., Science 1993; 262: 248-250), Tauton et al. (J. Am. Chem. Soc. 1996; 118: 10412-10422), Park et al. (J. Am. Chem. Soc. 1999; 121:8-13), Prasanna et al. (Biochemistry 1998; 37:6883-6893), Tiley et al. (J. Am. Chem. Soc. 1997; 119: 7589-7590), Judice et al. (PNAS USA 1997; 94: 13426-13430), Fan et al. (J. Am. Chem. Soc. 1998; 120: 8893-8894), Gamboni et al. (Biochemistry 1998; 37: 12189-12194), all of which are incorporated herein by reference in their entirety.

Non-limiting examples of membrane penetration-enhancing agents useful in the intranasal compositions of the disclosure include, e.g., (i) a surfactant (e.g., Tween 80, Poloxamer 188, polysorbates; see also EP 490806, U.S. Pat. No. 5,759,565, and WO 04/093917, all of which are incorporated herein by reference in their entirety), (ii) a bile salt or bile salt derivative (e.g., unsaturated cyclic ureas and Transcutol). (iii) a phospholipid or fatty acid additive, mixed micelle, liposome, or carrier, (iv) an alcohol, (v) an enamine, (vi) a nitric oxide donor compound (e.g., S-nitroso-N-acetyl-DF-penicillamine, NOR 1, NOR4, which are preferably co-administered with an NO scavenger such as carboxy-PITO or doclofenac sodium), (vii) a long-chain amphipathic molecule (e.g., deacylmethyl sulfoxide, azone, sodium lauryl sulfate, oleic acid) (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodextrin or beta-cyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc., inclusive of their alkali metal or alkaline earth metal salts), (xv) an N-acetylamino acid or salt (thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, polyoxyethylencalkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like; mixed micelles; glycerol esters of acetoacetic acid (e.g., glyceryl-1,3-diacetoacetate or 1,2-isopropylideneglycerine-3-acetoacetate) and triglycerides (e.g., amylodextrin, Estaram 299, Miglyol 810); cyclodextrins and (3-cyclodextrin derivatives (e.g., 2-hydroxypropyl-p-cyclodextrin and heptakis (2,6-di-0-methyl-[3-cyclodextrin) which can be optionally formulated in an oleaginous base; and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts), as well as other penetration-promoting agents that are physiologically compatible for intranasal delivery. See, e.g., WO04/093917, WO05/120551 and Davis and Ilium (Clin. Pharmacokinet. 2003, 42: 1107-1128), all of which are incorporated herein by reference in their entirety.

Non-limiting examples of useful absorption enhancers include, e.g., surfactants, glycosides, cyclodextrin and gly-cols. Non-limiting examples of useful bioadhesive agents include, e.g., carbopol, cellulose agents, starch, dextran, and chitosan.

In various embodiments of the disclosure, miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 is combined with one or more of the nasal delivery-enhancing agents recited above. These nasal delivery-enhancing agents may be admixed, alone or together, with the nasal carrier and with miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, or otherwise combined therewith in a pharmaceutically acceptable formulation or delivery vehicle. For nasal delivery-enhancing agents to be of value within the disclosure, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the nasal mucosa with long term use.

The useful delivery volume of the intranasal pharmaceutical compositions of the disclosure is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml. A solid composition may comprise from 1 to 30 mg carrier per dosage, more particularly 4 to 20 mg.

The liquid compositions of the disclosure may be prepared by bringing into intimate admixture miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 in the liquid carrier optionally together with the further ingredients, additives and/or agents. Preferably the resulting mixture is then lyophilized and dissolved in water or aqueous saline for use in a liquid form according to the disclosure. The solid nasal composition of the disclosure may be prepared in conventional manner. miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 may be admixed with the carrier particles, e.g., a polymer base or cellulose product in conventional manner, optionally with further ingredients, additives and/or agents as indicated above e.g. a mucosal delivery enhancing agent or surfactant such as disclosed. miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p or an inhibitor of Drd1 may be in solution, e.g., an aqueous or alcoholic solution when being mixed with the carrier particles and the solvent evaporated, e.g., under freeze-drying or spray drying. Such drying may be effected under the conventional conditions. Alternatively, the mixture may be compacted or granulated and then be pulverized and/or sieved. If desired the particles may be coated. According to a preferred embodiment of the disclosure, the nasal composition is prepared by lyophilization. A homogeneous solution, preferably aqueous, containing miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 and optionally containing further ingredients, additives and/or agents as discussed above, is prepared and then submitted to lyophilization in analogy with known lyophilization procedures, and to subsequent drying. The resulting powder may then be dissolved in a liquid excipient or nasal carrier before administration, e.g., to reconstitute nasal drops, gel or spray. Alternatively it may be administered as such in the form of lyophilized powder or it may be mixed with further ingredients, additives and/or agents as discussed above. For example, a lyophilized powder comprising miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p or an inhibitor of Drd1 but free of any nasal carrier may be prepared and then admixed with the desired nasal carrier or mixture of nasal carriers.

The present disclosure encompasses any delivery device that is suitable for nasal administration of the compositions of the disclosure. Preferably, such means administers a metered dosage of the composition. The composition of the present disclosure may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-free sprays, compressed air nebulizers, metered-disc inhalers, insufflators and pressurized metered dose inhalers.

For administration of a liquid in drop form, compositions of the disclosure can be placed in a container provided with a conventional dropper/closure device, e.g., comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomizing device, e.g. in a pump-atomizer, or the like. The atomizing device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Krich Pfeiffer GmbH, Radolfzell, Germany (see U.S. Pat. Nos. 4,511,069, 4,778,810, 5,203,840, 5,860,567, 5,893,484, 6,227,415, and 6,364,166, all of which are incorporated herein by reference in their entirety. Additional aerosol delivery forms may include, e.g. compressed air-, jet-, ultrasonic-, and piezoelectric nebulizers.

Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., Biol. Pharm. Bull. 2001; 24: 1411-1416, both of which are incorporated herein by reference in their entirety.

If desired a powder or liquid may be filled into a soft or hard capsule or in a single dose device adapted for nasal administration. The powder may be sieved before filled into the capsules such as gelatin capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

Delivery devices are important not only for delivering miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, but also for providing an appropriate environment for storage. This would include protection from microbial contamination and chemical degradation. The device and formulation should be compatible so as to avoid potential leaching or adsorption.

The delivery device (or its packaging) can be optionally provided with a label and/or with instructions for use indicating that the composition should be used intranasally.

In another embodiment, the composition of the disclosure can be provided as a nasal insert having miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 dispersed therein. The insert may be retained in the naris, but flushed by the nasal mucus, and may be designed to release miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1 at the same place in the naris. Suitable nasal insert types include nasal plugs, tampons and the like, further examples of nasal inserts, their characteristics and preparation are described in HP 490806.

The compounds and compositions of the disclosure may further comprise agents, which facilitate delivery across the blood brain barrier (BBB). Non-limiting examples of such useful agents include, e.g., an implantable reservoir (Omaya reservoir), polysialation, functionalized nanocarriers (e.g., nanoparticles coated with transferrin or transferrin receptor [TR] antibodies), exosomes, liposomes (e.g., liposomes coated with targeting molecules such as antibodies, Trojan Horses Liposomes [THL]), antibodies (e.g., antibodies against transferrin receptor [TR] or insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, receptor-associated protein, apolipoprotein E, melanotransferrin/p97, etc.

In one embodiment, in order to enhance brain delivery of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, the patient is treated in a manner so as to increase the selective permeability of the blood-brain barrier (BBB). Treatments to selectively increase the permeability of the BBB in a patient include, but are not limited to, the administration of about 1 to about 1000 µg/kg body weight, preferably about 10 to about 100 µg/kg body weight, of IGF-I (e.g., as a bolus injection to a patient about 0.5 to 10 hours, preferably about 1 hour, before the inhibitor administration).

The amount of miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, administered and the regimen of administration depends on absorption, inactivation and excretion rates of the active agent, the physicochemical characteristics of the agent, the severity of the condition to be alleviated, the age, condition, body weight, sex and diet of the patient, the disease state, other medications administered, and other factors known to those of skill in the art. An effective amount to treat the disease would broadly range (e.g., between about 0.001 mg and about 2000 mg per kg body weight of the recipient per day), and may be administered as a single dose or divided doses.

It is to be further understood that for any particular subject, specific dosage regimens should be adjusted over time according to the individual need and the professional judgment of the person administering or supervising the administration of the compositions.

The compositions of the disclosure are intended to be administered by a suitable route, including by way of example and without limitation orally, parenterally (e.g., intravenously, subcutaneously, intramuscularly), intranasally, by inhalation, sublingually, and topically. miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, can be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection; subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the brain and/or within thalamic neurons), and/or via viral vector (e.g., AAV and/or lentiviral vector) mediated delivery.

The compositions are in liquid, semi-liquid or solid form and are formulated in a manner suitable for each route of administration.

Solutions or suspensions can include any of the following components, in any combination: a sterile diluent, including by way of example without limitation, water for injection, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN®80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975, which is incorporated by reference in its entirety). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545, all of which are incorporated herein by reference in their entirety. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603, both of which are incorporated herein by reference in their entirety. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, poly-ethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aque-ous alcoholic solutions including a pharmaceutically accept-able acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenyl-salicylate, waxes and cellulose acetate phthalate.

Parenteral administration generally characterized by injection, either subcutaneously, intramuscularly or intrave-nously, is also contemplated herein. Injectables can be prepared in conventional forms, either as liquid solutions or suspensions, solid forms suitable for solution or suspension in liquid prior to injection, or as emulsions. Suitable excipi-ents include, by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buff-ering agents, stabilizers, solubility enhancers, and other such agents, such as, for example, sodium acetate, sorbitan mono-laurate, triethanolamine oleate and cyclodextrins.

Implantation of a slow-release or sustained-release sys-tem, such that a constant level of dosage is maintained (e.g., U.S. Pat. No. 3,710,795) is also contemplated herein. Briefly, an inhibitor of Nt5e or AIR is dispersed in a solid inner matrix (e.g., polymethylmethacrylate, polybutylmeth-acrylate, plasticized or unplasticized polyvinylchloride, plasticized nylon, plasticized polyethyleneterephthalate, natural rubber, polyisoprene, polyisobutylene, polybutadi-ene, polyethylene, ethylene-vinylacetate copolymers, sili-cone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/pro-pylene copolymers, ethylene/ethyl acrylate copolymers, eth-ylene/vinylacetate copolymers, silicone rubbers, polydim-ethyl siloxanes, neoprene rubber, chlorinated polyethylene, polyvinylchloride, vinylchloride copolymers with vinyl acetate, vinylidene chloride, ethylene and propylene, iono-mer polyethylene terephthalate, butyl rubber epichlorohy-drin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administra-tion as solutions, emulsions, and other mixtures or formu-lated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The sol-vent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For recon-stitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

miR-382-3p and/or miR-674-3p or a mimic or a func-tional derivative thereof, or a vector expressing the miR-382-3p and/or miR-674-3p or mimic or functional derivative thereof, or an agent capable of increasing the level or activity of miR-382-3p and/or miR-674-3p, or an inhibitor of Drd1, may be formulated as aerosols for application e.g., by inhalation or intranasally (e.g., as described in U.S. Pat. Nos. 4,044,126, 4,414,209, and 4,364,923, all of which are incorporated herein by reference in their entirety). These formulations can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be also formulated for local or topical application, such as for application to the skin and mucous membranes (e.g., intranasally), in the form of nasal solu-tions, gels, creams, and lotions.

Other routes of administration, such as transdermal patches are also contemplated herein. Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957, all of which are incorporated herein by reference in their entirety.

miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p may be packaged as articles of manufacture containing packaging material and a label that indicates that miR-382-3p and/or miR-674-3p or a mimic or a functional derivative thereof, or a vector expressing the miR-382-3p and/or miR-674-3p or mimic or functional derivative thereof, or an agent capable of increasing the level or activity of miR-382-3p and/or miR-674-3p, or pharmaceutically acceptable derivative thereof, are used for replenish miR-382-3p and/or miR-674-3p in ependymal cells for rescue abnormal function of ependymal cells, so as to treat a disease associated with ventricular enlargement such as schizophrenia and/or 22q11 DS.

In one embodiment of any of the above compositions, the composition further comprises an activator of Dcgr8, including an activator of the expression of Dcgr8, now known or later discovered.

In various embodiments, administration of a composition of the present disclosure results in a decrease in ventricular enlargement. The brain ventricles may include lateral ventricles and/or third ventricle. In various embodiments, administration of a composition of the present disclosure results in an increase in ciliary beating on ependymal cells lining the walls of lateral ventricles.

In various embodiments, administration of a composition of the present disclosure results in a decrease of Drd1 expression and/or function in ependymal cells lining the walls of ventricles of the subject. In various embodiments, administration of a composition of the present disclosure results in an increase in the level of miR-382-3p and/or miR-674-3p in ependymal cells lining the walls of ventricles of the subject.

In some embodiments, the subject receiving a composition of the present disclosure has an increased size of brain ventricles as compared to a control. The brain ventricles may include lateral ventricles and/or third ventricle. In some embodiments, the subject receiving a composition of the present disclosure has a decreased ciliary beating on ependymal cells lining the walls of lateral ventricles as compared to a control. In some embodiments, the subject receiving a composition of the present disclosure has an increased Drd1 expression and/or function in ependymal cells lining the walls of ventricles as compared to a control. In some embodiments, the subject receiving a composition of the present disclosure has a decreased level of miR-382-3p and/or miR-674-3p in ependymal cells lining the walls of ventricles as compared to a control. The control may be a predetermined standard, or the size/level in a healthy age- and gender-matched subject, or an average value for several such subjects.

Diagnostic Methods

In some aspects, the disclosure provides methods for diagnosing a disease associated with ventricular enlargement and/or determining efficacy of a treatment for such a disease. The disease associated with ventricular enlargement include but are not limited to schizophrenia, 22q11DS, Alzheimer's disease, Parkinson's disease, vascular dementia, age-dependent ventriculomegaly, spontaneous ventriculomegaly, hydrocephalus, primary ciliary dyskinesia, and normal aging.

In one aspect, the disclosure provides a method for determining efficacy of a treatment for a disease associated with ventricular enlargement in a subject, the method comprising:

(a) determining the level of miR-382-3p and/or miR-674-3p in ependymal cells, or a bodily fluid sample (e.g., CSF or blood) obtained from the subject before the treatment, (b) determining the level of miR-382-3p and/or miR-674-3p in ependymal cells, or a bodily fluid sample (e.g., CSF or blood) obtained from the subject after the treatment, (c) comparing the levels determined in steps (a) and (b), and (d) determining that the treatment is effective if the level of miR-382-3p and/or miR-674-3p in ependymal cells, or a bodily fluid sample (e.g., CSF or blood) from the subject has increased after the treatment.

In another aspect, the disclosure provides a method for determining the likelihood of developing a disease associated with ventricular enlargement in a subject, the method comprising:

(a) determining the level of miR-382-3p and/or miR-674-3p in ependymal cells or in a bodily fluid sample (e.g., CSF or blood) obtained from the subject, (b) comparing the level determined in step (a) to a control level, and (c) determining that the subject is at risk of developing a disease associated with ventricular enlargement if the level of miR-382-3p and/or miR-674-3p in ependymal cells or in the bodily fluid sample (e.g., CSF or blood) obtained from the subject is lower than the control level.

In yet another aspect, the disclosure provides a method for determining the likelihood of developing a disease associated with ventricular enlargement in a subject, the method comprising:

(a) determining one or more of the following: i) the presence of one or more mutations in Dgcr8 gene, ii) the Dgcr8 mRNA or protein level, and iii) the level of Drd1 or another dopamine receptor in motile cilia in ependymal cells, or in a bodily fluid sample (e.g., CSF or blood) obtained from the subject, (b) comparing the level determined in step (a) to a control level, and (c) determining that the subject is at risk of developing a disease associated with ventricular enlargement if i) one or more mutations is present in Dgcr8 gene, ii) the Dgcr8 mRNA or protein level is decreased, and/or iii) the level of Drd1 or another dopamine receptor in motile cilia is increased in ependymal cells, or in a bodily fluid sample (e.g., CSF or blood) from the subject.

In some embodiments, diagnostic methods of the present disclosure may comprise determining the size of brain ventricles of the subject. The brain ventricles may include lateral ventricles and/or third ventricle.

In some embodiments, diagnostic methods of the present disclosure may comprise assessing ciliary beating on ependymal cells lining the walls of lateral ventricles of the subject. The increase in ciliary beating may be assessed by one or more of the methods selected from: a. measuring the average velocity of fluorescent microbead movement at the apical surface of ependymal cells; b. measuring motile cilia beating frequency (CBF) by linescan imaging; and c. measuring ependymal motile cilia beating frequency (CBF) by 2-photon imaging at the surface of LV walls.

Diagnostic methods of the present disclosure may comprise determining Dgcr8 or Drd1 expression and/or activity in ependymal cells of the subject. The level of Dgcr8 or Drd1 may be determined by methods such as hybridization (including protein and nucleic acid hybridization assays, e.g., ELISA, Western blotting, Northern blotting, Southern blotting), array-based assays, PCR-based assays (e.g., qPCR), and sequencing. Diagnostic methods of the present disclosure may further comprise determining the expression and/or activity of another dopamine receptor in motile cilia in ependymal cells of the subject. The level of Drd1 or another dopamine receptor in motile cilia may be determined by methods such as immunostaining of the LV wall or measuring intracellular cAMP in the LV wall.

In the diagnostic methods of the disclosure, the level of 382-3p and/or miR-674-3p, the presence of one or more mutations in Dgcr8 gene, the Dgcr8 mRNA or protein level, or the level of Drd1 or another dopamine receptor is measured in a biological sample obtained from the subject. For example, a brain tissue sample can be removed from the subject, and ependymal cells can be isolated by standard techniques. Alternatively, a bodily fluid sample can be used. Non-limiting examples of useful bodily fluids for use in the diagnostic methods of the disclosure include, e.g., blood, urine, saliva, CSF. The blood sample may comprise whole blood, blood lymphocytes, peripheral blood mononuclear cells (PBMCs), blood plasma, or blood serum. The identification of miRNA expression in the blood sample will typically take place ex vivo, but the present disclosure also contemplates in vivo testing.

A corresponding control sample can be obtained from a healthy age- and gender-matched subject or a population of such healthy subjects. The control sample is then processed along with the sample from the subject, so that the levels of miR-382-3p and/or miR-674-3p, the presence of one or more mutations in Dgcr8 gene, the Dgcr8 mRNA or protein level, or the level of Drd1 or another dopamine receptor in the subject's sample can be compared to the corresponding values from the control sample. A reference miRNA or gene expression standard for the biological sample can also be used as a control.

The level of miR-382-3p and/or miR-674-3p in a sample can be measured using any technique that is suitable for detecting RNA levels in a biological sample. Suitable techniques include hybridization (e.g., Northern blot analysis, in situ hybridization), array-based assays, PCR-based assays, and sequencing. Array-based assays include, e.g., commercial arrays from Agilent, Exiqon, Affymetrix or custom-designed two-color arrays with a common reference (e.g., a specific quantity of 'artificial' miRNA for all probes on the chip or a specific sample such as, e.g., large batches of RNA isolated from patient blood, etc), or solution hybridization assays such as Ambion mirVana miRNA Detection Kit). Sequencing methods include, e.g., direct sequencing by one of the next generation sequencing technologies (e.g., Helicos small RNA sequencing, miRNA BeadArray (Illumina), Roche 454 (FLX-Titanium), and ABI SOLiD). For review of additional applicable techniques see, e.g., Chen et al., BMC Genomics, 2009, 10:407; Kong et al., J Cell Physiol. 2009; 218:22-25, both of which are incorporated herein by reference in their entirety.

In a particular embodiment, the level of at least one miR-382-3p and/or miR-674-3p is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, which is incorporated herein by reference in its entirety.

Suitable probes for Northern blot hybridization of miR-382-3p and/or miR-674-3p can be produced from the nucleic acid sequences provided in the figures and include, but are not limited to, probes having at least about 70%, 75%, 80%, 85%, 90%, 95%, 96%, 97%, 98%, 99% or complete complementarity to miR-382-3p and/or miR-674-3p. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, which is incorporated herein by reference in its entirety.

For example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)de-oxyuridine triphosphate, into the probe molecule. The biotinylyated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. Suitable probes for in situ hybridization of a given miRNA can be produced from the nucleic acid sequences, and include, but are not limited to, probes having at least about 70%, 75%, 80%, 85%, 90%, 95%, 96%, 97%, 98%, 99% or complete complementarity to a miRNA of interest, as described above.

The relative number of miRNA molecules in cells can also be determined by reverse transcription of miRNA, followed by amplification of the reverse-transcribed transcripts by polymerase chain reaction (RT-PCR). Non-limiting examples of useful commercial RT-PCR assays include Taqman miRNA assays (stem-loop assays; Applied Biosystems) and LNA-based miRNA PCR assays (poly-A-based assays; Exiqon) or quantitative RT-PCR based array method (qPCR-array). Other methods of amplification include ligase chain reaction (LCR), transcription-mediated amplification (TMA), strand displacement amplification (SDA) and nucleic acid sequence based amplification (NASBA).

The levels of miRNA can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

Useful methods of miRNA isolation and purification include, e.g., Qiazol or Trizol extraction or the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), concentration and purification on anion-exchangers, magnetic beads covered by RNA-binding substances, or adsorption of certain miRNA on complementary oligonucleotides.

In some embodiments, miRNA degradation in patients' samples is reduced or eliminated. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecylsulphate (SDS), or a combination thereof. Air-exposure-related RNA degradation can be reduced, e.g., by storage of samples in an inert air environment, performing RNA extraction within 3-4 days from the time of sample collection to minimize air-related RNA degradation, or minimizing time to tissue fixation. Reducing miRNA degradation in samples is particularly important when sample storage and transportation is required prior to miRNA quantification.

Kits of the Invention

In conjunction with the above diagnostic methods, the present disclosure also provides various kits comprising primers and/or probes specific for miR-382-3p and/or miR-674-3p. The kits of the disclosure can be useful, e.g., for diagnosing a disease associated with ventricular enlargement or for determining efficacy of a treatment for a disease associated with ventricular enlargement. The disease associated with ventricular enlargement may be schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, or normal aging.

A kit of the disclosure can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Materials and Methods

Animals. Both male and female mice (2-9 months old) were used for all experiments. The generation of Df(16)1/+, Dgcr8$^{+/-}$, Arl13b$^{eGFP}$, Foxj1$^{Cre}$, and Ai14 mouse lines has been reported previously (Delling et al., 2013; Earls et al., 2012; Lindsay et al., 1999; Madisen et al., 2010; Zhang et al., 2007). Df(16)1/+ and Dgcr8$^{+/-}$ mouse strains were back-crossed onto the C57BL/6J genetic background for at least 10 generations. The care and use of animals were reviewed and approved by the St. Jude Children's Research Hospital (St. Jude) Institutional Animal Care and Use Committee.

Magnetic Resonance Imaging. The animal MRI study was performed using a 7 T Bruker ClinScan system (Bruker BioSpin MRI GmbH, Germany) equipped with a 12S gradient coil. A mouse head volume coil (Bruker BioSpin) was used. Animals were anesthetized and maintained with 1.5%-2% isoflurane during the experiments. Transverse T2-weighted turbo spin echo images were acquired for volume measurements (Repetition time/Echo time=3660/50 ms, field of view=25×25 mm, matrix=320×320 pixels, number of averages=1, thickness=0.4 mm, scan time=11.5 min).

Transmission and Scanning Electron Microscopy. For TEM, 8-month-old WT and Dgcr8$^{+/-}$ mice were perfused in 4% paraformaldehyde and postfixed in 2.5% glutaraldehyde in 0.1 M sodium cacodylate buffer (Tousimis Research Corp, Rockville, MD or Electron Microscopy Sciences, Hatfield, PA). The samples were postfixed in 2% osmium tetroxide and dehydrated via a graded series of alcohol baths, cleared in propylene oxide, embedded in epon araldite, and polymerized overnight at 70° C. Sections (70-nm thick) were cut on a Leica Ultracut E. The unstained sections were imaged on a JEOL 1200 EX transmission electron microscope with an AMT 2K digital camera.

For scanning electron microscopy (SEM), the brains were perfused with super-reagent perfusion wash and super-reagent perfusion fixation (Electron Microscopy Sciences, Hatfield, PA). Freshly collected brains were dissected and fixed with 2.5% glutaraldehyde in 0.1 M sodium cacodylate buffer, pH 7.35 (Tousimis Research Corp, Rockville, MD) and 2% osmium tetroxide, pH 7.35, in 0.1 M sodium cacodylate buffer (Electron Microscopy Sciences) before dehydration in an ethanol series and critically point dried (Tousimis Sandai 790, Tousimis Research Corp), Samples were mounted, coated with gold/palladium, and imaged using a JEOL 7000 field emission gun scanning electron microscope.

Immunogold labeling. Mice were perfused with 0.1 M phosphate buffer (pH 7.3) containing 4% paraformaldehyde and 0.1% glutaraldehyde; their brains were then removed and immersed in the same fixative. Brain slices prepared using a vibratome were contrasted with tannic acid and uranyl acetate in 0.1 M sodium acetate, dehydrated in series of solutions with increasing concentrations of ethanol to 100%, infiltrated with resin/ethanol mixtures, and embedded into a modified formulation of Spurr's resin (Ann Ellis, 2006). The embedded brain slices were sectioned at 80-nm thickness and placed on nickel grids for immunolabeling. The brain sections were sequentially treated with 50 mM glycine in 10 mM PBS (pH 7.4); a blocking solution composed of 5% bovine serum albumin (BSA), 5% normal serum, and 0.1% cold water fish skin gelatin in PBS; and 0.1% BSA-c (Aurion) in PBS. The sections were incubated overnight at 4° C. with anti-Drd1 antibody (Abcam, ab20066, 1:5000) diluted in 0.1% BSA-c in PBS. After washing with 0.1% BSA-c in PBS, the brain sections were incubated with 12-nm Colloidal Gold AffiniPure donkey anti-rabbit IgG (Jackson Immuno Research, 711-205-152, 1:20) diluted in 0.1% BSA-c in PBS for 2 hours at room temperature and washed sequentially with 0.1% BSA-c in PBS, PBS, and water, then allowed to air dry. Samples were examined at 80 kV on an F20 transmission electron microscope (Thermo Fisher Scientific) equipped with an AMT camera system.

Microbeads-Based Ependymal Flow Assay. The LV walls were dissected and pinned in a dish with L-15 Leibovitz media (Thermo Fisher Scientific) at room temperature. Latex beads (1-µm diameter, 5 nL; Sigma-Aldrich, L2778) were released over the dorsal surface of the lateral wall by using a stereotactic injector. Bead movements were recorded using a Rolera-XR high-speed digital camera and an Olympus U-CMAD3 fluorescence microscope using Q-Capture Pro7 imaging software (QImaging, Surrey, BC, Canada), with an acquisition rate of 20 frames/second. Three to five rounds of bead release and imaging were performed for each whole-mount to obtain optimal flow. Negative controls confirmed absent bead flow over the ventricular surface after a 5-minute incubation in 70% ethanol.

To trace fluorescent beads in an unbiased manner, a software toolkit was developed in MATLAB (Mathworks, Natwick, MA). In this approach, beads are detected via multiple-scale Laplacian of Gaussian (LoG) filters (Lowe and G., 2004) as follows:

$$h(i, j) = \frac{(i^2 + j^2 - 2\sigma^2)g(i, j)}{\sigma^4 \sum_m \sum_n g(m, n)},$$

where g(i,j) is a Gaussian (e−(i2+j2)/2σ2), i,j∈ [−[2σ], [2σ]], and σ is related to the radius of the bead by σ=r/√2. In practice, filter radii between 3 and 5 pixels are commonly used. Local optima are extracted from filter-response maps, and a sensitivity threshold is applied to remove weak detections. Next, a nonminima suppression technique discards weak, overlapping detections (Felzenszwalb et al., 2010). Then remaining beads are further pruned in a two-step refinement process: (1) an additional threshold on local maxima from a Gaussian heatmap generated using the spatial location of each detection combines nearby beads into single detections; (2) agglomerative clustering using the complete-linkage criterion over Chebychev distance removes beads that are stationary for too many frames in the image sequence (Jain et al., 1999). All thresholds are determined interactively by the user. After detection and refinement, the remaining candidate beads are tracked through time using a Kalman filter with a constant-velocity model (Comaniciu et al., 2003). The initial variance of the detections is assumed to be small (i.e., the LoG filtering/refinement process yields strong detections) and instead the motion error of the filter is increased (i.e., the prediction of the Kalman filter is more likely to have an error than is the detection filter due to irregular bead movement and time between image captures). There are additional thresholds on the expected time that a bead is visible in the image (on average); this helps to further prune tracks that are biologically unlikely. The software for microbead tracing is available at: https://github.com/dnbornl/beadtracking.

Ex Vivo Ciliary Beating Frequency Measurements. For ex vivo measurement of CBF, coronal brain sections (300-µm) were collected in L-15 Leibovitz media (Thermo Fisher Scientific) and placed in 37° C., 95%/5% O$_2$/CO$_2$ chamber. Image sequences of CBF were acquired by linescan analysis using an LD C-Apochromat 40× objective water-immersion lens (1.1 NA) in LSM780 confocal microscope (Zeiss AxioObserver). Slices were scanned through a line perpendicular to the axis of the cilia in the Xt mode along this line with an acquisition rate of 529 frames/second (512×1 frame size, 1.89-ms scan time, 5,000 cycles). Transmitted DIC and fluorescence emitted by GFP or Alexa Fluor 488 were collected with a 488- to 568-nm bandpass filter. Fluorescence excitation and transmitted illumination were provided by a 488-nm argon gas laser. The Drd1 agonist (SKF81297, 10 µM; Tocris, Minneapolis, MN) and antagonist (SCH23390, 10 µM; Tocris) were bath-applied once per slice. Five minutes after the agonist or antagonist was applied, the CBF was measured.

In Vivo Ciliary Beating Frequency Measurements. For in vivo measurement of CBF, Dgcr8$^{+/-}$;Arl13b$^{eGFP}$ and Dgcr8$^{+/+}$,Arl13b$^{eGFP}$ mice of both sexes (aged 6-8 months) were anesthetized with intraperitoneal (IP) injection of ketamine/xylazine (100 mg/kg and 10 mg/kg, respectively) prior to surgery. Toe pinch reflexes were monitored during the procedure, and anesthesia was boosted with IP injection of ketamine (50 mg/kg) when needed. Mice were clamped in position by a headpost; the skin overlaying the left and right frontal and parietal skull bones was removed, and the surface of the skull was cleaned and dried. Two holes (7-mm each) were made in the right frontal skull bone for the placement of stainless steel screws. An aluminum headpost was firmly fastened onto the screws using cyanoacrylate and dental cement. The mouse's head was positioned at a 45° angle with the left side up. The left temporalis muscle overlying the squamosal bone was then removed and a craniotomy was performed on the left skull using a 0.5-mm drill burr, beginning at the bregma and approximately 1 mm to the left of the sagittal suture, continuing 5 mm posteriorly down the left parietal bone. The window continued laterally along the left parietal bone and approximately 2.5 mm down the side of the left squamosal bone. The dura was then removed from the exposed brain surface, and all exposed cortex was aspirated by suction. Blood was constantly removed by aspiration and flushing with saline-15 Leibovitz media until bleeding ceased. With sufficient cortex removed, part of the dorsal and descending hippocampus was exposed, and the LV was visible as an apparent gap between the removed cortex and the hippocampal surface. The mouse was then transferred to the two-photon microscope stage, where it was held firmly via headpost clamp. The skull window was filled with 0.9% saline and positioned under a 25× water-immersion infrared objective (Olympus, 1.05 NA). GFP-positive cilia lining the left LV were imaged with 940-nm laser excitation. With a resonant image-scanning resolution of 512×512 pixels, regions of interest were chosen to provide a sampling rate of 90-120 Hz. Following the imaging session, mice were immediately euthanized without regaining consciousness. Captured images were stabilized for movement (breathing) artifacts using the Moco ImageJ plugin, and CBF rates were measured manually.

Quantitative RT-qPCR. Total RNA was isolated from the LV wall (200- to 300-μm-thick slice) using the mirVana microRNA Isolation Kit (Life Technologies, Carlsbad, CA). The iScript kit (Bio-Rad, Hercules, CA) was used to synthesize cDNA from mRNA, and the miRNA First-Strand cDNA Synthesis Kit (Agilent, Santa Clara, CA) was used to synthesize cDNA from mRNA. The qPCR was performed using SYBR Green (Life Technologies). The following forward primers were used for miRNA analysis: mmu-miR-153-5p (5'-TTTGTGACGTTGCAGCT-3', SEQ ID NO: 7), mmu-miR-382-3p (5'-TCATTCACGGACAACACTTTTT-3', SEQ ID NO: 8), and mmu-miR-674-3p (5'-CACAGCTCCCATCTCAGAACAA-3', SEQ ID NO: 9). The universal reverse primer specific to the sequence tag (miRNA First-Strand cDNA Synthesis Kit) was used. The following primers were used for mRNA analysis: Drd1 forward (5'-ATGGCTCCTAACACTTCTACCA-3', SEQ ID NO: 10), Drd1 reverse (5'-GGGTAT-TCCCTAAGAGAGTGGAC-3', SEQ ID NO: 11), Dgcr8 forward (5'-CCACGACCATCCTCAGACATTG-3', SEQ ID NO: 12), Dgcr8 reverse (5'-AT-GAAAATCTCCCCTCCCCACAGCC-3', SEQ ID NO: 13). The following loading controls were used: U6 snRNA forward (CGCTTCGGCAGCACATATAC, SEQ ID NO: 14) and U6 snRNA reverse (TTCACGAATTTGCGTGTCAT, SEQ ID NO: 15). Expression levels of Drd1, miR-153-5p, miR-382-3p, and miR-674-3p were normalized to the house-keeping gene U6 for each sample. Samples from each mouse were run in triplicate.

Generation of miRNA Overexpression Plasmids. To over-express the miRNAs of interest, recombinant plasmids were generated by cloning has-miR-30a chimeric hairpin including sequences of the miRNAs of interest into the 3UTR of GFP under the control of the CAG promoter by using a previously described strategy (Christensen et al., 2010; Chun et al., 2017). The following primers were used: miR-153-5p-1 (5'-GTACAGCTGTTGACAGT-GAGCGACTTTGTGACGTTGCAGCTTGTGAA-3', SEQ ID NO: 16), miR-153-5p-2 (5'-CCATCTGTGGCTT-CACAAGCTGCAACGTCACAAAGTCGCTCACTGT-CAACAGCT-3', SEQ ID NO: 17), miR-153-5p-3 (5'-GC-CACAGATGGAGCTGCAACGTCACAAAGCTGCCTAC TGCCTCGGAA-3', SEQ ID NO: 18), miR-15.3-5p-4 (5'-AGCTTTCCGAGGCAGTAGGCAGCTTTGTGACGTTG CAGCT-3', SEQ ID NO: 19), miR-382-3p-1 (5'-GTA-CAGCTGTTGACAGTGAGCGACTCATT-CACGGACAACACTTTTTTGTGAA-3', SEQ ID NO: 20), miR-382-3p-2 (5'-CCATCTGTGGCTT-CACAAAAAAGTGTTGTCCGTGAATGAGTCGCT-CACTGTCAACAG CT-3', SEQ ID NO: 21), miR-382-3p-3 (5'-GCCACAGATGGAAAAAGTGTTGTCCGTGAAT-GAGCTGCCTACTGCCTCGGAA-3', SEQ ID NO: 22), miR-382-3p-4 (5'-AGCTTTCCGAGGCAGTAGGCAGCT-CATTCACGGACAACACTTTTT-3', SEQ ID NO: 23), miR-674-3p-1 (5'-GTACAGCTGTTGACAGT-GAGCGACCACAGCTCCCATCTCAGAACAATGT-GAA-3', SEQ ID NO: 24), miR-674-3p-2 (5'-CCATCTGTGGCTTCACATTGTTCTGAGATGGGAGCT GTGGTCGCTCACTGTCAACAGC T-3', SEQ ID NO: 25), miR-674-3p-3 (5'-GCCACAGATGGTTGTTCT-GAGATGGGAGCTGTGGCTGCCTACTGCCTCGGAA-3', SEQ ID NO: 26), and miR-674-3p-4 (5'-AGCTTTCCGAGGCAGTAGGCAGCCACAGCTCCCAT CTCAGAACAA-3', SEQ ID NO: 27). Recombinant AAVs were generated at the St. Jude Vector Development and Production Core as described previously (Chun et al., 2017).

Generation of miRNA Sponge Constructs. The miR-382-3p and miR-674-3p sponges were generated as described previously (Chun et al., 2017). Six copies of the following sequences were inserted for the miR-382-3p sponge (TTGTTCTGAGATGGGAGCTGTG, SEQ ID NO: 28), the miR-674-3p sponge (TCATTCACGGACAACACTTTT, SEQ ID NO: 29), or the scrambled control (GACACTGT-GAGCGAAGACATA, SEQ ID NO: 30) into the 3'UTR of GFP under the control of the CAG promoter. Recombinant AAVs were generated at the St. Jude Vector Development and Production Core as described previously (Chun et al., 2017).

Generation of Drd1$^{\Delta 7bp}$ and Drd1$^{\Delta 13bp}$ mice. Drd1$^{\Delta 7bp}$ and Drd1$^{\Delta 13bp}$ mice were generated using the CRISPR/Cas9 approach. Briefly, C57BL/6J fertilized zygotes (Jackson Laboratories, Bar Harbor, ME) were cytoplasmically coinjected with 50 ng/μL sgRNA (Synthego), 100 ng/μL SpCas9 in vitro transcribed mRNA (Center for Advanced Genome Engineering at St. Jude), and 50 ng/μL ssODN donor (IDT). Founder mice were genotyped by targeted next-generation sequencing. The following editing construct sequences and relevant primers were used: mDrd1$^{\Delta 7bp}$-sgRNA (TAAT-GAGCTGTGCCTCATCG, SEQ ID NO: 31), mDrd1$^{\Delta 7bp}$.donor (AGTATCCTCTCT-TAAAAAAAAAAAAAAAAGCTCTTTAATGT-TAGTGGTAAACTAGCT AATGCCTCATCGTG-GAAGTATACACTTCTGTTGTTGGTGGGGGGAATAGA AGAACCC CTTCCC, SEQ ID NO: 32), mDrd1$^{\Delta 7bp}$.NGS.F including partial Illumina adaptors (upper case) (CACTCTTTCCCTACACGACGCTCTTCC-GATCTagtcacaggtcacagcagcccctcc, SEQ ID NO: 33), mDrd1$^{\Delta 7bp}$.NGS.R including partial Illumina adaptors (upper case) (GTGACTGGAGTTCAGACGTGTGCTCTTCC-GATCTactgttgcaataccccccacccgagg, SEQ ID NO: 34), mDrd1Δ13bp.sgRNA (CAGGATTAAGATGTGCATCG, SEQ ID NO: 35), mDrd1$^{Δ13bp}$.donor (TGCTT-GAAATGGCTTTCT-GAAACAAACAAATGACTGTCCAGGATTAA-GATGTGCATC
GAGAAAGTCACAGGTCACAGCAGCCCCTCCGA-TAGTTGGGCTCATCGCTGGTTCTTC ATCTGC, SEQ ID NO: 36), mDrd1$^{Δ13bp}$.NGS.F including partial Illumina adaptors (upper case) (CACTCTTTCCCTA-CACGACGCTCTTCCGATCTatggcagaggctttccccgaggcaa, SEQ ID NO: 37), mDrd1$^{Δ13bp}$.NGS.R including partial Illumina adaptors (upper case) (GTGACTGGAGTTCA-GACGTGTGCTCTTCCGATCTacaaaagtagcccctt-gagcagccg, SEQ ID NO: 38). Drd1$^{Δ7bp}$ and Drd1$^{Δ13bp}$ lines with corresponding deletions were established. The sequences are as below: for Drd1$^{Δ7bp}$, Drd1 (5'-TGGTAAACTAGCTAATGAGCTGTGCCTCATCGTG-GAAGTA-3', SEQ ID NO: 39) and Drd1$^{Δ7bp}$ (5'-TGGTAAACTAGCTAATG-------CCTCATCGTGGAAGTA-3', SEQ ID NO: 40), and for Drd1$^{Δ13bp}$, Drd1 (5'-GATGTGCATCGAGGTGAAT-GAGCTGTAAAGTCACAGGTCA-3', SEQ ID NO: 41) and Drd1$^{Δ13bp}$ (5'-GATGTGCATCGAG------------AAAGTCACAGGTCA-3', SEQ ID NO: 42).

Luciferase Assay. To test the effect of each miRNA on Drd1 expression, the 3'UTR of the Drd1 gene was cloned into the 3' end of the Renilla luciferase gene contained within the psiCHECK-2 vector (Promega, Madison, WI). The plasmids were transfected into HEK 293 cells (ATCC, CCL-3216) with control hsa-miR-30a, miR-153-5p, miR-382-3p, or the miR-647-3p OE plasmid. After 2 days in culture, Renilla and Firefly activities were measured using the dual-luciferase reporter assay (Promega) according to the manufacturer's instructions. The Renilla luciferase activity was normalized to Firefly luciferase activity.

Viral Infections and Surgery. For in vivo viral injections, young adult mice were anesthetized with isoflurane in pure oxygen (2%-3% for induction and 1.0%-1.5% for mainte-nance). Mouse heads were then fixed in a stereotaxic device. Viruses were injected with a metal cannula (33 gauge; Plastics One, Roanoke, VA). An incision was made in the scalp, and a small hole was drilled for the craniotomy. The following stereotaxic coordinates were used for in vivo injections: the intracerebroventricle (anterior-posterior, −0.22 mm; lateral, +1.0 mm; ventral, −2.0 mm). After injections, incisions were sutured and mice were allowed to recover before being returned to their holding cages. Experi-ments were performed approximately 3 weeks after AAV1 injections.

Western Blotting. Tissue from the LV wall (200- to 300-μm slice) was acutely dissected from the mouse brain and lysed in ice-cold RIPA buffer [50 mM Tris-HCl (pH 7.4), 1% NP-40, 0.25% sodium deoxycholate, 150 mM NaCl, and 1 mM EDTA] that included protease-inhibitor cocktail tab-lets (Roche, Indianapolis, IN). A total of 25 μg protein was loaded per lane. Sodium dodecyl sulfate/polyacrylamide gel electrophoresis, protein transfer to polyvinylidene difluoride membranes, and western blotting were performed using standard methods. The following primary antibodies were used: rabbit anti-DRD1 (Abcam, Cambridge, MA; ab40653, 1:500), rabbit anti-DRD2 (Abcam, ab85367, 1:500) and mouse anti-β-actin (Sigma-Aldrich, St. Louis, MO; A5316, 1:10,000). The following secondary antibodies were used: anti-rabbit (LI-COR Biosciences, Lincoln, NE; 926-68021, 1:15,000) and anti-mouse (LI-COR Biosciences, 926-

32212, 1:15,000) and antibodies conjugated to IR dye 680 or 800, respectively. Blots were imaged and quantified using the Odyssey CLx infrared imaging system (LI-COR Biosci-ences).

Histologic Analysis and Immunohistochemistry. Mice were deeply anesthetized and intracardially perfused with 4% paraformaldehyde in 0.1 mol/L phosphate buffer (pH 7.4), and brains were fixed overnight. Each brain was sliced (50 μm) coronally with a vibratome (Leica), and the sections including the LV wall were immunolabeled as previously described (Mirzadeh et al., 2010b). The following primary antibodies were used: DRD1 (Sigma-Aldrich, D2944, 1:200), DRD2 (Millipore, Burlington, MA; AB5084p, 1:200), acetylated tubulin (Sigma-Aldrich, T6793, 1:1000), γ-tubulin (Sigma-Aldrich, T5192, 1:1000), β-catenin (BD Transduction Lab, San Jose, CA; 610153, 1:500), GFP (Abcam, ab13970, 1:1000), cleaved caspase-3 (Cell Signal-ing, Danvers, MA; 9661S, 1:250), Ki67 (Abcam, ab15580, 1:500), BrdU (Abcam, ab6326, 1:200), doublecortin (Ab-cam, ab18723, 1:1000). Appropriate Alexa dye-conjugated secondary antibodies (Thermo Fisher Scientific, Waltham, MA; 1:1000) were used to detect primary antibody binding. DAPI (Invitrogen, Carlsbad, CA) was used as the nuclear counterstain. For cell proliferation in the SVZ or tracking neuronal migration from the SVZ to the olfactory bulb, BrdU (100 mg/kg) was injected three times at 2-hour intervals. Brains were collected the next day for SVZ analysis or 21 days later for neuronal migration analysis.

Super-Resolution Microscopy. Motile cilia in fixed corti-cal sections were imaged by structured illumination micros-copy (SIM) with a Zeiss ELYRA PS.1 super-resolution microscope (Carl Zeiss MicroImaging, Thornwood, NY) using a 63× oil objective lens with 1.4 NA at room tem-perature. Three orientation angles of the excitation grid were acquired for each Z plane, with Z spacing of 110 nm between planes. SIM processing was performed with the SIM analysis module of the Zen 2012 BLACK software (Carl Zeiss MicroImaging) and exported as tiff images.

Cerebrospinal Fluid Collet-Won and Analysis. For CSF collection, a glass micropipette was inserted into the cisterna magna of anesthetized mice. Collected samples were frozen at −80° C. until analysis. Osmolality was measured by freezing point depression (Advanced Instruments, Norwood, MA) in the Pathology Laboratory at St. Jude.

miRNA Microarray Analysis. Total RNA was isolated from the LV wall of 8-month-old WT and Dgcr8$^{+/−}$ male mice by using the mirVana RNA isolation kit (Life Tech-nologies). Total RNAs (100 ng) were labeled using the miRNA Complete Labeling and Hyb Kit (Agilent), followed by hybridizing to the Mouse miRNA v21 Microarray (Agi-lent-070155) that contains 4,415 unique probes targeting 1,881 mature miRNAs, according to the mouse miRBase version 21.0 (www.mirbase.org; June 2014). Microarrays were scanned using an Agilent array scanner (G2565CA) at 3-μm resolution. Microarray data were extracted by Agilent Feature Extraction software (v.10.5.1.1) with the miRNA_107_Sep09 protocol. The data process was per-formed using Partek software (St. Louis, MO). The miRNA microarray data analysis was performed as described previ-ously (Chun et al., 2017). In brief, the signal intensities for each miRNA were summarized after quantile normalization among arrays; the Student's t-test was then performed to determine statistical significance between sets of biological replicates from different experimental groups; and the sig-nificant differentially expressed miRNAs were selected through the p-value and fold-change cutoff for the group comparison. The mRNAs targeted by differentially expressed miRNAs were predicted using bioinformatics tools miRWalk and TargetScan. The microarray data have been deposited in the NCBI GEO database under accession number GSE123560.

Quantification of basal body patch displacement. Quantification was performed using previously published methods (Mirzadeh et al., 2010a; Ohata et al., 2014).

Figure 1A:
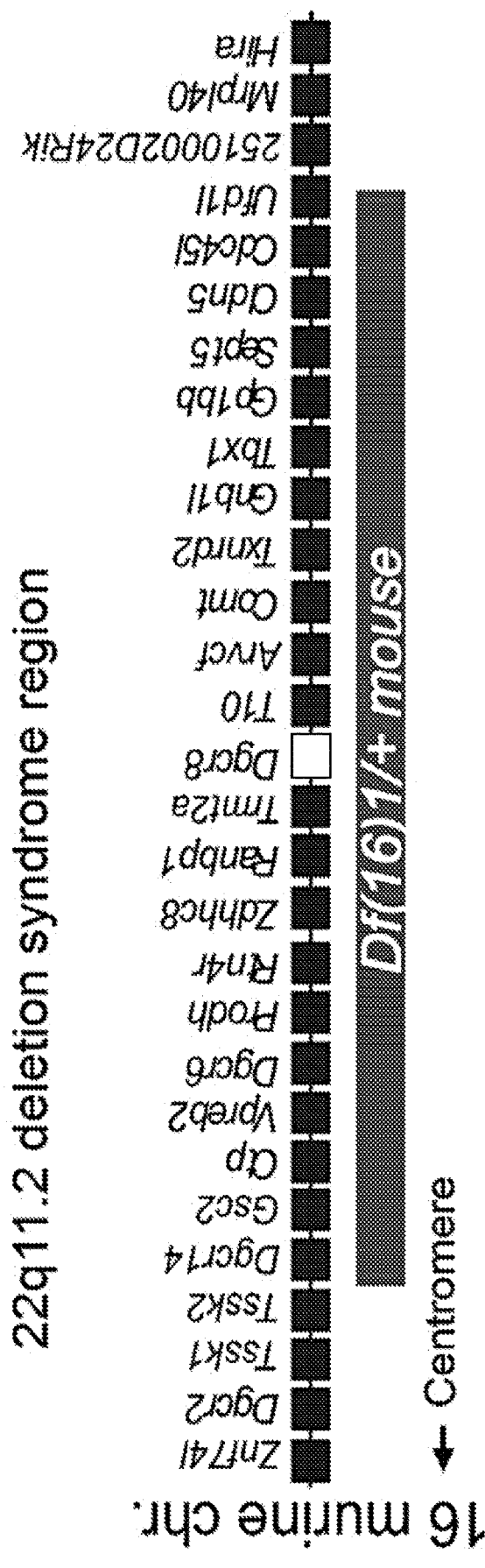
FIGS. 1A-1E. Ventricular Enlargement in Mouse Models of 22q11DS.
Figure 1B:
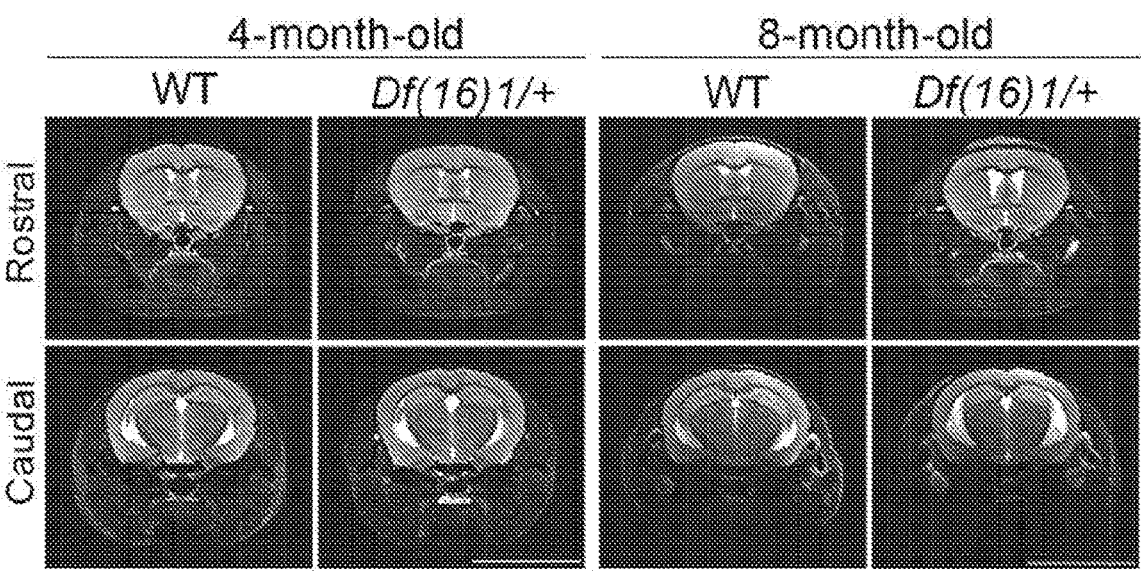
Figure 1C:
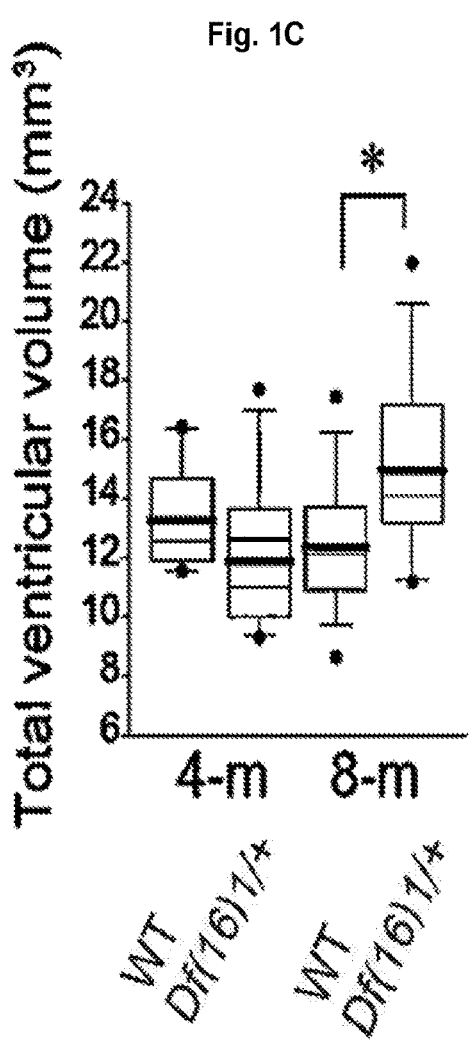
Figure 1D:
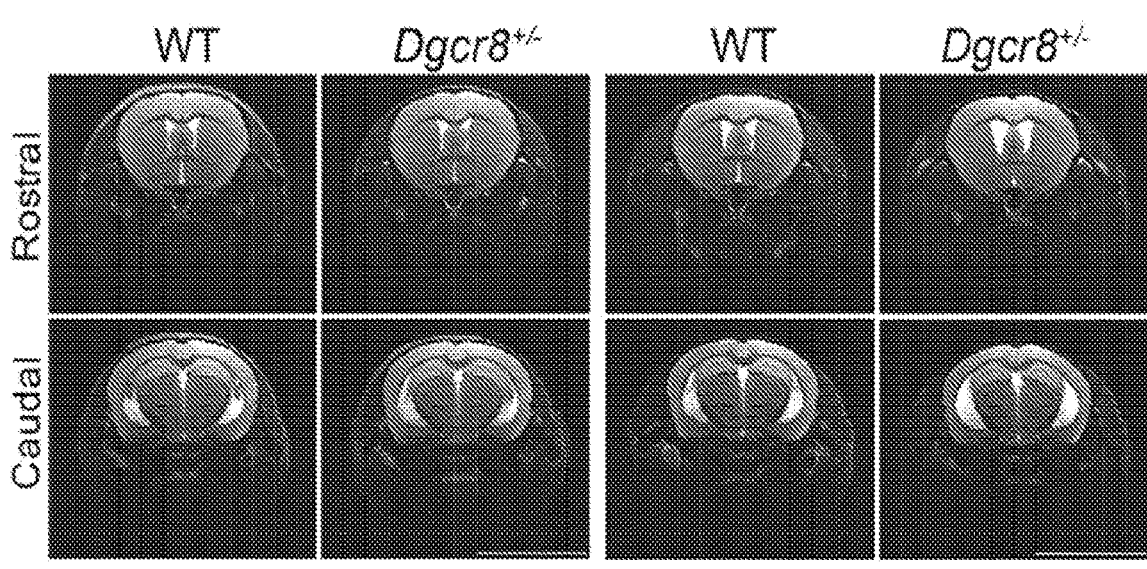
Figure 1E:
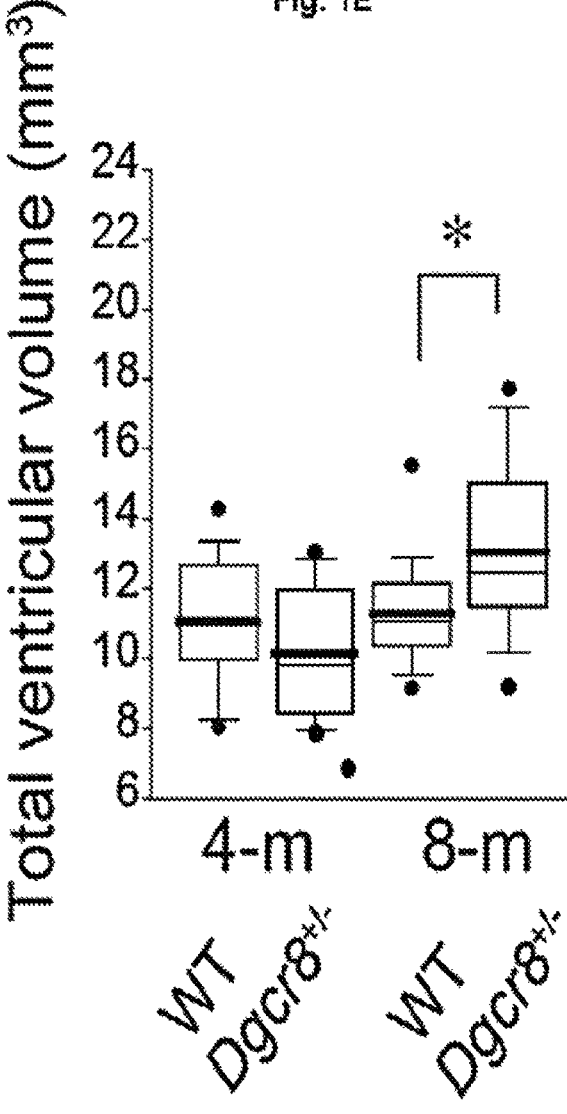

Statistical analyses. All statistics were computed using the Sigma Plot software (Systat Software, Inc., Point Richmond, Dgcr8$^{+/-}$ mice showed volumetric abnormalities comparable to those in Df(16)1/+ mice. Haploinsufficiency of Dgcr8 was correlated with a significant increase in the total ventricular volume in 8-month-old but not 4-month-old mice (FIGS. 1D, 1E). The volume of the LVs and TV increased, but that of the fourth ventricle and aqueduct did not (Table 2). As in Df(16)1/+ mice, the volumes of the whole brain, cortex, and hippocampus of Dgcr8$^{+/-}$ did not differ from those of WT littermates at both ages (FIGS. 8F-8J).

TABLE 2

Comparison of ventricular volumes[a] at two ages in the WT, Df(16)1/+, and Dgcr8$^{+/-}$ mice

| Ventricle Volume | Mean volume ± SD at 4 months | | | Mean volume ± SD at 8 months | | |
|---|---|---|---|---|---|---|
| | WT (n = 10) | Df(16)1/+ (n = 11) | P-value[b] | WT (n = 15) | Df(16)1/+ (n = 14) | P-value[b] |
| Fourth | 1.11 ± 0.18 | 0.94 ± 0.12 | 0.01 | 0.74 ± 0.26 | 0.73 ± 0.31 | 0.95 |
| Aqueduct | 0.53 ± 0.05 | 0.53 ± 0.09 | 0.97 | 0.55 ± 0.13 | 0.48 ± 0.12 | 0.15 |
| Third | 3.34 ± 0.36 | 3.23 ± 0.65 | 1.00 | 2.65 ± 0.55 | 3.30 ± 0.72 | 0.007 |
| Left Lateral | 3.99 ± 0.81 | 3.40 ± 0.90 | 0.25 | 3.96 ± 0.78 | 4.95 ± 1.52 | 0.04 |
| Right lateral | 4.03 ± 0.83 | 3.52 ± 1.71 | 0.40 | 4.25 ± 0.91 | 5.24 ± 1.32 | 0.03 |
| Total | 13.27 ± 1.74 | 11.87 ± 2.52 | 0.07 | 12.36 ± 2.25 | 14.96 ± 3.07 | 0.01 |
| | WT (n = 17) | Dgcr8$^{+/-}$ (n = 18) | | WT (n = 26) | Dgcr8$^{+/-}$ (n = 33) | |
| Fourth | 0.88 ± 0.16 | 0.85 ± 0.14 | 0.50 | 0.84 ± 0.16 | 0.92 ± 0.15 | 0.05 |
| Aqueduct | 0.51 ± 0.10 | 0.46 ± 0.12 | 0.46 | 0.52 ± 0.14 | 0.47 ± 0.13 | 0.16 |
| Third | 2.38 ± 0.27 | 2.39 ± 0.41 | 0.98 | 2.43 ± 0.26 | 2.67 ± 0.31 | 0.002 |
| Left lateral | 3.42 ± 0.66 | 3.29 ± 1.19 | 0.69 | 3.59 ± 0.78 | 4.37 ± 1.29 | 0.003 |
| Right lateral | 3.98 ± 1.14 | 3.59 ± 0.99 | 0.30 | 4.17 ± 0.82 | 4.62 ± 0.98 | 0.06 |
| Total | 11.07 ± 1.69 | 10.15 ± 1.81 | 0.13 | 11.30 ± 1.57 | 13.04 ± 2.48 | 0.003 |

[a]Volumes were measured (in mm$^3$) using a 7 T Bruker ClinScan system.
[b]P-values were calculated by two-tailed Student's t-test. Significant p-values are indicated in bold.

CA). Differences in mean data were determined by the Student's t-test, Mann-Whitney rank-sum test, Kruskal-Wallis one-way analysis, Watson's U2 two-sample test, Shapiro-Wilk normality test, or a one-way ANOVA followed by Student-Newman-Keuls post hoc test and were considered significant if the p-value of the test result was less than 0.05.

Example 2: Haploinsufficiency of the 22q11DS Gene Dgcr8 Causes Progressive Ventriculomegaly Magnetic resonance imaging (MRI) analysis was performed in Df(16)1/+ murine models of 22q11DS (Lindsay et al., 1999) (FIG. 1A). The onset of clinical manifestations of psychosis in patients with 22q11DS or SCZ typically occurs during late adolescence or early adulthood [16-30 years (Almeida et al., 1995; Bassett et al., 2003; Mueser and McGurk, 2004)]. This age is developmentally equivalent to 3 to 4 months in mice (Flurkey et al., 2007). Thus, the neuroanatomical features were examined in mice that were 4 months or older. A considerable increase in the total ventricular volume was detected in 8-month-old but not 4-month-old Df(16)1/+ mice compared to wild-type (WT) littermates (FIGS. 1B, 1C). At the regional level, a significant enlargement of the LVs and TV was observed but there was no difference in the size of the fourth ventricle or the aqueduct in 8-month-old Df(16)1/+ mice compared to age matched controls (Table 2). Despite the ventricular enlargement, the volumetric characteristics of the total brain, cortex, and hippocampus of Df(16)1/+ mice were comparable to those of WT littermates (FIGS. 8A-8E).

Figure 9A:
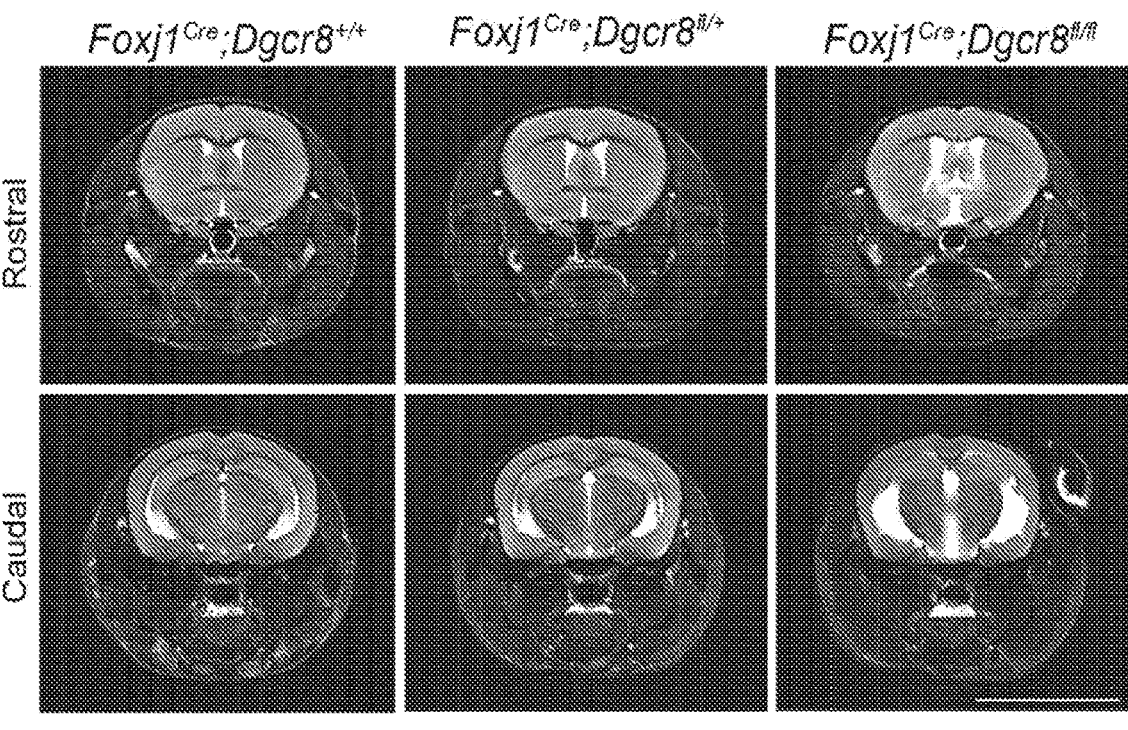
Figure 9A:
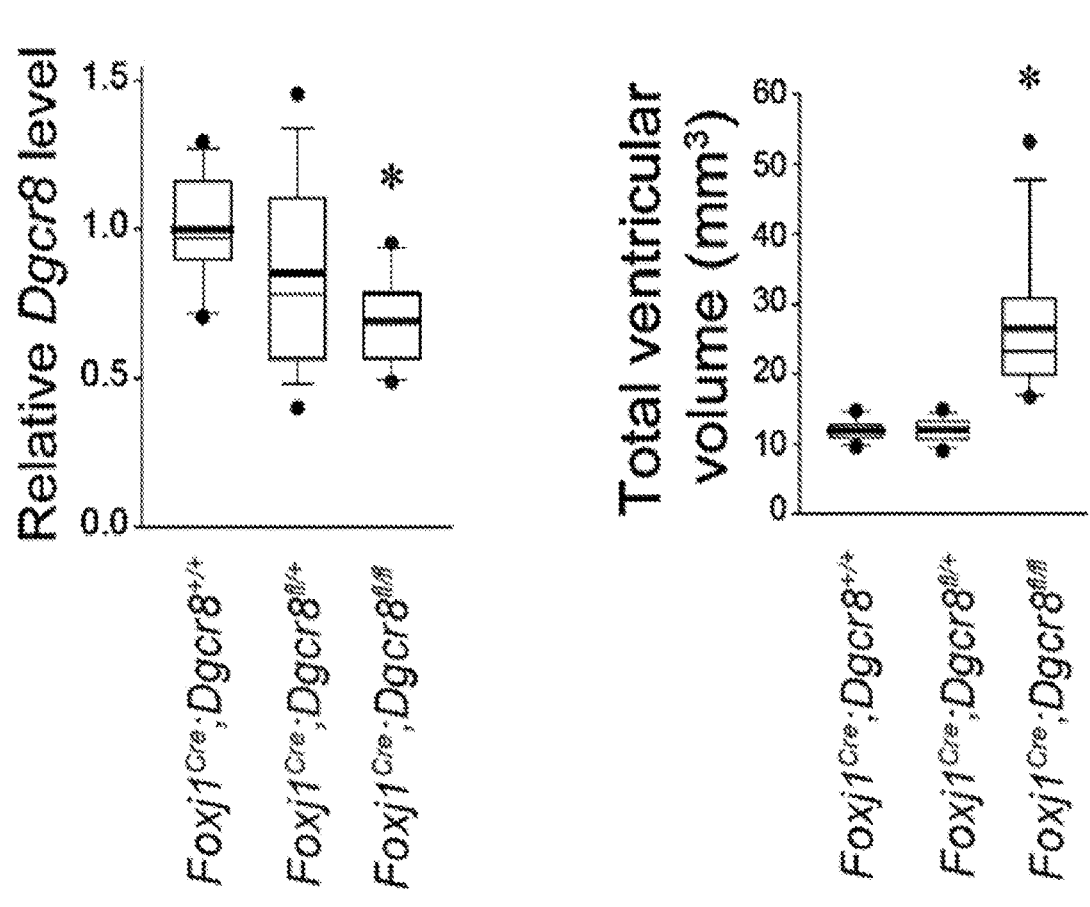
Figure 10A:
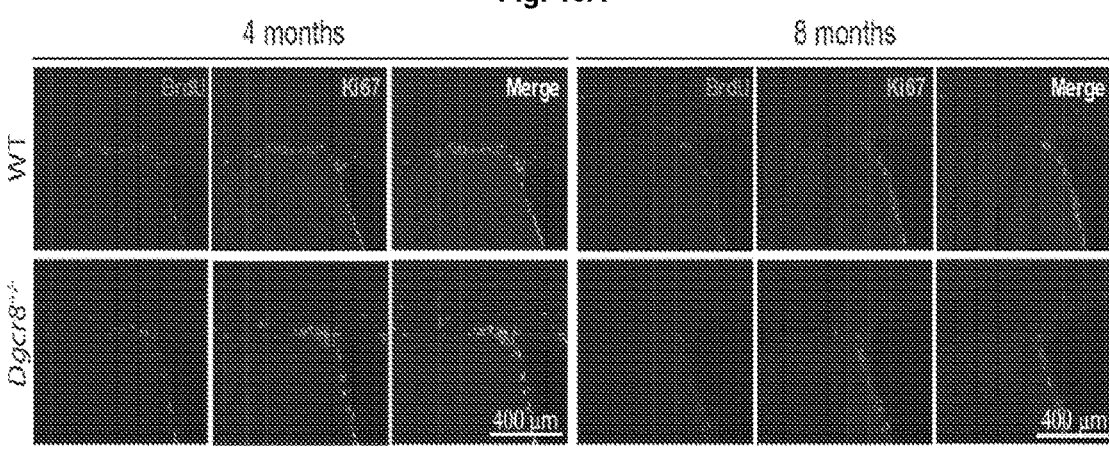
Figure 10B:
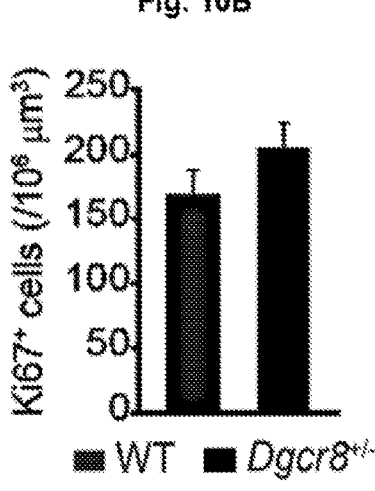
Figure 10C:
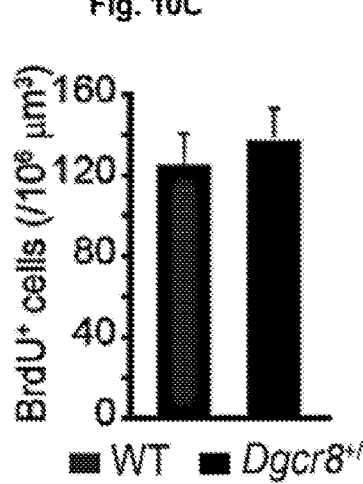
Figure 10D:
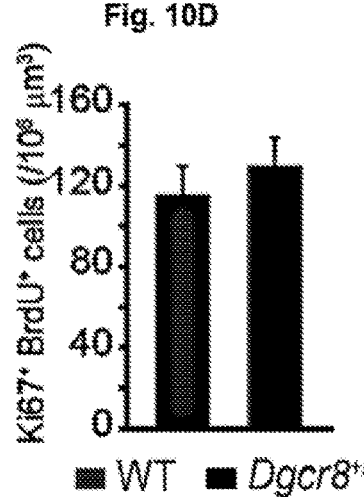
Figure 10E:
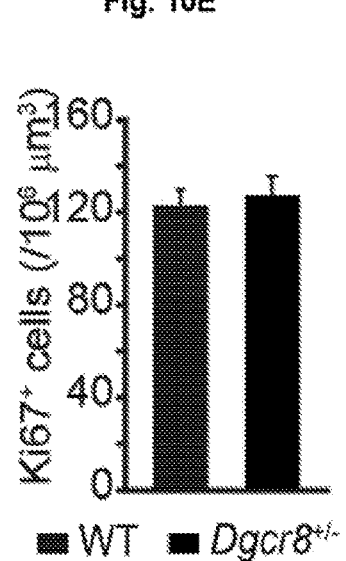
Figure 10F:
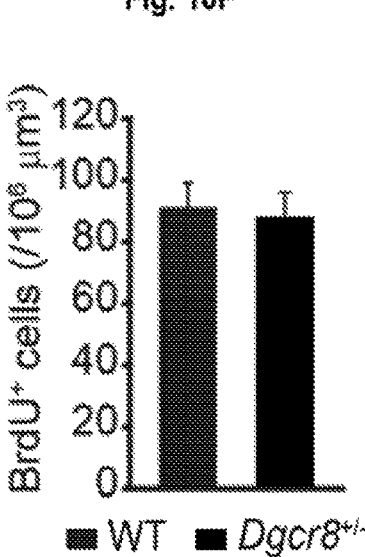
Figure 10G:
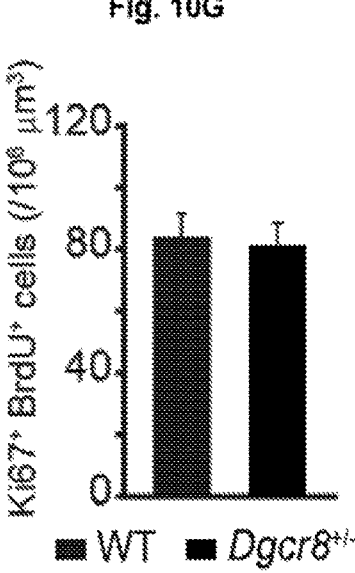
Figure 10K:
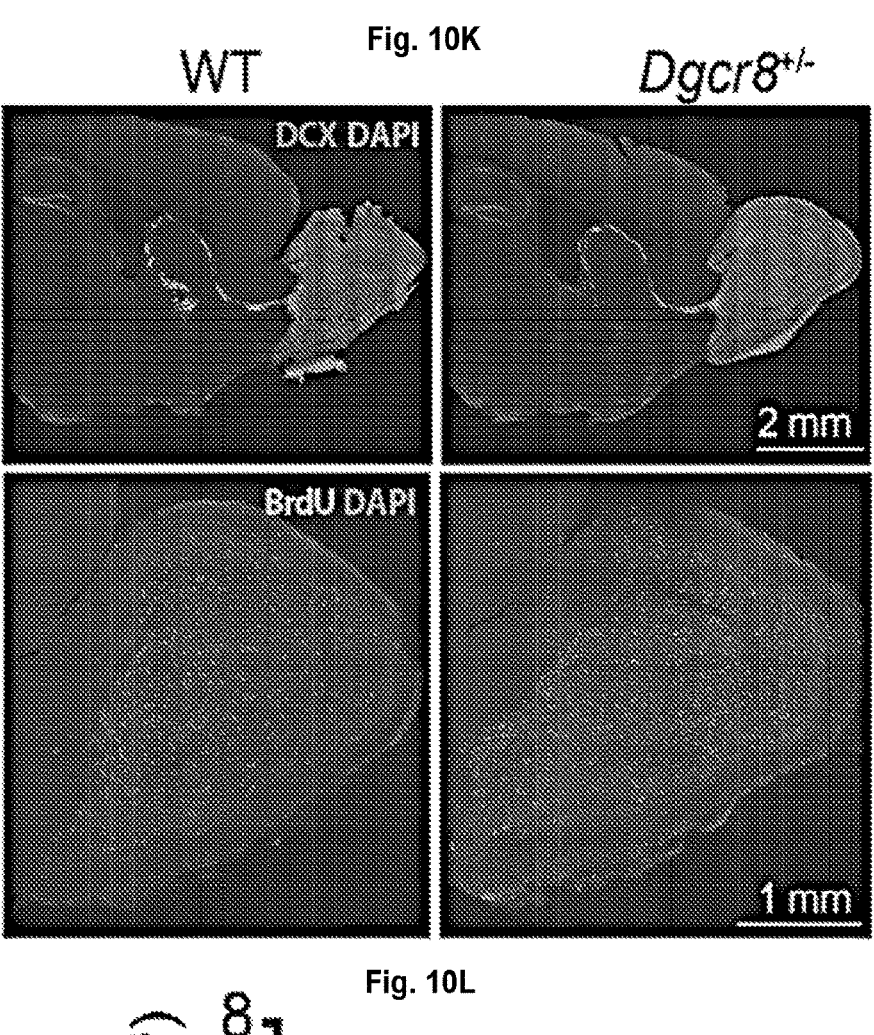
Figure 10L:
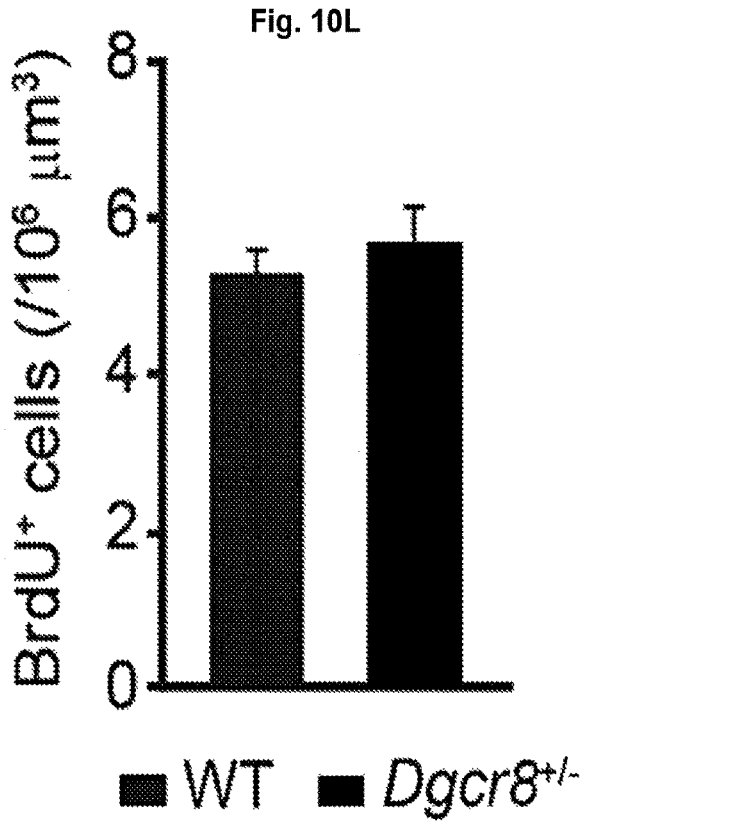

To test if deletion of Dgcr8 limited to the subventricular zone (SVZ), especially in ependymal cells, replicates ventriculomegaly, Dgcr8 conditional-knockout mice were generated by crossing mice carrying a Dgcr8 floxed allele (Wang et al., 2007) with Foxj1$^{Cre}$ mice that express Cre recombinase in ependymal cells (Zhang et al., 2007). Foxj1$^{Cre}$;Dgcr8$^{fl/fl}$ mice but not Foxj1$^{Cre}$;Dgcr8$^{fl/fl}$ mice showed lower Dgcr8 transcript levels in the LV walls and drastically increased ventricular volume compared to WT littermates (FIG. 9), suggesting that a cell-autonomous Dgcr8 deletion in the ependymal cells is sufficient to cause ventricular enlargement in a dose-dependent manner.

Volumetric changes in Dgcr8$^{+/-}$ mice were not associated with changes in cerebral spinal fluid (CSF) osmolality (FIG. 8K) or abnormal characteristics of neural progenitors in the SVZ (FIG. 10). Neural progenitor proliferation (measured by the presence of proliferation markers Ki67 and BrdU in the SVZ) (FIGS. 10A-10G), apoptotic cell death (measured by cell positivity for cleaved caspase-3 in the SVZ) (FIGS. 10H-10J), and SVZ neuronal migration (measured by the presence of the neuroblast marker doublecortin and BrdU$^+$ cells in the olfactory bulb) (FIGS. 10K, 10L) were normal in Dgcr8$^{+/-}$ mice compared to WT littermates. These observations indicate that although Dgcr8 haploinsufficiency may cause ventriculomegaly, the mechanism for such a result does not involve changes in CSF composition or SVZ neurogenesis.

Figures 2A, 2B:
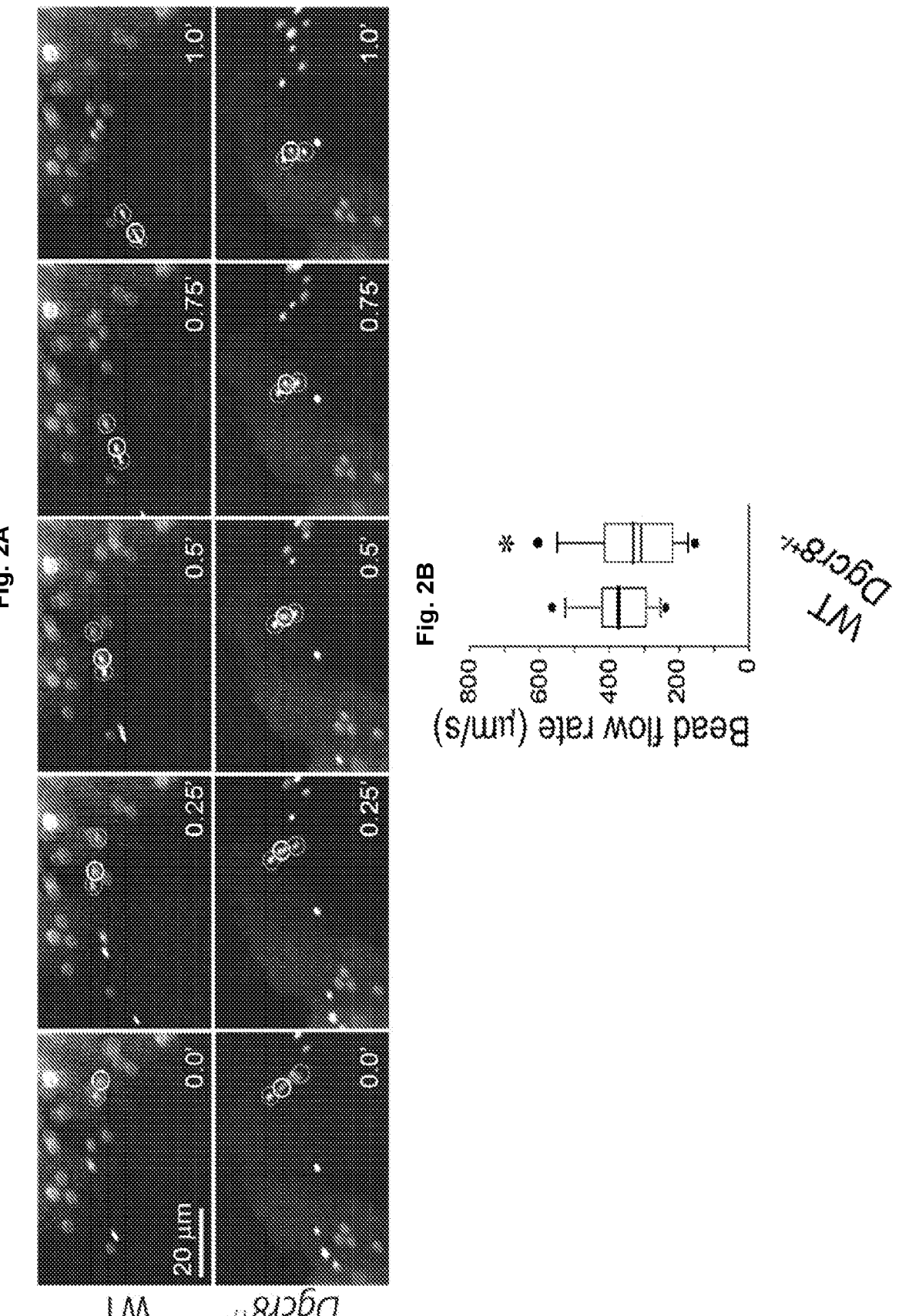

Example 3: Slower Ependymal Flow and Ciliary
Beating in the Lateral Ventricles of Dgcr8+/− Mice To test whether Dgcr8 deficiency affects ependymal func-
tion, ependymal flow that is directed by motile ciliary
beating was first examined Individual fluorescent microbead
movements were compared at the apical surface of ependy-
mal cells in acute LV whole-mounts from 8-month-old WT
or Dgcr8+/− mice (FIGS. 2A, 2B). Although the overall
direction of ependymal flow was comparable between
Dgcr8+/− and WT mice, the average bead velocity was
slower in the mutants (FIGS. 2A, 2B), suggesting that Dgcr8
haploinsufficiency affects motile ciliary beating. To directly
measure motile ciliary beating frequency (CBF), linescan
fluorescent imaging was used in brain slices from
Arl13b^eGFP transgenic mice, which express green fluores-
cence protein (GFP) only in primary and motile cilia (Del-
ling et al., 2013) (FIGS. 2C-2D). Using this approach,
slower beating of motile cilia was observed in Dgcr8+/−;
Arl13b^eGFP mice aged 4-5, 6-7, and 8-9 months but not in
those aged 2-3 months, compared to the respective controls
(Dgcr8+/+;Arl13b^eGFP littermates) (FIGS. 2D-2H). Similar
results were observed using simultaneous differential inter-
ference contrast (DIC) imaging. Using these modes of
imaging, it was observed that in addition to being slower,
motile cilia movements were less stereotypical (more asyn-
chronous) in acute brain slices and whole-mounts from older
(>4 months) Dgcr8+/− mice compared to WT littermates.

Figure 2K:
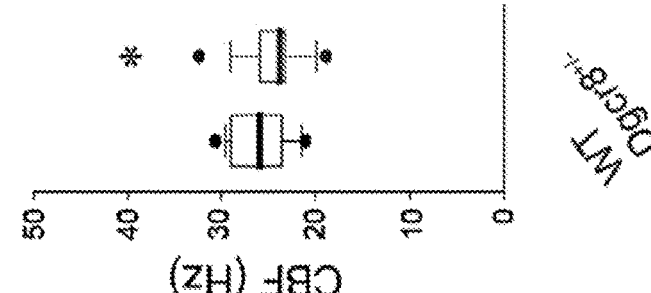
Figure 2J:
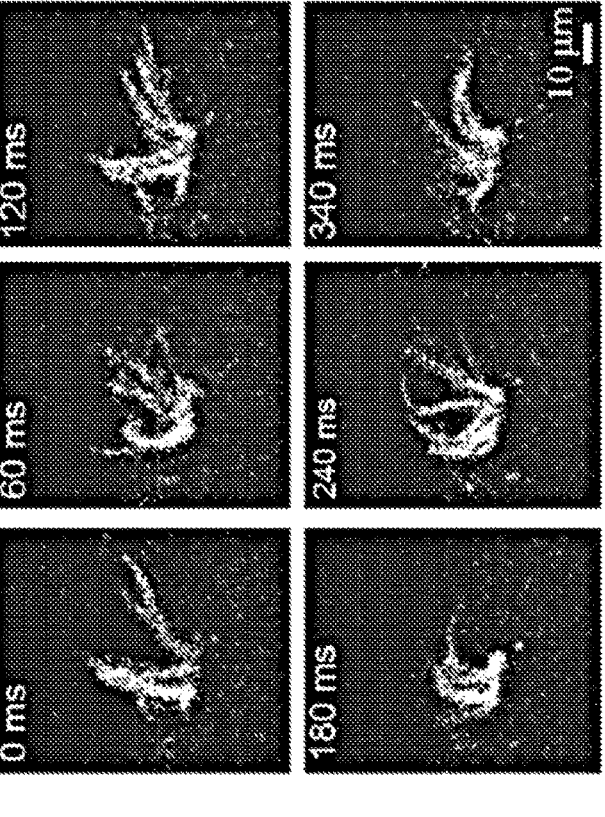
Figure 2I:
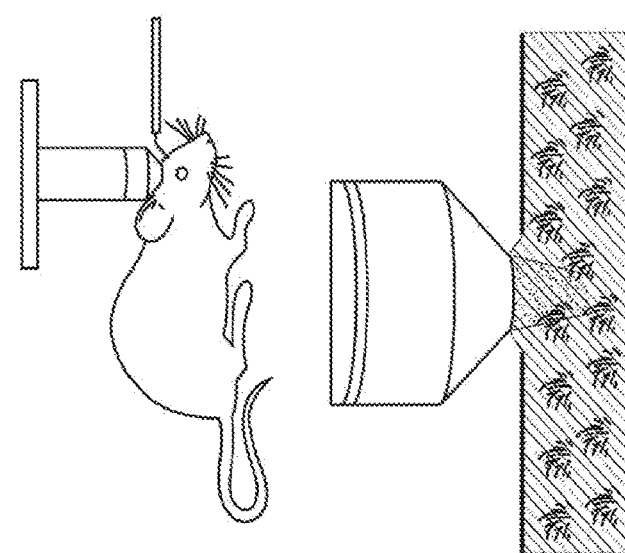

To show ciliary abnormality in vivo, ependymal CBF in
anesthetized mice was measured using two-photon imaging
(FIG. 2I). This approach allowed for detecting quickly
beating individual cilia within the cilia tuft at the surface of
the LV wall (FIG. 2J). Similar to results from the ex vivo
whole-mount experiments, the ependymal CBF in vivo was
slower in 8-month-old Dgcr8+/−;Arl13b^eGFP mice than in
Dgcr8+/+;Arl13b^eGFP littermates (FIG. 2K). Together, these
results indicate that motile cilia beat significantly slower in
older Dgcr8+/− mice, suggesting a link between a deficit in
ciliary beating and ventriculomegaly.

Figures 3A, 3B, 3C, 3D:
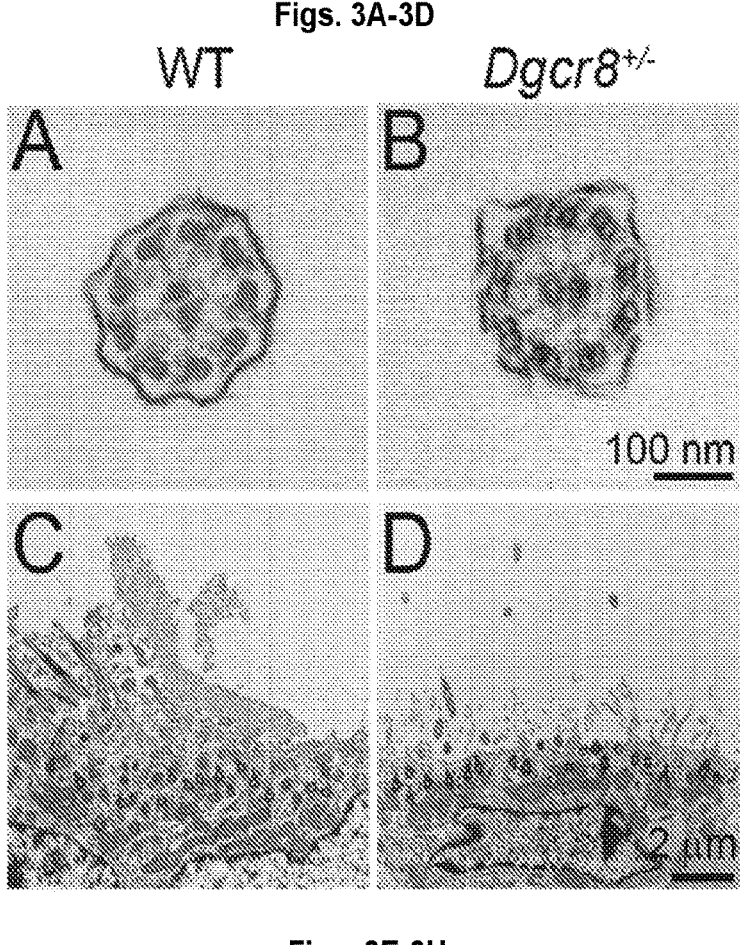
Figures 3E, 3F, 3G, 3H:
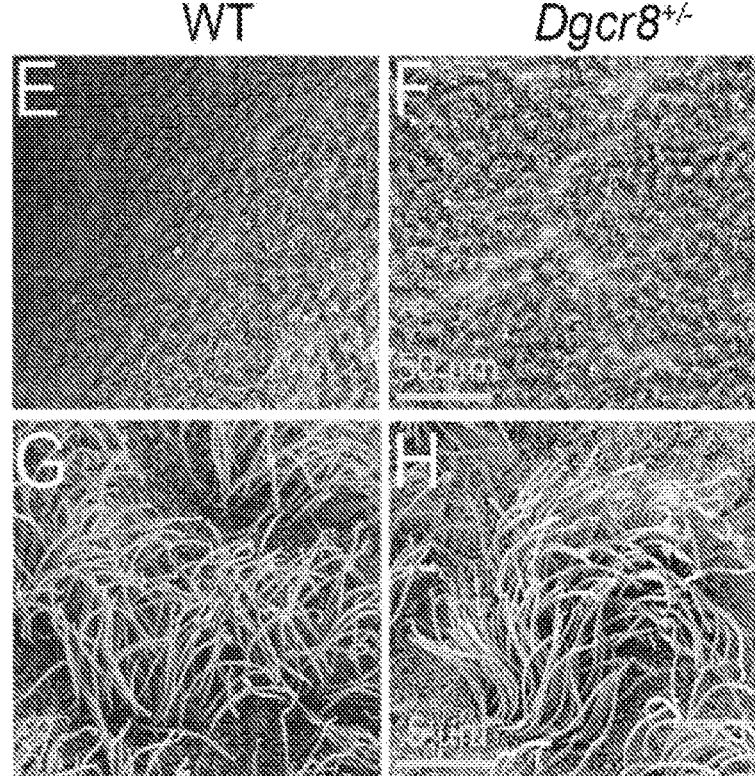
(FIGS. 3E-3H) Representative SEM images of motile cilia in ependymal cells of WT and Dgcr8$^{+/-}$ mice.
Figures 3I, 3J, 3K, 3L:
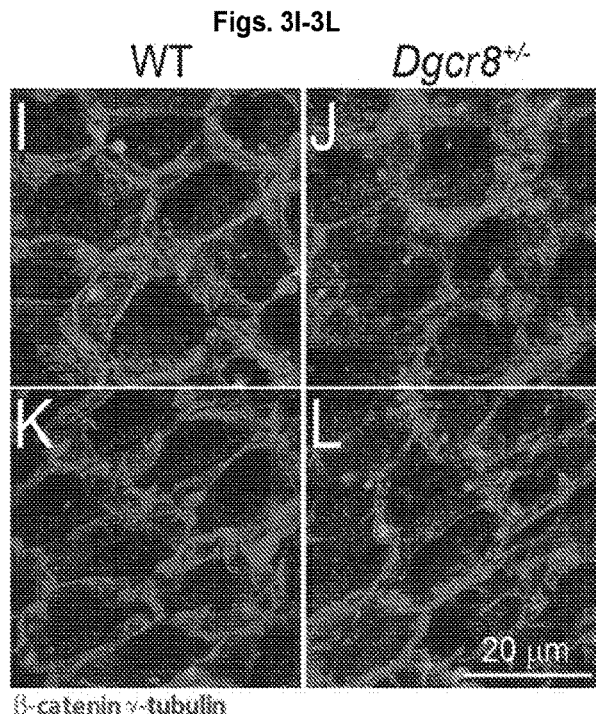
(FIGS. 3I-3L) Confocal images of basal body patch position as an anatomical indicator of ependymal planar polarity in the anterior dorsal (FIGS. 3I, 3J) and anterior ventral (FIGS. 3K, 3L) LV walls of WT and Dgcr8$^{+/-}$ mice. Whole-mount brains were stained with antibodies against β-catenin (intercellular junctions) and γ-tubulin (basal bodies).
Figures 3M, 3N, 3O:
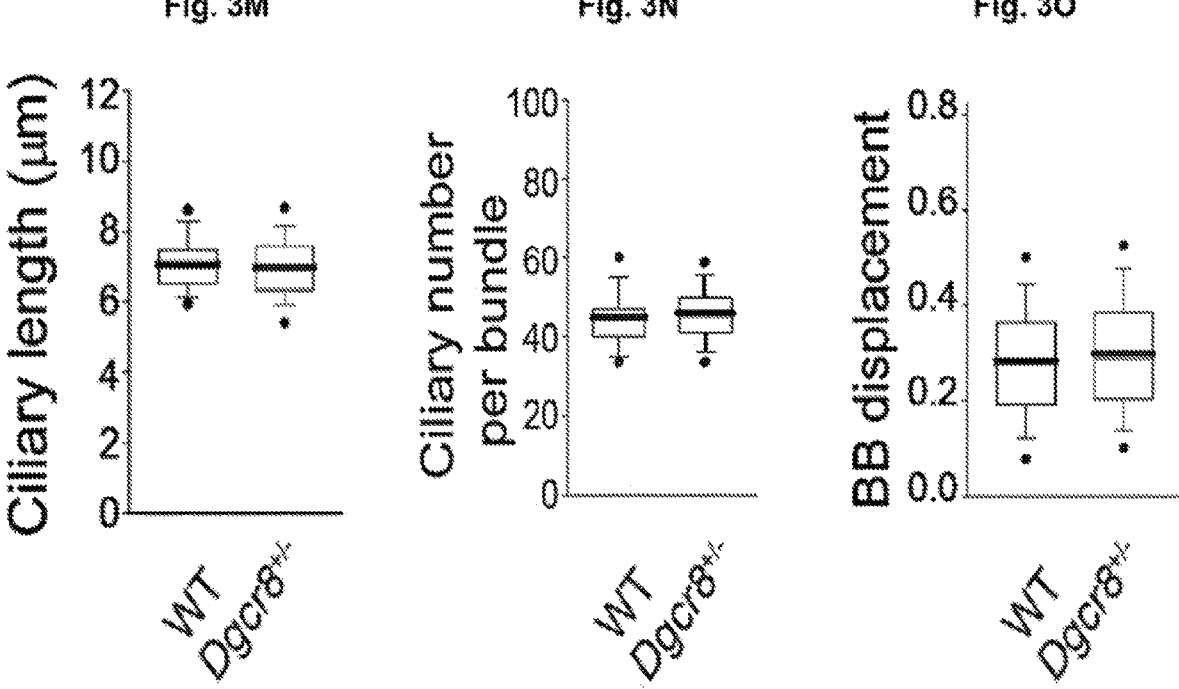
(FIGS. 3M-3O) Mean ciliary length (FIG. 3M), ciliary number in a bundle (FIG. 3N), and distance of the basal body (BB) displacement from the center of an ependymal cell (FIG. 3O) in WT and Dgcr8$^{+/-}$ mice.
Figure 3P:
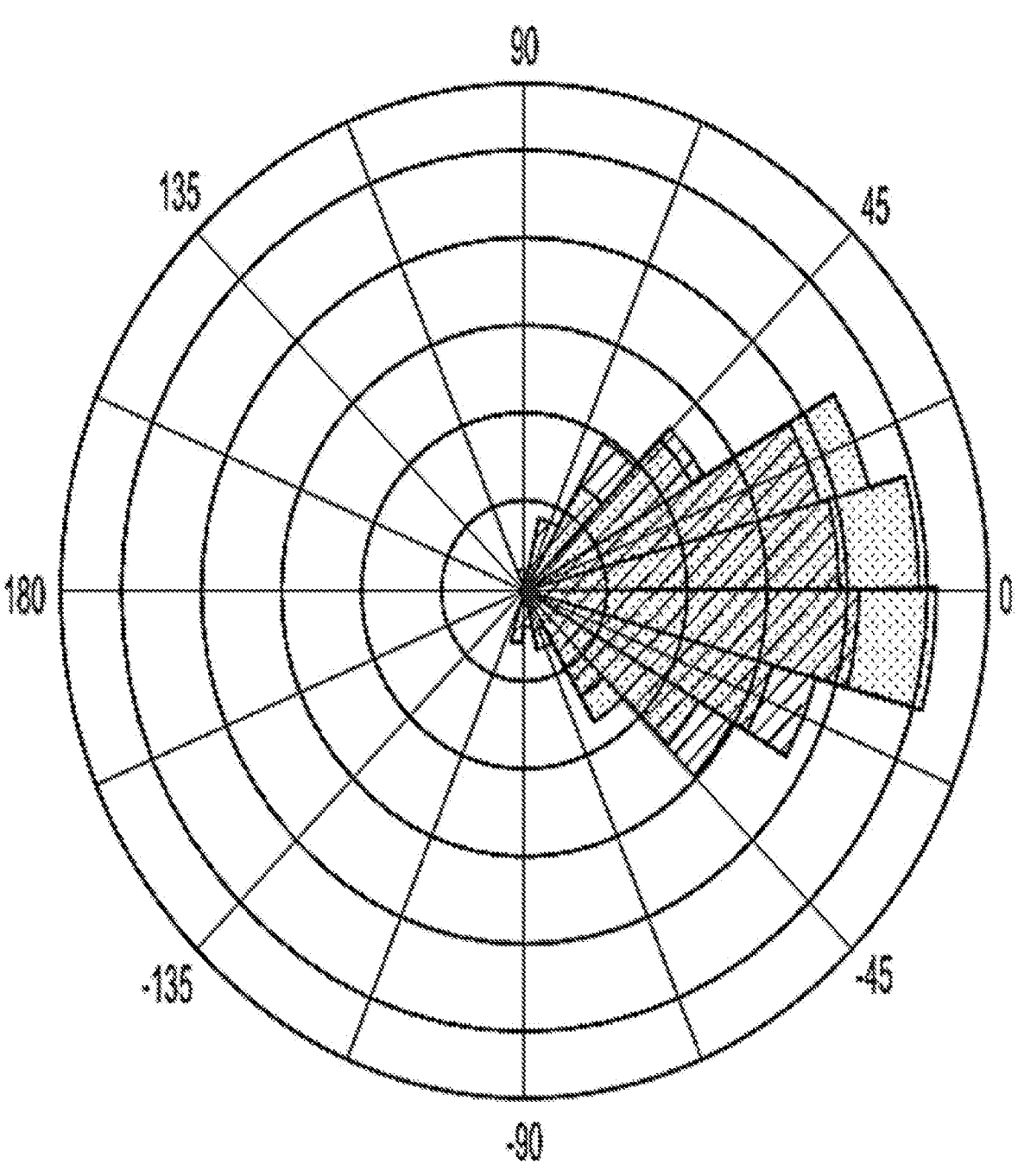

Example 4: Dgcr8 Haploinsufficiency does not
Affect Ependymal Cell Structure or Planar Polarity The increase in ventricular volume in Dgcr8+/− mice was
not associated with structural changes in ependymal cilia or
planar cell polarity. Transmission electron microscopy
(TEM) revealed normal microtubule configuration in the
9+2 axoneme and basal body docking to the apical mem-
brane of ependymal cells in Dgcr8+/− mice (FIGS. 3A-3D).
Scanning electron microscopy also showed no abnormalities
in morphology, length, or the number of motile cilia on the
wall of the LVs in the Dgcr8+/− mice compared to WT
littermates (FIGS. 3E-3H, 3M, 3N). Furthermore, planar
polarity of ependymal cells was not altered in Dgcr8+/− mice
(FIGS. 3I-3L). Planar polarity within the ependymal cells is
determined by the location of the microtubule-based basal
bodies, which give rise to the motile cilia (Mirzadeh et al.,
2010a). Co-labeling of the cell adherens junction and basal
body with antibodies against β-catenin and γ-tubulin in the
LV wall showed preserved cell polarity in both genotypes.
Displacement of the basal body patch from the cell center,
an indicator of translational polarity, was similar between
the genotypes (FIG. 3O). Furthermore, the alignment of
rotational orientation of basal bodies, which is thought to
determine the direction of motile cilia beating (Bayly and
Axelrod, 2011; Guirao et al., 2010; Hirota et al., 2010; Ohata et al., 2014; Tissir and Goffinet, 2013; Wallingford, 2010),
was not altered in Dgcr8+/− mice (FIG. 3P).

Figure 11:
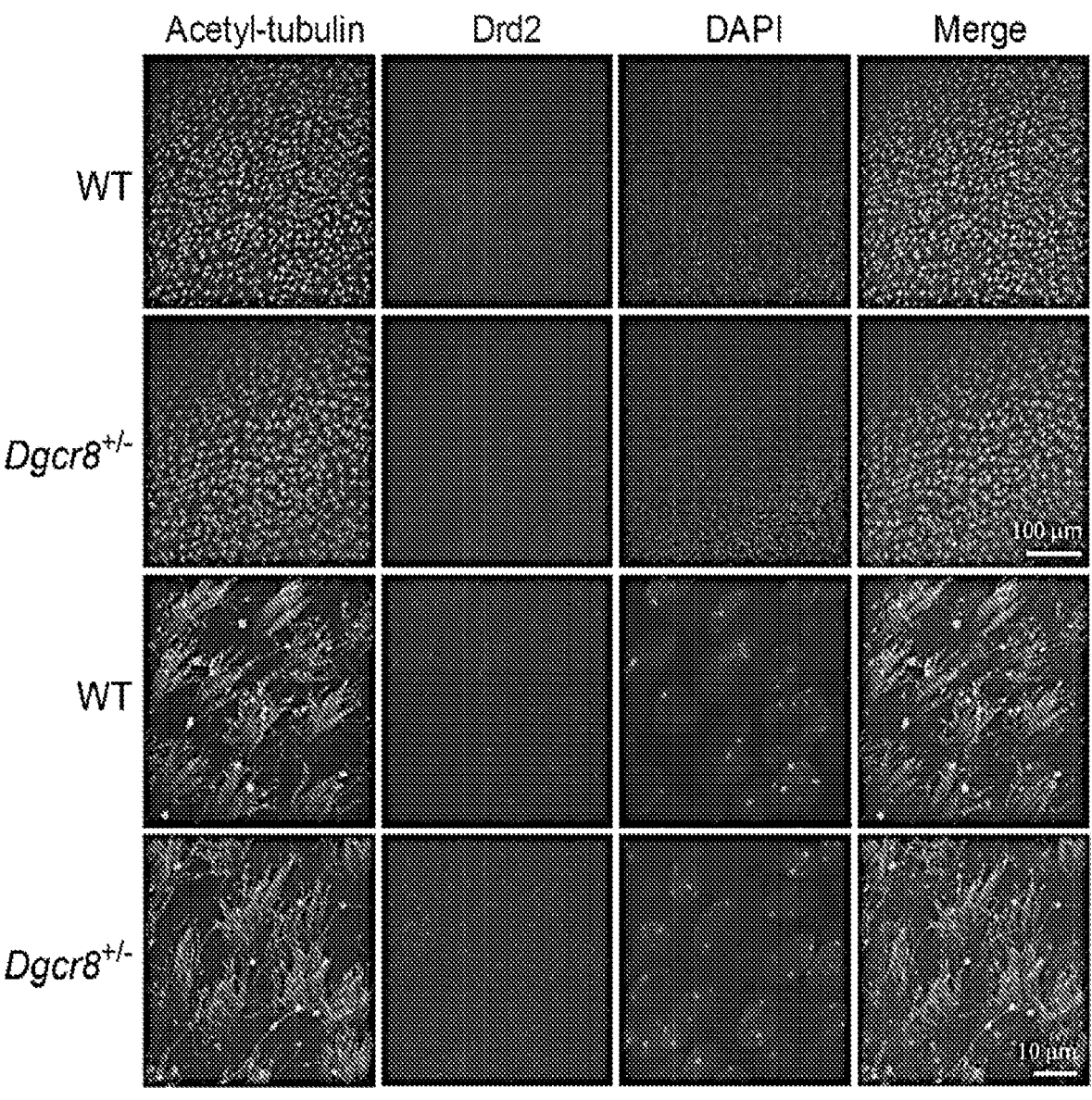
FIG. 11. The Lack of Expression of Dopamine Receptor Drd2 in the LV Wall, Related to FIGS. 4A-4I. Confocal images show lack of Drd2 expression in the ependymal cells of whole-mount LV walls from WT or Dgcr8$^{+/-}$ mice. Acetyl-tubulin antibody is used as a marker of motile cilia and DAPI stains the nuclei.

Example 5: Dysregulation of the Dopamine
Receptor Drd1 in Ependymal Cells of Dgcr8+/−
Mice Previous reports indicate that Dgcr8 regulates the expres-
sion of dopamine receptors through specific miRNAs (Chun
et al., 2014, 2017). Dopamine receptors are present not only
on neurons but also on ciliated ependymal cells (Howard et
al., 1998; Tome et al., 2007), where catecholamine projec-
tions from the subependymal layer may form synapses with
them (Hoglinger et al., 2004; Michaloudi and Papadopoulos,
1996; Tome et al., 2007). Therefore, it was tested if Dgcr8
haploinsufficiency affects ciliary beating through the regu-
lation of dopamine receptor expression. Immunostaining of
the LV wall for a motile cilia marker (i.e., acetylated tubulin)
and dopamine receptors revealed that Drd1s colocalize with
the motile cilia (FIG. 4A). By contrast, Drd2s did not (FIG.
11). Super-resolution imaging revealed that immunolabeling
of the motile cilia with antibodies against Drd1 was specific
because it was substantially diminished in Foxj1^Cre;Drd1^fl/fl
mice (FIG. 4B).

Figure 4C:

To further confirm the subcellular localization of Drd1 in
ependymal cells, immunogold EM experiments were per-
formed in sections containing ependymal cells. The gold
particles were detected in the cytoplasm of ependymal cells
and cilia, including in the axoneme, near the outer and
central microtubules, and at the basal body and its distal
appendages (FIG. 4C).

Figure 4D:
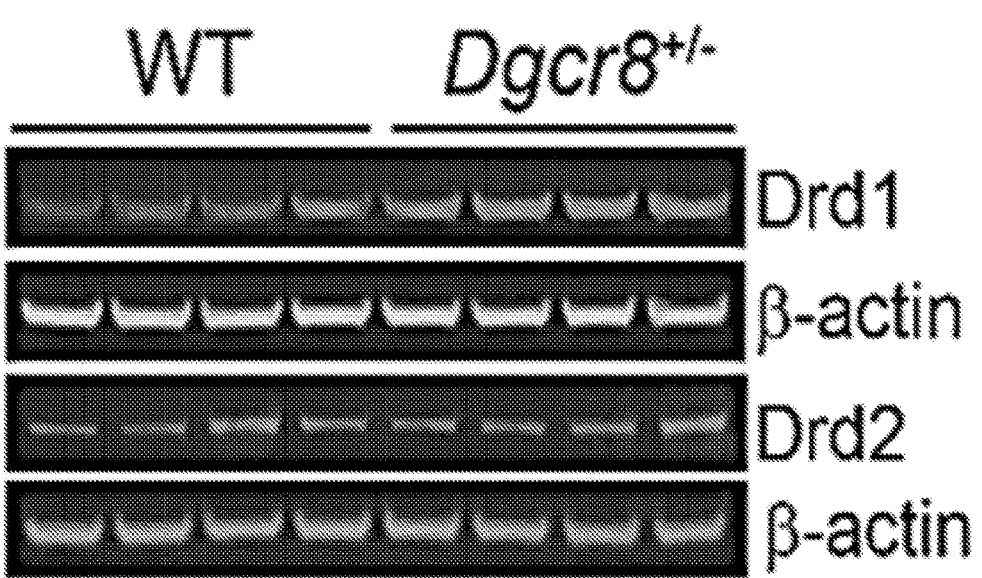
Figure 4D:
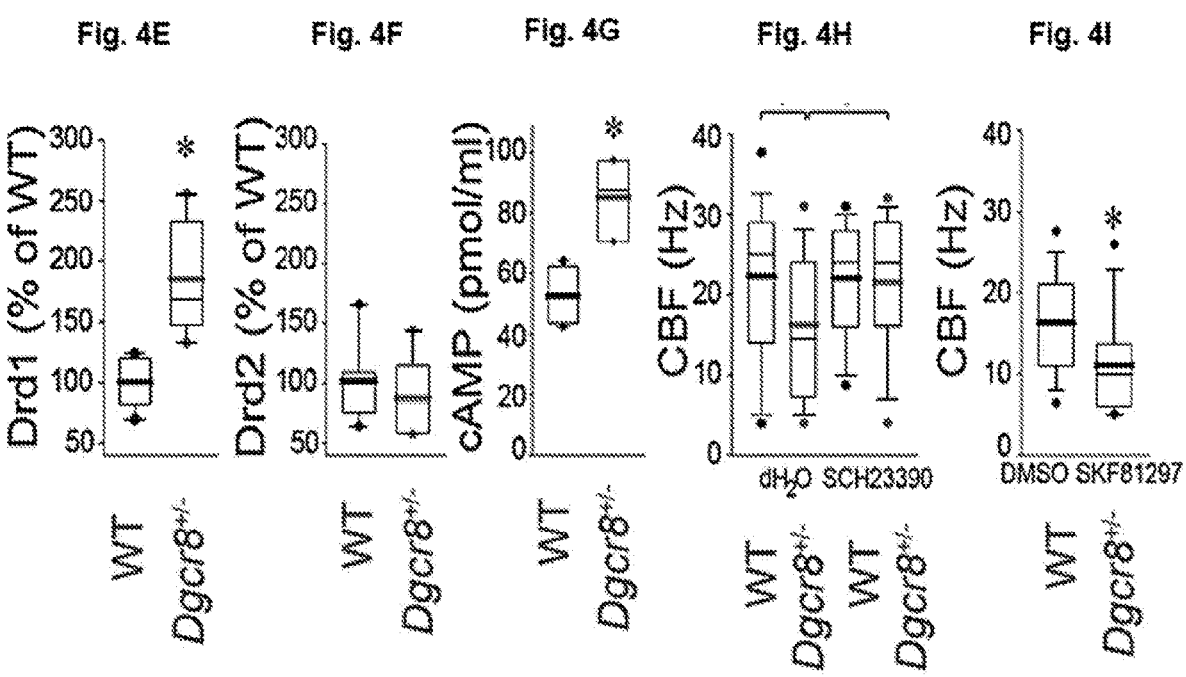

To determine if Dgcr8 haploinsufficiency affects dop-
amine receptor expression, Western blotting was performed
for Drd1 and Drd2 proteins in extracts from the LV walls.
The expression level of Drd1 but not Drd2 was significantly
elevated in Dgcr8+/− mice compared to WT controls (FIGS.
4D-4F). Consistent with this finding, the levels of intracel-
lular cAMP, the downstream effector of Drd1 signaling, was
also significantly increased in the LV wall of Dgcr8+/− mice
(FIG. 4G). Furthermore, blocking Drd1 activity with
SCH23390, a Drd1-specific antagonist, rescued abnormal
ependymal function in Dgcr8+/− mice (FIG. 4H). SCH23390
significantly accelerated ependymal CBF (p<0.001), com-
pared to vehicle in slices from Dgcr8+/− mice, making their
CBF comparable to that of WT mice. Conversely, activation
of Drd1 by SKF81297, a Drd1-specific agonist, mimicked
the Dgcr8+/− ciliary beating phenotype in WT mice (FIG.
4I). Application of SKF81297 slowed ependymal CBF com-
pared to vehicle treatment in slices from WT mice. Together,
these results suggest that Dgcr8 haploinsufficiency upregu-
lates Drd1 in ependymal cells, and this reduces their CBF.
Because a major function of Dgcr8 is production of miR-
NAs, it was next examined whether a Dgcr8-miRNA-Drd1
mechanism contributes to the deceleration of ependymal
CBF in 22q11DS mice.

Figure 5A:
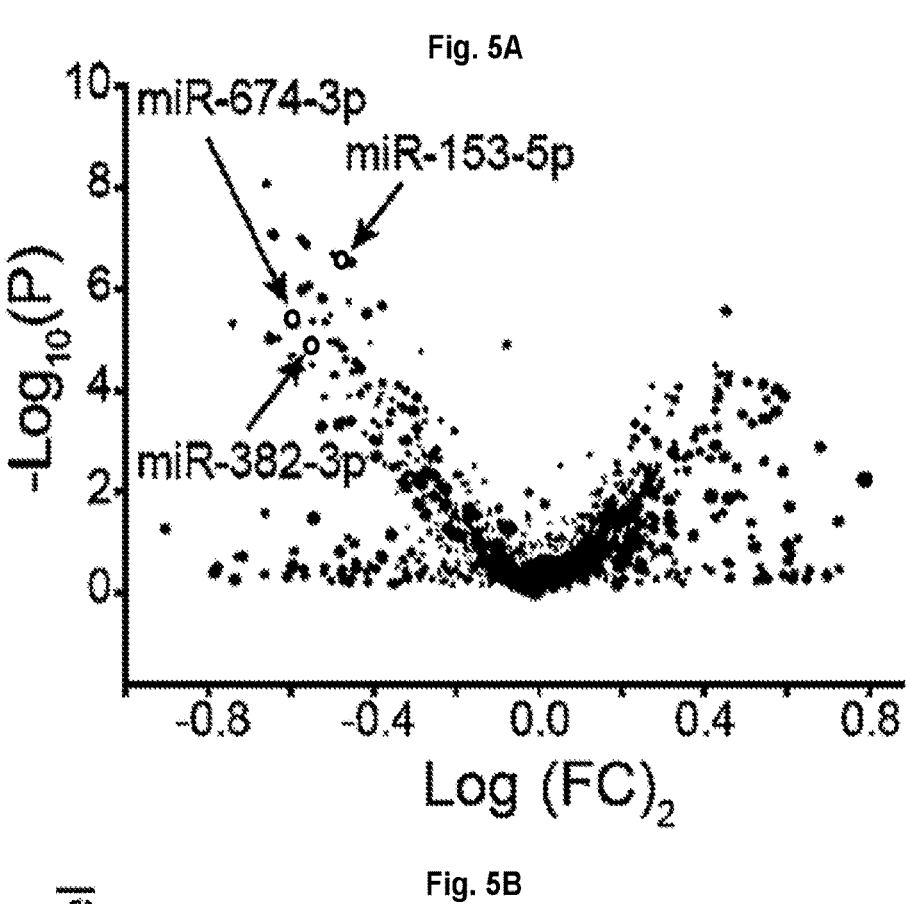
Figure 5B:
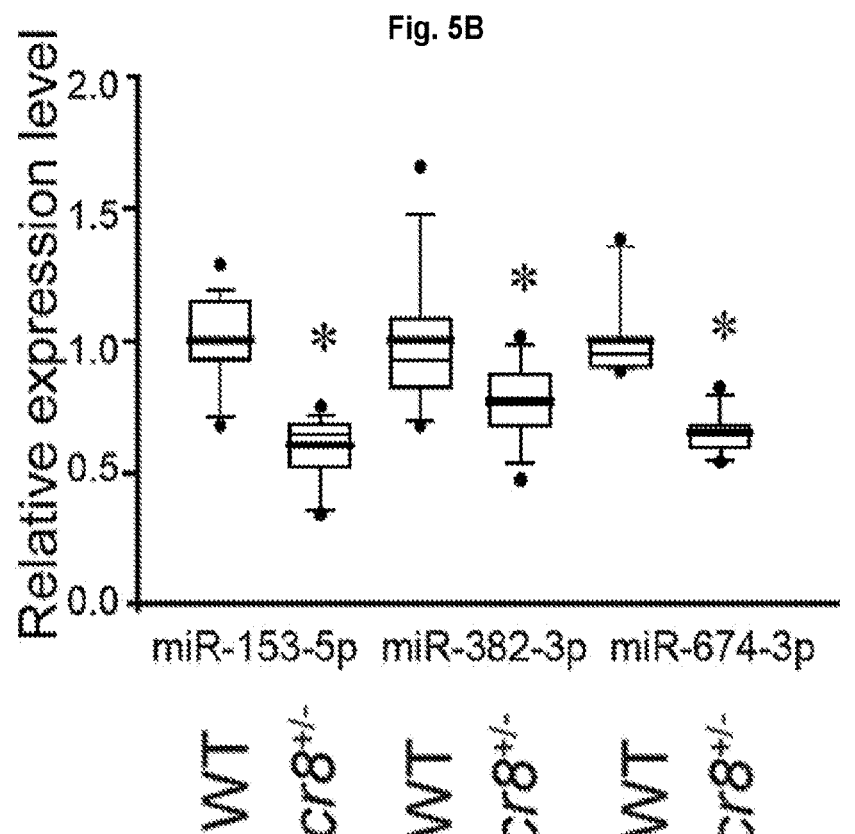
Figure 5C:
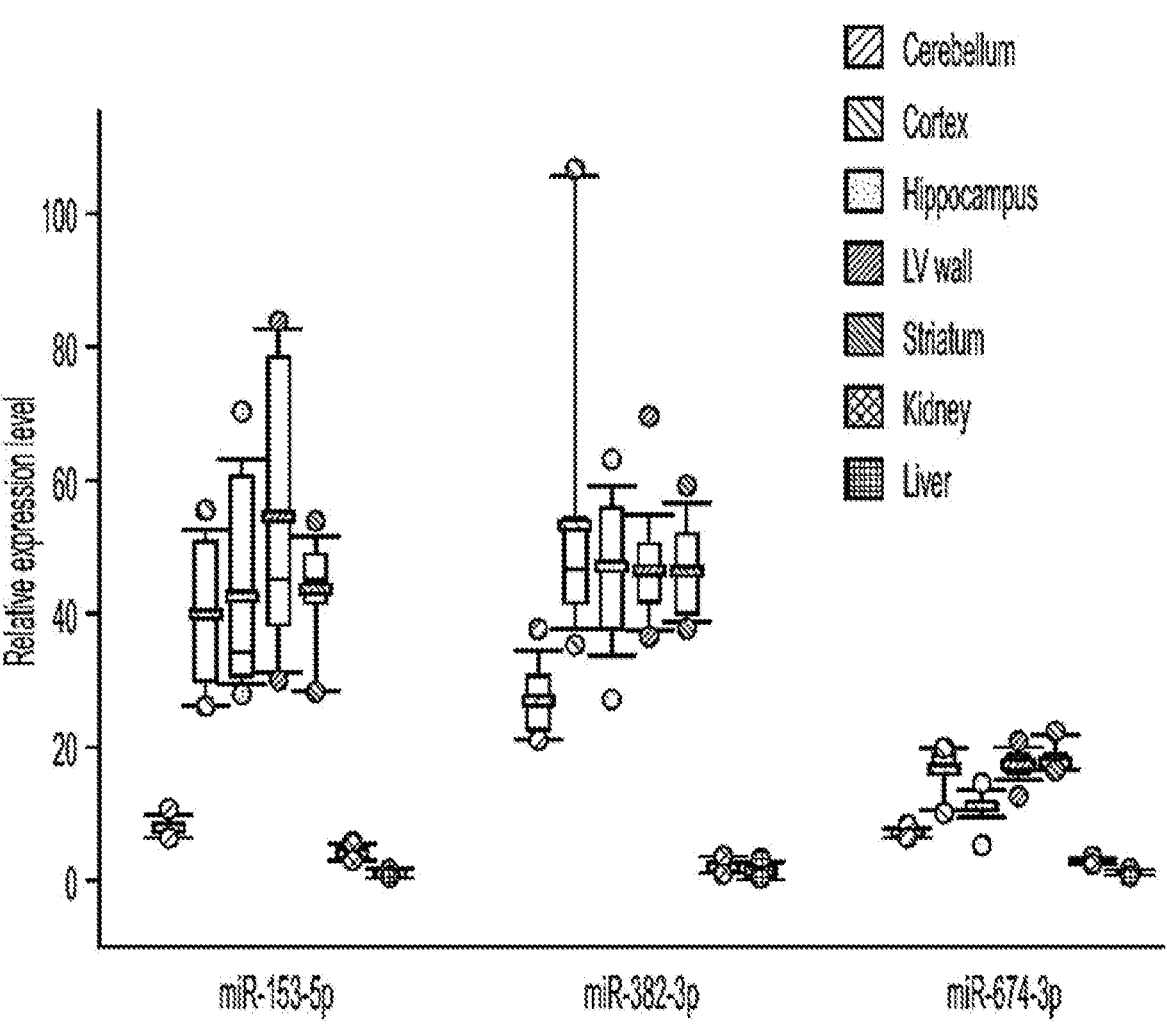
Figure 5D:
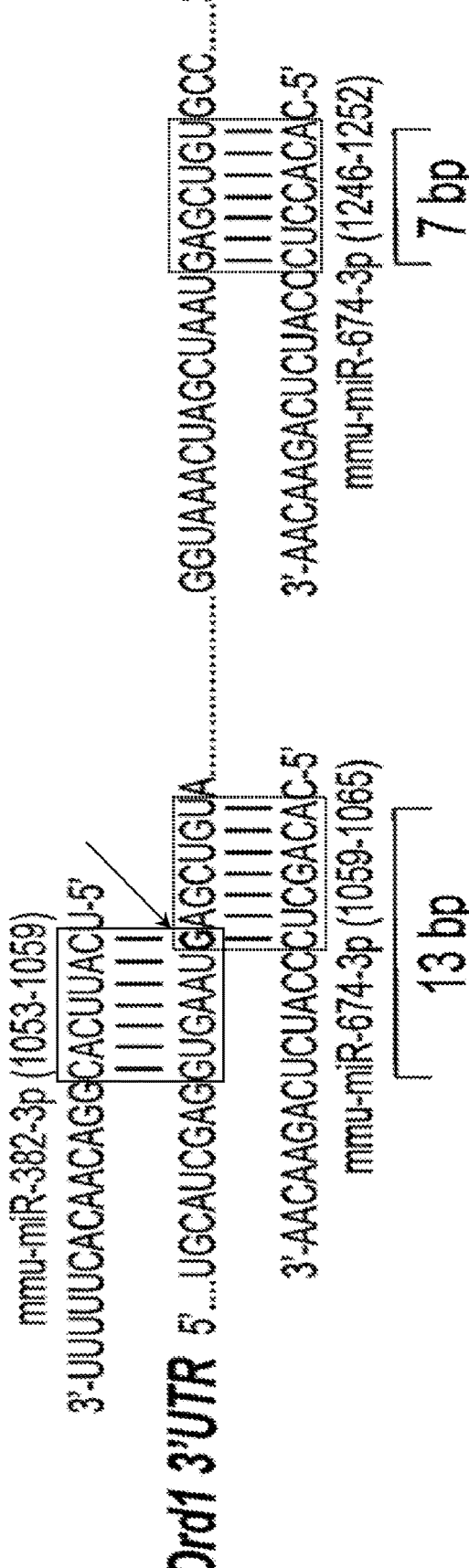
Figure 5E:
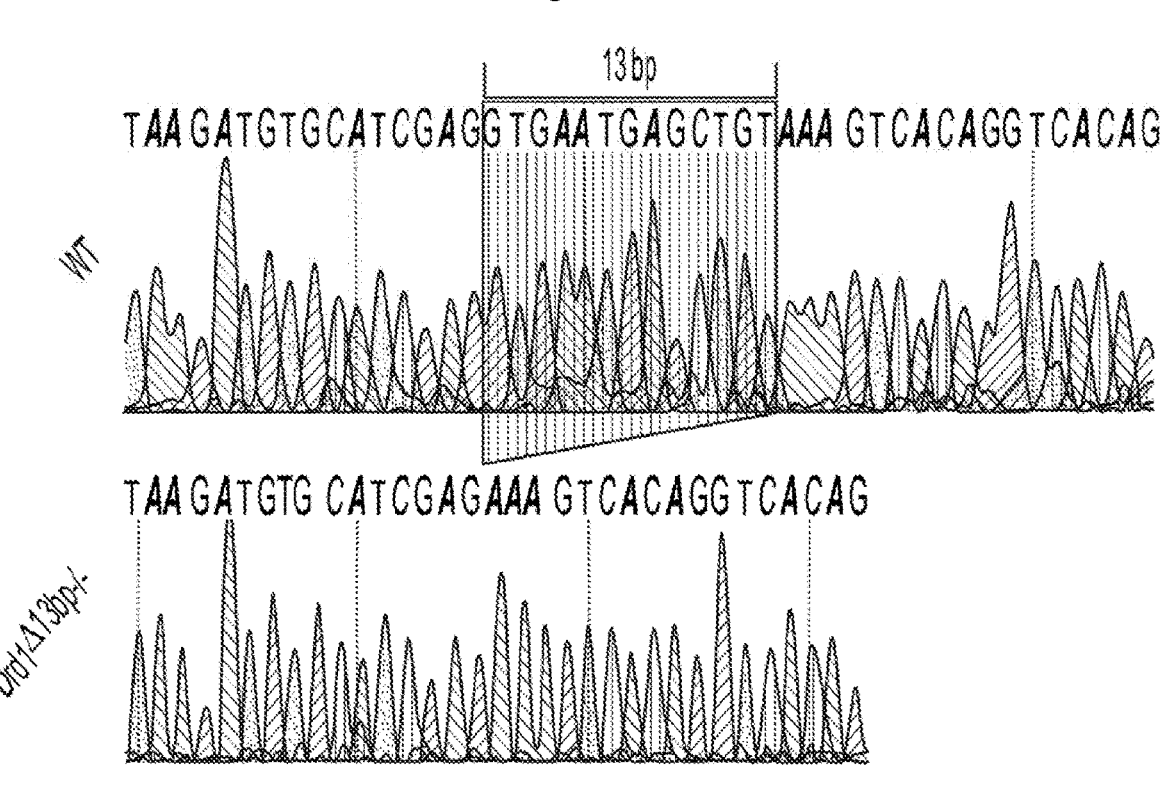
Figure 5E:
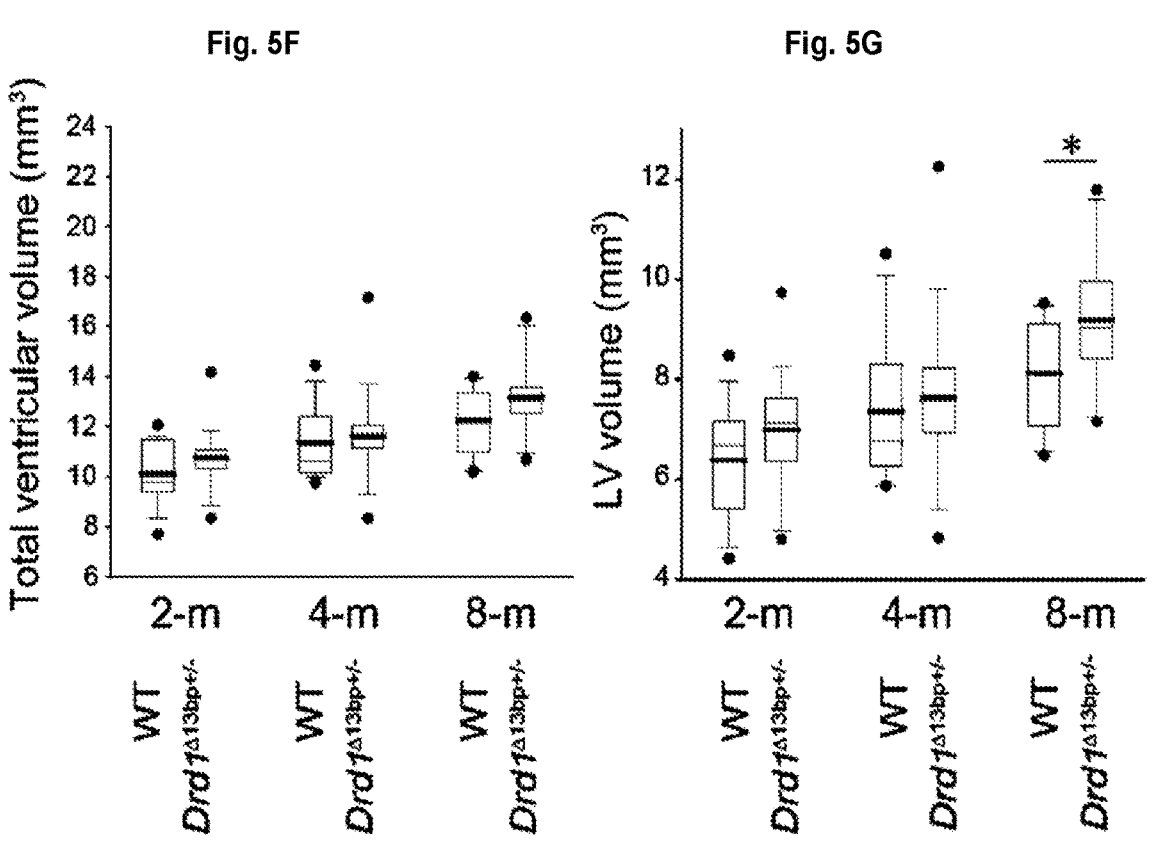
Figure 12A:
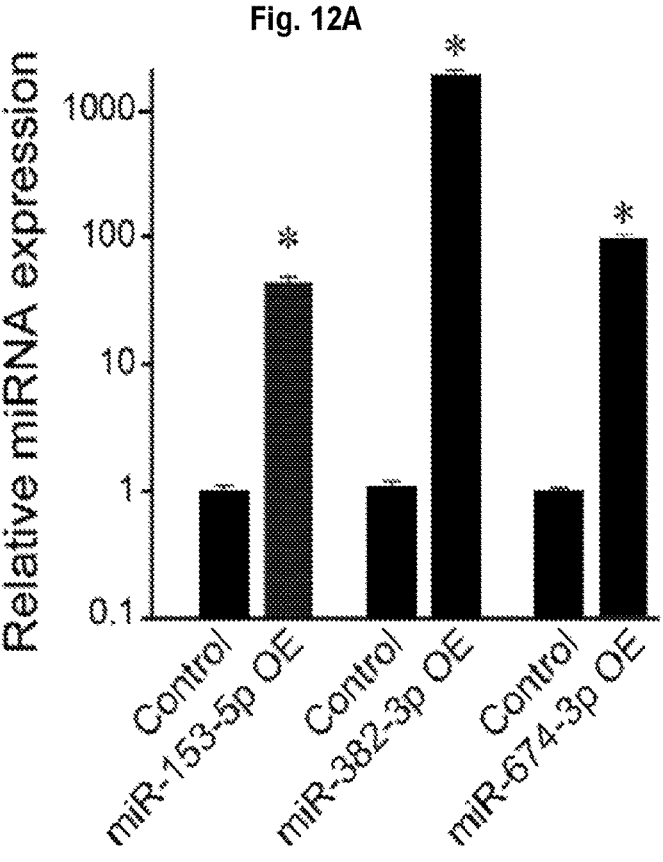
FIGS. 12A-12B. Conformation of Recombinant miRNA Overexpression and Its Specificity against Drd1 3'UTR, Related to FIGS. 5A-5G.
Figure 12B:
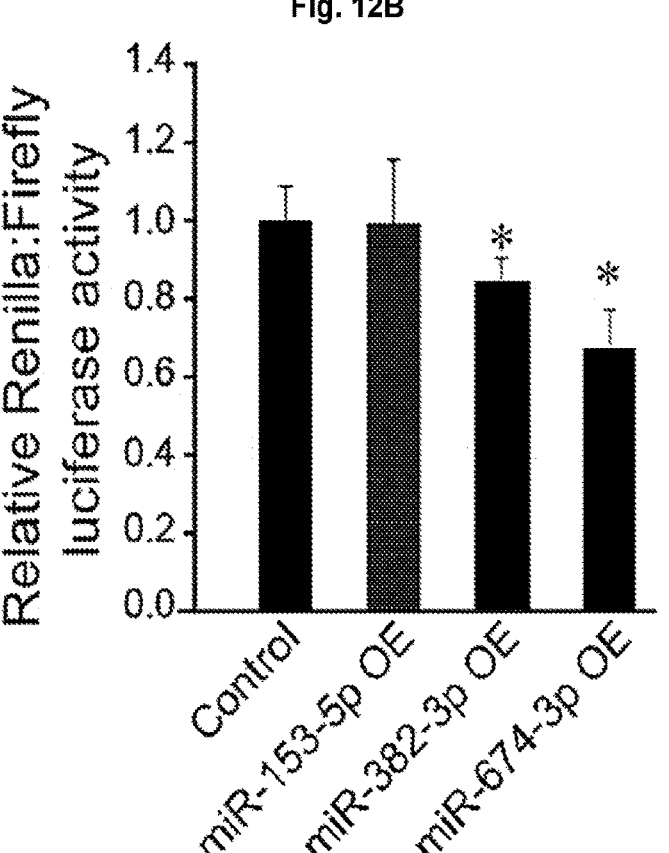

Example 6: Depleting miR-382-3p or miR-674-3p
or Deleting their Seed Sites on Drd1 3'UTR
Decelerates Ependymal Ciliary Beating and
Mediates Ventriculomegaly To identify the miRNAs involved in the Dgcr8-miRNA-
Drd1 mechanism, miRNA microarray analysis was per-
formed in the LV wall of 8-month-old Dgcr8+/− and WT
littermates. Among the miRNAs that potentially target the 3'
untranslated region (UTR) of the Drd1 transcript (on the
basis of the miRWalk and TargetScan miRNA-target-prediction algorithms), only three miRNAs (miR-153-5p, miR-382-3p, and miR-674-3p) were significantly decreased in Dgcr8$^{+/-}$ mice (FIG. 5A, Table 3). The RT-qPCR analysis verified that the levels of all three Drd1-targeting miRNAs were significantly reduced in Dgcr8$^{+/-}$ mice compared to WT mice (FIG. 5B). All three miRNAs were substantially enriched in the brain, including the LV wall, compared to non-brain areas such as kidney or liver (FIG. 5C). Of the three identified miRNAs, overexpression of two, miR-382-3p (miR-382-3p OE) and miR-674-3p (miR-674-3p OE), decreased the levels of Drd1 transcripts in vitro (FIG. 12). Therefore, in further experiments these two miRNAs were focused on as the mediators of the Dgcr8-miRNA-Drd1 mechanism. The miR-382-3p is conserved across species, including humans and mice, but miR-674-3p does not have a human homologue. Interestingly, the predicted miRNA-target sites of miR-382-3p and miR-674-3p overlapped on the Drd1 3'UTR (FIG. 5D). The 13-bp sequence containing seed sequences from both miRNAs is unique throughout all 3'UTRs of reference-sequence genes in the mouse genome (GRCm38/mm10 assembly). The miR-674-3p has an additional 7-bp binding site in the Drd1 3'UTR (FIG. 5D). To test whether the miR-382-3p- or miR-674-3p-binding sites are involved in ventricular enlargement, mice with deletions of the 13-bp seed site (Drd1$^{\Delta 13bp}$) and the 7-bp seed site (Drd1$^{\Delta 7bp}$), respectively, in the Drd1 3'UTR were generated by using the CRISPR/Cas9 approach. Both Drd1$^{\Delta 7bp+/-}$ and Drd1$^{\Delta 13bp+/-}$ mice developed normally and had no detectible gross abnormalities compared to their respective WT controls. Data on ventricular volumes in Drd1$^{\Delta bp+/-}$ mice were inconclusive due to a small number of animals tested. However, Drd1$^{\Delta 13bp+/-}$ mice showed age-dependent and region-specific ventricular enlargement (FIGS. 5E-5G). Specifically, 8-month-old but not younger Drd1$^{\Delta 13bp+/-}$ mice had significantly enlarged LVs compared to WT littermates (FIGS. 5F, 5G, Table 4). This suggests that the unique 13-bp miR-382-3p/miR-674-3p Drd1 seed site mediates the effect of these miRNAs in the ventricular-enlargement phenotype.

TABLE 3

Altered miRNA levels in the lateral ventricle wall of 8-month-old Dgcr8$^{+/-}$ mice compared to that of their respective WT littermates[a]

| miRNA ID | Dgcr8$^{+/-}$ vs. WT, log$_2$ (FC) | Dgcr8$^{+/-}$ vs. WT, p-value |
|---|---|---|
| miR-374c-5p | −0.7411 | 3.860E−05 |
| miR-337-5p | −0.6584 | 3.990E−09 |
| miR-130b-3p | −0.6524 | 2.970E−05 |
| miR-299b-5p | −0.6510 | 1.800E−05 |
| miR-337-3p | −0.6427 | 8.400E−08 |
| miR-329-3p | −0.6317 | 1.330E−06 |
| miR-672-5p | −0.6314 | 4.560E−05 |
| miR-409-3p | −0.5983 | 4.960E−05 |
| miR-674-3p | −0.5980 | 1.720E−06 |
| miR-379-3p | −0.5889 | 6.070E−06 |
| miR-873a-5p | −0.5875 | 2.980E−05 |
| miR-488-3p | −0.5769 | 2.940E−04 |
| miR-540-5p | −0.5761 | 2.550E−05 |
| miR-323-3p | −0.5757 | 2.470E−07 |
| miR-379-5p | −0.5729 | 5.990E−06 |
| miR-378d | −0.5637 | 1.080E−06 |
| miR-378b | −0.5582 | 2.110E−06 |
| miR-382-3p | −0.5511 | 1.000E−05 |
| miR-544-5p | −0.5479 | 1.190E−05 |
| miR-382-5p | −0.5265 | 3.081E−03 |
| miR-411-3p | −0.5244 | 3.510E−06 |
| miR-582-3p | −0.5198 | 1.126E−03 |
| miR-467b-5p | −0.5180 | 1.930E−06 |

TABLE 3-continued

Altered miRNA levels in the lateral ventricle wall of 8-month-old Dgcr8$^{+/-}$ mice compared to that of their respective WT littermates[a]

| miRNA ID | Dgcr8$^{+/-}$ vs. WT, log$_2$ (FC) | Dgcr8$^{+/-}$ vs. WT, p-value |
|---|---|---|
| miR-708-3p | −0.5136 | 6.870E−06 |
| miR-346-5p | −0.5071 | 3.610E−06 |
| miR-874-3p | −0.4970 | 1.970E−06 |
| miR-376c-3p | −0.4954 | 5.040E−05 |
| miR-541-5p | −0.4910 | 2.840E−05 |
| miR-598-3p | −0.4845 | 4.623E−03 |
| miR-153-5p | −0.4784 | 1.650E−07 |
| miR-378a-3p | −0.4762 | 2.130E−06 |
| miR-192-5p | −0.4760 | 1.193E−03 |
| miR-409-5p | −0.4759 | 1.350E−04 |
| miR-592-5p | −0.4725 | 2.156E−02 |
| miR-340-3p | −0.4680 | 5.830E−05 |
| miR-378a-5p | −0.4601 | 9.080E−07 |
| miR-674-5p | −0.4594 | 1.270E−06 |
| miR-490-3p | −0.4589 | 4.760E−04 |
| miR-380-3p | −0.4571 | 3.446E−03 |
| miR-411-5p | −0.4569 | 6.690E−07 |
| miR-335-3p | −0.4509 | 1.040E−04 |
| miR-342-5p | −0.4443 | 3.148E−03 |
| miR-532-5p | −0.4436 | 7.040E−05 |
| miR-185-5p | −0.4326 | 1.660E−04 |
| miR-212-5p | −0.4322 | 9.030E−04 |
| miR-764-3p | −0.4288 | 3.511E−02 |
| miR-505-5p | −0.4215 | 5.152E−03 |
| miR-325-3p | −0.4208 | 9.650E−05 |
| miR-377-3p | −0.4172 | 1.580E−05 |
| miR-872-5p | −0.4162 | 1.110E−04 |
| miR-467a-3p | −0.4015 | 8.680E−05 |
| miR-764-5p | −0.3963 | 8.540E−04 |
| miR-7118-5p | 0.4149 | 1.866E−02 |
| miR-690 | 0.4272 | 6.340E−03 |
| miR-1897-5p | 0.4276 | 1.896E−03 |
| miR-680 | 0.4285 | 1.800E−05 |
| miR-6931-5p | 0.4313 | 7.800E−04 |
| miR-7018-5p | 0.4319 | 7.320E−04 |
| miR-1897-3p | 0.4362 | 7.150E−04 |
| miR-3473g | 0.4504 | 1.873E−02 |
| miR-1895 | 0.4535 | 2.510E−05 |
| miR-211-3p | 0.4605 | 4.570E−04 |
| miR-5622-3p | 0.4787 | 2.966E−02 |
| miR-7042-5p | 0.4934 | 1.915E−03 |
| miR-7036a-5p | 0.5053 | 3.000E−04 |
| miR-7686-5p | 0.5173 | 3.171E−03 |
| miR-3960 | 0.5425 | 6.950E−04 |
| miR-8117 | 0.5440 | 9.120E−04 |
| miR-7002-5p | 0.5516 | 7440E−04 |
| miR-6769b-5p | 0.5536 | 3.223E−03 |
| miR-7047-5p | 0.5748 | 2.489E−03 |
| miR-8110 | 0.5756 | 9.110E−04 |
| miR-5126 | 0.5940 | 9.900E−04 |
| miR-6997-5p | 0.6810 | 9.220E−03 |

[a]Only miRNAs with p < 0.05 and log$_2$ fold change (FC) > ±0.4 are shown. Grey shading indicates the miRNAs predicted to target the Drd1 transcript. The microarray data have been deposited in the NCBI GEO database under accession number GSE123560.

TABLE 4

Comparison of ventricular volumes in 8-month-old WT and Drd1$^{\Delta 13bp+/-}$ mice

| Ventricle Volume[a] | Mean volume ± SD (mm$^3$) | | |
|---|---|---|---|
| | WT (n-12) | Drd1$^{\Delta 13bp+/-}$ (n = 11) | p-value[b] |
| Fourth | 0.71 ± 0.11 | 0.76 ± 0.15 | 0.33 |
| Aqueduct | 0.50 ± 0.09 | 0.49 ± 0.13 | 0.86 |
| Third | 2.65 ± 0.29 | 2.50 ± 0.27 | 0.20 |

TABLE 4-continued

Comparison of ventricular volumes in 8-month-old WT and Drd1$^{\Delta 13bp+/-}$ mice

| Ventricle Volume[a] | Mean volume ± SD (mm³) | | |
|---|---|---|---|
| | WT (n-12) | Drd1$^{\Delta 13bp+/-}$ (n = 11) | p-value[b] |
| Left lateral | 4.10 ± 0.90 | 4.54 ± 0.97 | 0.28 |
| Right lateral | 4.03 ± 0.66 | 4.65 ± 0.51 | 0.02 |
| LVs (combined) | 8.13 ± 0.31 | 9.19 ± 0.40 | 0.04 |
| Total | 12.23 ± 1.31 | 13.15 ± 1.47 | 0.12 |

Figure 13A:
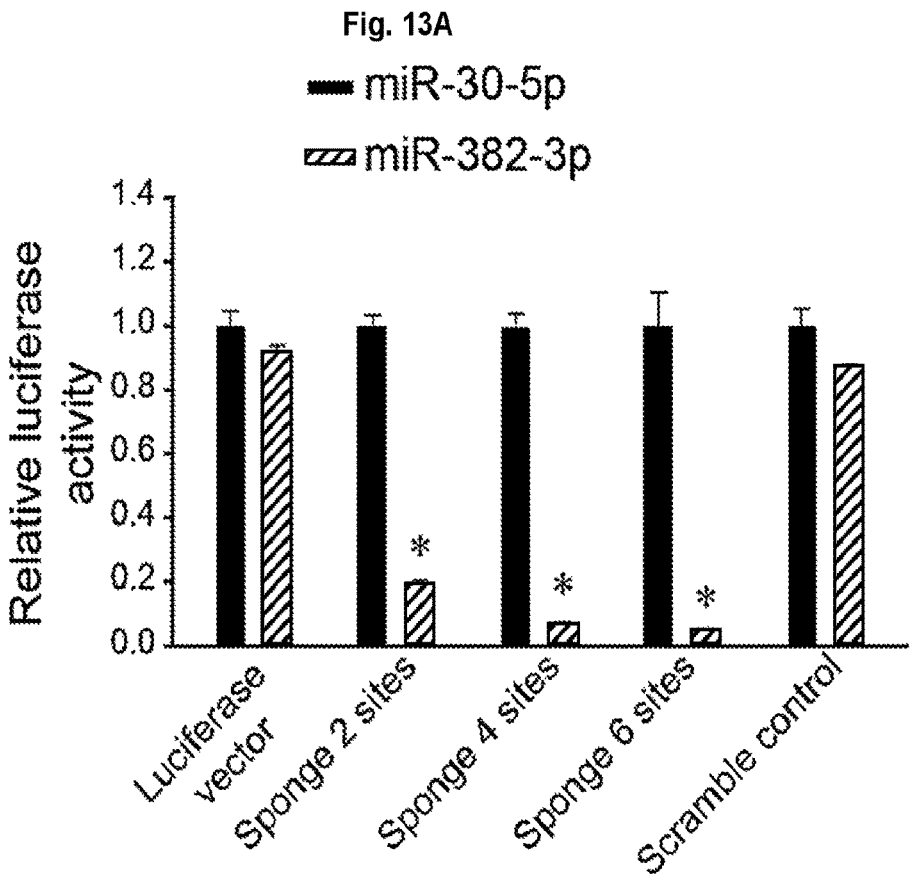
FIGS. 13A-13B. Validation of the miRNA Sponges, Related to FIGS. 6A-6H.
Figure 13B:
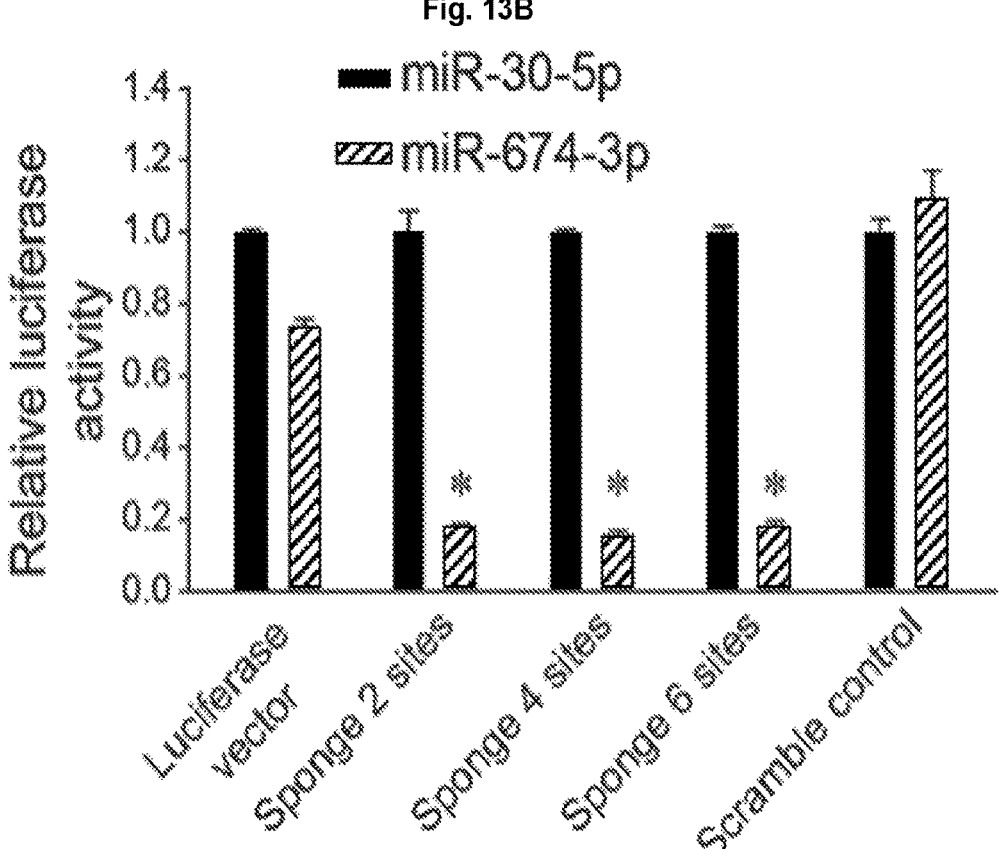
Figure 14A:
FIGS. 14A-14B. In Vivo Expression of AAV1-miRNA-GFP in the Ependymal Cells, Related to FIGS. 6A-6H.
Figure 14A:
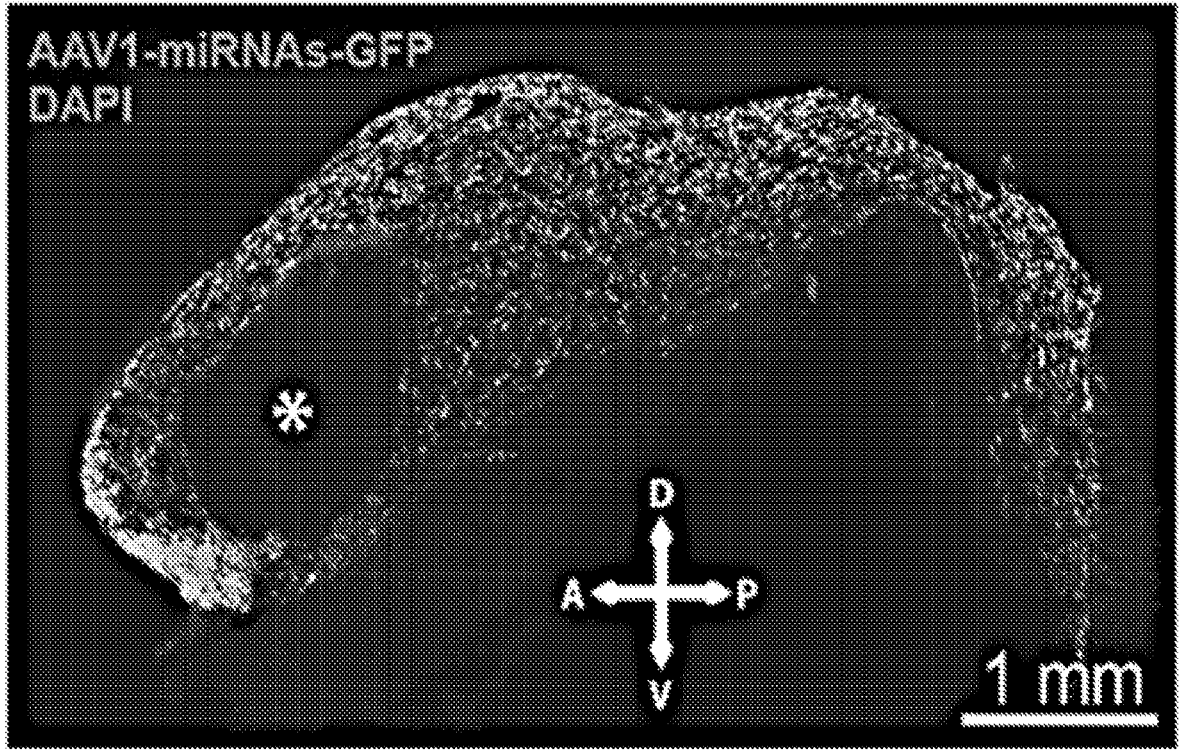
Figure 14B:
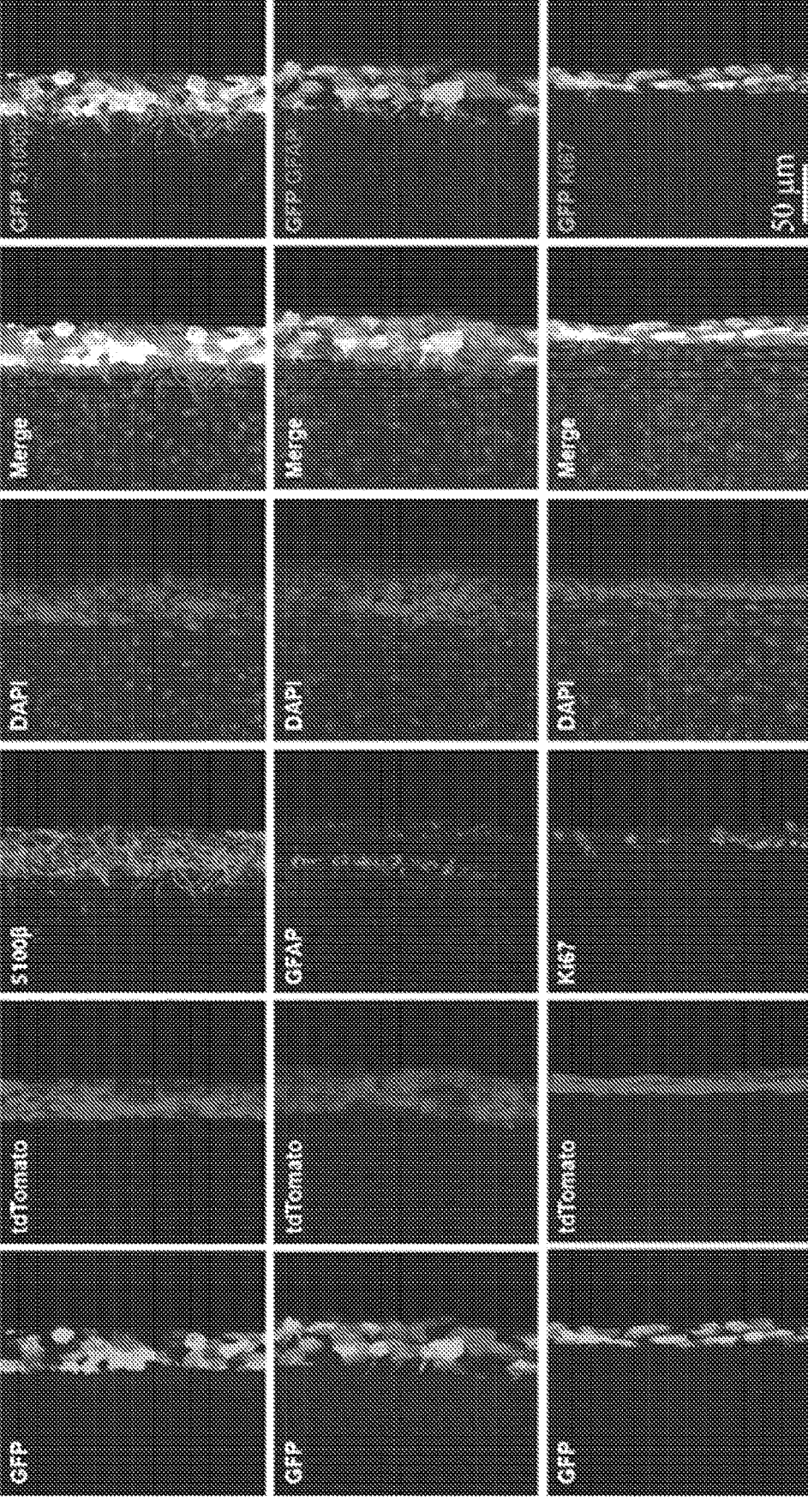

[a]Volumes were measured using a 7 T Bruker ClinScan system.
[b]P-values were calculated by two-tailed Student's t-test. Significant p-values are indicated in bold.
Abbreviations:
LVs, lateral ventricals,
WT, wild-type To test if depletion of miR-382-3p or miR-674-3p mimics the cilia deceleration and ventricular enlargement in WT mice in vivo, sponges specific for miR-382-3p or miR-674-3p were generated (Chun et al., 2017; Small and Olson, 2011). The miR-382-3p or miR-674-3p effectively inhibited reporters containing the sponge sequence in vitro, as measured by the luciferase assay (FIG. 13). To deliver these sponges in vivo, the recombinant adeno-associated virus serotype 1 (AAV1) encoding GFP under the ubiquitous CAG promoter (AAV1-CAG-GFP) was generated. AAV1-CAG-GFP was injected intracerebroventricularly in Foxj1$^{Cre}$;Ai14 mice, which express tdTomato in ependymal cells. Approximately 3 weeks after injection, robust co-labeling of GFP with tdTomato was detected, indicating that the AAV1 efficiently and specifically infected the ependymal cells (FIGS. 6A and 14). The GFP signal was colocalized with tdTomato⁺ and S100β⁺ ependymal cells but not with neural progenitor markers GFAP and Ki67 (FIG. 14B), indicating that ependymal cells have a strong affinity for AAV1, as previously shown (Yamazaki et al., 2014). In contrast, AAV5 viruses were less specific and infected ependymal cells and other cells, including neurons in other brain areas.

Figure 6E:
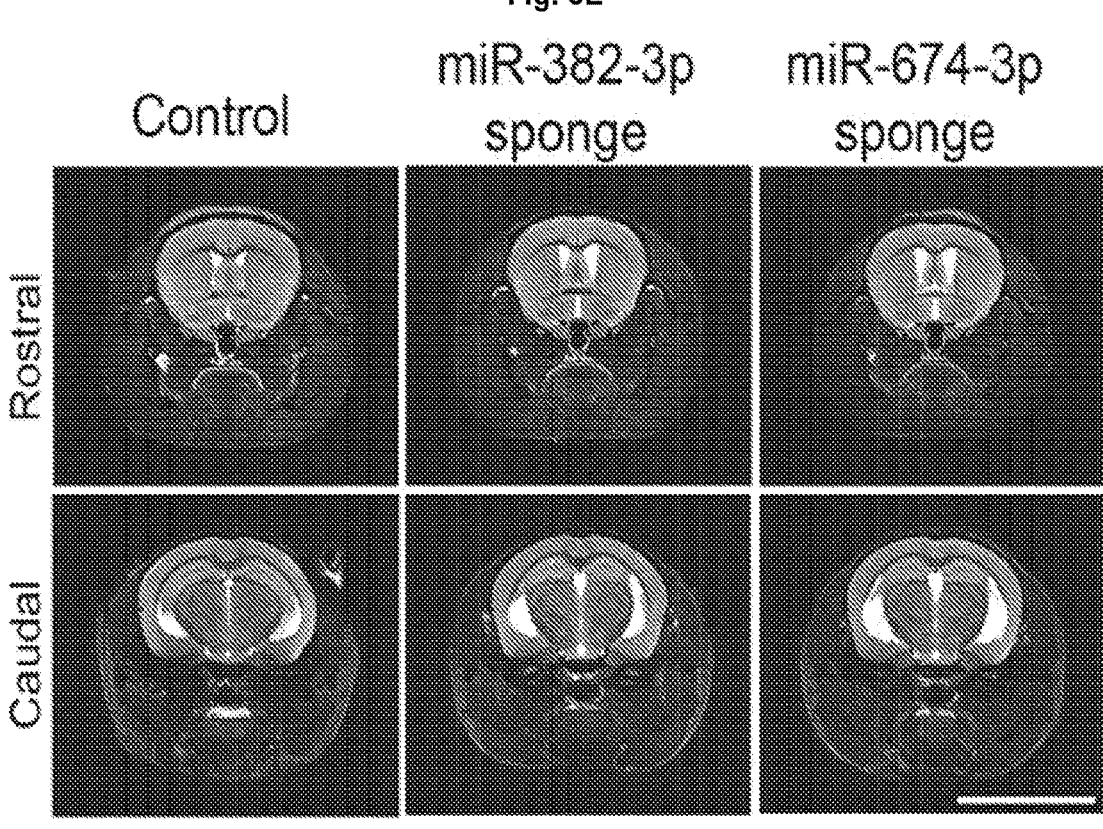

To use this AAV1 tropism for specific molecular manipulations in ependymal cells, an AAV1 containing miR-382-3p, miR-674-3p sponges, or scramble control (AAV1-CAG-GFP-miR-382-3p sponge, AAV1-CAG-GFP-miR-674-3p sponge, and AAV1-CAG-GFP-scramble) was constructed. The infection with AAV1 encoding the miR-382-3p or miR-674-3p sponge significantly reduced the level of respective miRNAs and increased the expression of the Drd1 transcript in the LV wall of WT mice (FIGS. 6B-6D). The miR-674-3p sponge expression in ependymal cells of WT mice resulted in ventriculomegaly, including increased volume of the TV (FIGS. 6E-6G, Table 5). The miR-382-3p sponge increased the volume of the TV but did not affect the total ventricular volume (FIG. 6G, Table 4). These significant differences in ventricle size were not accompanied by other aberrant neuroanatomical features or changes in ependymal planar polarity (FIG. 15). Furthermore, the AAV1 expressing the miR-674-3p sponge significantly reduced the ependymal CBF compared to control virus in WT mice (FIG. 6H). Ependymal CBF also appeared to be reduced when ependymal cells were infected with AAV1 expressing the miR-382-3p sponge, but that reduction was not significant. Together, these results suggest that depletion of miR-382-3p or miR-674-3p, which occurs in Dgcr8⁺/⁻ mice, slows ependymal CBF and induces ventriculomegaly.

TABLE 5

Comparison of ventricular volumesa in 8-month-old WT mice treated with AAV sponges

| Ventricle Volume | Mean volume ± SD after injection of an AAV sponge | | | | |
|---|---|---|---|---|---|
| | Control (n = 27) | miR-382-3p (n = 28) | P-value[b] | miR-674-3p (n = 28) | P-value[b] |
| Fourth | 0.91 ± 0.21 | 0.81 ± 0.17 | 0.05 | 0.86 ± 0.20 | 0.34 |
| Aqueduct | 0.59 ± 0.10 | 0.54 ± 0.16 | 0.12 | 0.45 ± 0.14 | <0.001 |
| Third | 2.56 ± 0.40 | 2.84 ± 0.39 | 0.01 | 3.99 ± 1.07 | <0.001 |
| Left lateral | 3.86 ± 0.80 | 4.02 ± 0.74 | 0.46 | 4.84 ± 1.17 | <0.001 |
| Right lateral | 4.11 ± 0.81 | 4.37 ± 0.61 | 0.14 | 5.14 ± 1.28 | <0.001 |
| Total | 12.38 ± 1.56 | 12.85 ± 1.65 | 0.28 | 15.59 ± 2.51 | <0.001 |

[a]Volumes were measured (in mm³) using a 7 T Bruker ClinScan system.
[b]P-values were calculated by two-tailed Student's t-test. Significant p-values are indicated in bold.

Example 7: Replenishing miR-382-3p or miR-674-3p Rescues the Cilia-Beating Deficit and Ventriculomegaly in 22q11DS Mice Given that depletion of miR-382-3p or miR-674-3p leads to ventriculomegaly in 22q11DS mice, the inventors sought to rescue this phenotype by overexpressing these miRNAs in the ependymal cells. To this end, AAV1 expressing miR-382-3p or miR-674-3p with GFP (AAV1-miR-382-3p OE and AAV1-miR-674-3p OE) was constructed. After AAV1-miR-382-3p OE or AAV1-miR-674-3p OE intracerebroventricularly was injected, the expression of each miRNA was increased, compared to the levels in mice that received injections with a control virus (FIG. 16A, B). This coincided with reduced Drd1 mRNA levels in the LV wall of Df(16)1/+ mice (FIG. 16C). Neither AAV1-miR-382-3p OE nor AAV1-miR-674-3p OE affected Drd1 mRNA levels in WT mice. However, overexpression of AAV1-miR-674-3p significantly reduced Drd1 mRNA levels in Df(16)1/+ mice (p<0.001), which became indistinguishable from WT. Drd1 mRNA levels in Df(16)1/+ mice were also significantly reduced (p<0.001) after injection of AAV1-miR-382-3p OE but still remained higher than in WT mice (FIG. 16C).

Figure 7A:
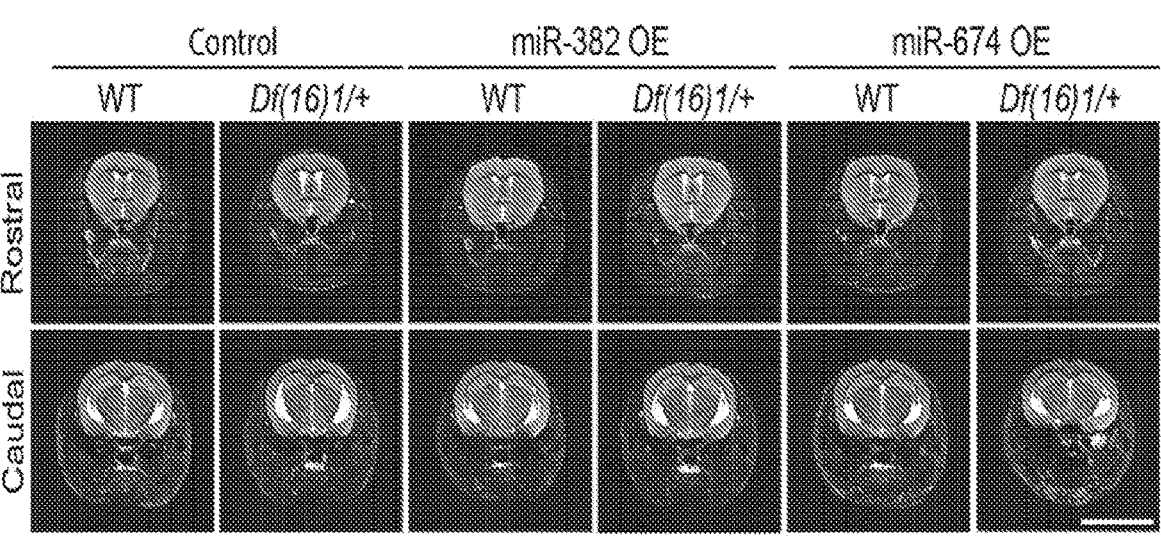
Figure 7A:
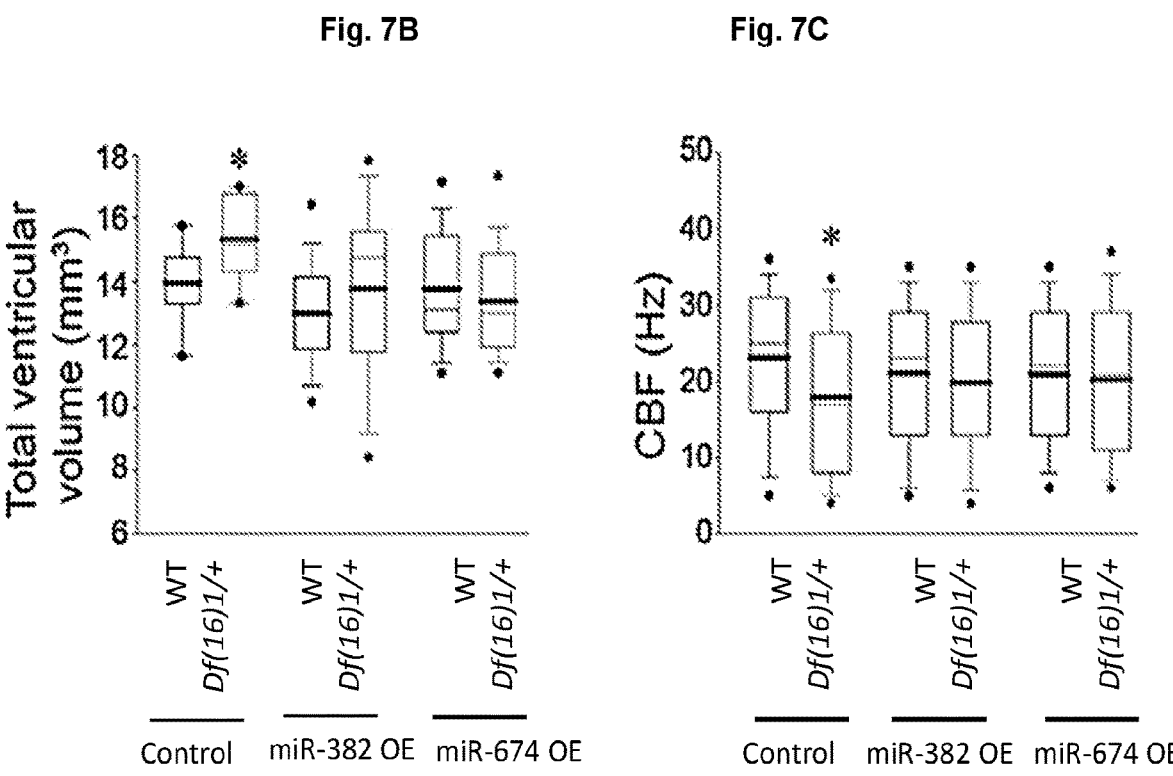

AAV1-miR-382-3p OE and AAV1-miR-674-3p OE but not a control AAV1 injected intracerebroventricularly into 2- to 3-month-old Df(16)1/+ mice prevented ventriculomegaly measured at 8 months of age (FIGS. 7A-7B, Table 6). The total ventricular volume was substantially larger in Df(16)1/+ mutants than in WT mice when both genotypes were injected with the control virus. However, this ventricular enlargement was eliminated when WT and Df(16)1/+ mice were injected with AAV1-miR-382-3p OE or AAV1-miR-674-3p OE (FIG. 7B). AAV1-miR-382-3p OE and AAV1-miR-674-3p OE did not affect ventricular volumes in WT mice, but ventricular volume was significantly smaller in Df(16)1/+ mutants injected with AAV1-miR-674-3p OE than those injected with control AAV1 (p=0.006). A trend of decreased total ventricular volume was also observed in Df(16)1/+ mice injected with AAV1-miR-382-3p OE, but that decrease was not significant (p=0.055) (Table 6).

TABLE 6

Comparison of ventricular volumes[a] in 8-month-old mice treated with AAV1s that overexpressed microRNAs in ependymal cells Mean volume ± SD after infection with AAV1

| | Control AAV1 | | | miR-382P-3p OE AAV1 | | | | miR-674-3p OE AAV1 | | | |
|---|---|---|---|---|---|---|---|---|---|---|---|
| Ventricle Volume | WT (n = 9) | Df(16)1/+ (n = 9) | P-value[b] | WT (n = 21) | P-value | Df(16)1/+ (n = 17) | P-value[b] | WT (n = 20) | P-value[b] | Df(16)1/+ (n = 16) | P-value[b] |
| Fourth | 0.94 ± 0.19 | 0.76 ± 0.18 | 0.045 | 0.94 ± 0.18 | 0.97 | 0.95 ± 0.22 | 0.96 | 0.86 ± 0.27 | 0.42 | 0.81 ± 0.19 | 0.09 |
| Aqueduct | 0.69 ± 0.18 | 0.55 ± 0.10 | 0.07 | 0.58 ± 0.17 | 0.14 | 0.51 ± 0.12 | 0.01 | 0.61 ± 0.14 | 0.21 | 0.59 ± 0.22 | 0.27 |
| Third | 2.81 ± 0.38 | 3.07 ± 0.52 | 0.25 | 2.60 ± 0.34 | 0.15 | 2.82 ± 0.59 | 0.97 | 2.64 ± 0.46 | 0.33 | 2.55 ± 0.49 | 0.17 |
| Left lateral | 3.99 ± 0.63 | 4.86 ± 1.03 | 0.046 | 3.63 ± 0.85 | 0.26 | 4.06 ± 1.16 | 0.88 | 3.85 ± 0.96 | 0.29 | 4.00 ± 0.72 | 0.99 |
| Right lateral | 3.98 ± 0.67 | 4.65 ± 0.56 | 0.04 | 3.77 ± 0.66 | 0.43 | 4.01 ± 1.29 | 0.94 | 4.35 ± 0.92 | 0.29 | 3.91 ± 0.93 | 0.84 |
| Total | 12.76 ± 1.17 | 14.14 ± 1.29 | 0.03 | 11.79 ± 1.56 | 0.11 | 12.58 ± 2.68 | 0.86 | 12.56 ± 1.80 | 0.77 | 12.18 ± 0.84 | 0.37 |
| | WT (n = 10) | Dgcr8[+/−] (n = 9) | P-value[c] | WT (n = 23) | P-value[c] | Dgcr8[+/−] (n = 24) | P-value[c] | WT (n = 17) | P-value[c] | Dgcr8[+/−] (n = 17) | P-value[c] |
| Fourth | 0.88 ± 0.23 | 0.99 ± 0.11 | 0.20 | 0.87 ± 0.17 | 0.80 | 0.84 ± 0.24 | 0.59 | 0.83 ± 0.19 | 0.54 | 0.84 ± 0.22 | 0.58 |
| Aqueduct | 0.59 ± 0.14 | 0.54 ± 0.13 | 0.37 | 0.56 ± 0.09 | 0.43 | 0.55 ± 0.13 | 0.44 | 0.61 ± 0.18 | 0.96 | 0.61 ± 0.12 | 0.80 |
| Third | 2.96 ± 0.38 | 3.09 ± 0.44 | 0.50 | 2.70 ± 0.60 | 0.26 | 2.80 ± 0.61 | 0.44 | 2.77 ± 0.39 | 0.24 | 2.80 ± 0.46 | 0.36 |
| Left lateral | 3.76 ± 0.39 | 4.19 ± 0.51 | 0.055 | 4.10 ± 1.25 | 0.74 | 4.18 ± 1.19 | 0.56 | 4.05 ± 0.53 | 0.15 | 4.12 ± 0.69 | 0.15 |
| Right lateral | 4.09 ± 0.49 | 5.10 ± 0.96 | 0.02 | 4.30 ± 1.19 | 0.89 | 4.52 ± 1.15 | 0.44 | 4.38 ± 0.63 | 0.22 | 4.33 ± 0.69 | 0.35 |
| Total | 12.52 ± 0.94 | 14.27 ± 1.43 | 0.005 | 12.59 ± 3.12 | 0.95 | 13.17 ± 2.55 | 0.72 | 12.97 ± 1.36 | 0.37 | 13.04 ± 1.57 | 0.36 |

[a]Volumes were measured (in mm$^3$) using a 7 T Bruker ClinScan system.
[b]P-values indicate a comparison of ventricular volume with that measured in WT mice injected with Control AAV1, as calculated by two-tailed Student's t-test. Significant p-values are indicated in bold.
[c]P-values indicate a comparison of ventricular volume with that measured in Dgcr8[+/+] mice injected with Control AAV1, as calculated by two- tailed Student's t-test. Significant p-values are indicated in bold.

The normalization of the ventricular size in Df(16)1/+ mice injected with AAV1-miR-674-3p OE or AAV1-miR-382-3p OE was accompanied by the rescue of ciliary beating (FIG. 7C). Ependymal CBF was significantly lower in Df(16)1/+ mice than WT littermates when both genotypes were injected with the control virus. However, this difference was eliminated when mice were injected with either AAV1-miR-674-3p OE or AAV1-miR-382-3p OE. Similar to the ventricular volume, ependymal CBF in WT mice was not affected by AAV1-miR-674-3p OE or AAV1-miR-382-3p OE. However, AAV1-miR-674-3p OE significantly increased ependymal CBF in Df(16)1/+ mice (p=0.04). The CBF in Df(16)1/+ mice injected with AAV1-miR-382-3p OE also appeared to be faster than that in mice injected with control virus, but the increase was not significant (p=0.08).

Figure 7D:
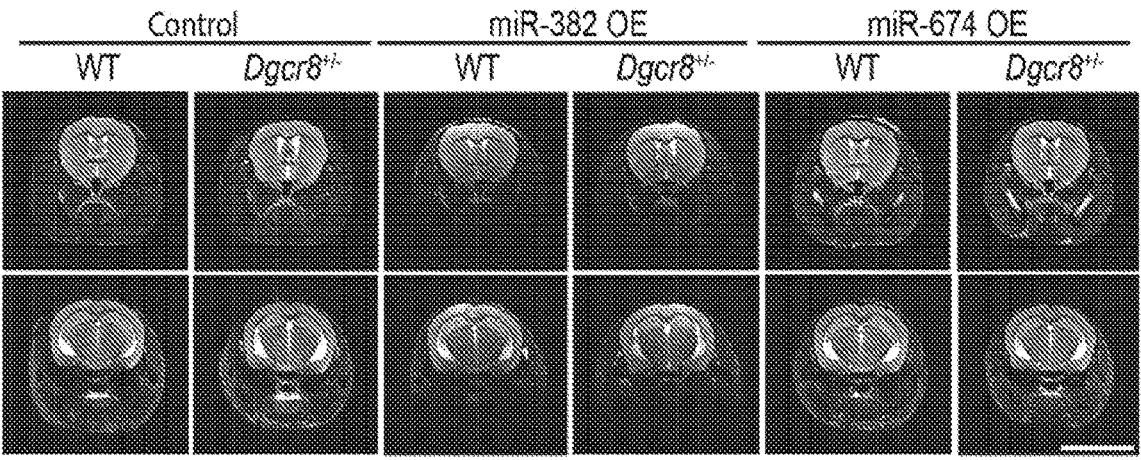
Figure 7D:
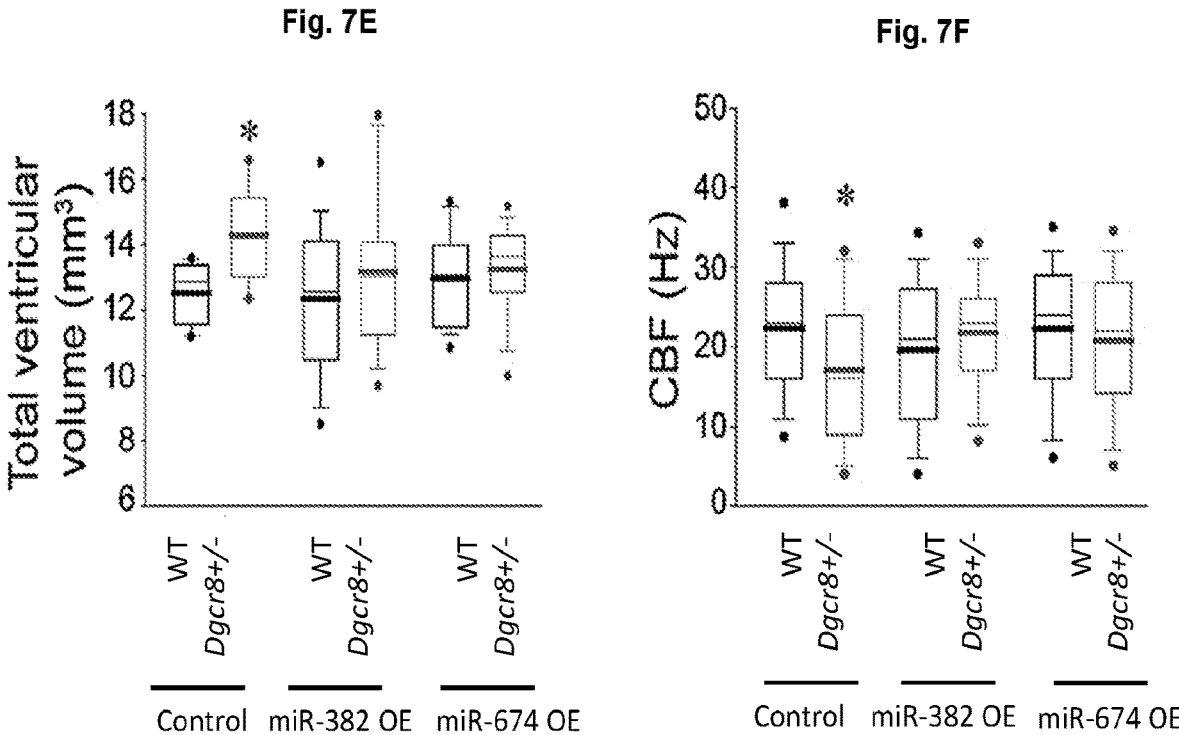

The normalization of the ventricular volume and CBF following intracerebroventricular injections of AAV1-miR-674-3p OE or AAV1-miR-382-3p OE was also observed in Dgcr8[+/−] mice (FIGS. 7D-7F). Dgcr8[+/−] mutants injected with the control virus had significantly enlarged ventricles and decreased CBF. However, injection of AAV1-miR-674-3p OE or AAV1-miR-382-3p OE eliminated these differences between WT and Dgcr8[+/−] littermates. In both measures, neither virus affected WT mice but rescued the defects in Dgcr8[+/−] mutants. AAV1-miR-674-3p OE significantly decreased the ventricular volume (p=0.04) and increased ependymal CBF (p<0.01) in Dgcr8[+/−] mice. AAV1-miR-382-3p OE appeared to decrease ventricular volume, but the change was not significant (p=0.08); however, it significantly increased CBF (p<0.001) in Dgcr8[+/−] mice (FIGS. 7E, 7F).

Together, these results indicate that Dgcr8 haploinsufficiency is a genetic factor contributing to progressive enlargement of the ventricles in 22q11DS mice. This ana- tomical change is accompanied by the deficit of ependymal ciliary motility, which is mediated by the Dgcr8-(miR-382-3p/miR-674-3p)-Drd1 mechanism.

CONCLUSIONS

Here the inventors identified a mechanism of progressive ventricular enlargement, which is one of the most replicable neuroanatomical findings in individuals with SCZ. SCZ patients often and consistently show LV enlargement during their first episode of SCZ and in chronic SCZ (van Erp et al., 2016; Fusar-Poli et al., 2013; Haijma et al., 2013). Ventricular enlargement is also routinely found in individuals and mouse models of 22q11DS (Campbell et al., 2006; Ellegood et al., 2014; Kempton et al., 2010; Machado et al., 2007; Simon et al., 2005; Sztriha et al., 2004), suggesting that in this aspect 22q11DS mice are valid models of SCZ-associated ventricular enlargement. Using these models, it was shown that haploinsufficiency of the 22q11DS gene Dgcr8, which is involved in miRNA biosynthesis, leads to depletion of miR-382-3p and miR-674-3p and elevation of Drd1 expression in the LV wall. It was also determined that in ependymal cells Drd1 is expressed on the motile cilia. Consequently, the Drd1 increase in ependymal cells reduces ependymal CBF, which is associated with progressive ventricular enlargement in 22q11DS mice.

Multiple factors may contribute to ventricular enlargement, including stenosis of the aqueduct of Sylvius, impaired CSF homeostasis, aging, certain diseases, and cilia dysfunction (Filis et al., 2017; Kahle et al., 2016; Lee, 2013; Todd et al., 2018). Aqueduct stenosis and abnormal production or adsorption of CSF can cause the most drastic changes in the ventricular volume, leading to hydrocephalus, especially during early development. There was no stenosis of the aqueduct in 22q11DS brains, indicating that this enlargement of ventricles was nonobstructive. CSF osmolality was also not changed in the mutant brains. The slow developmental trajectory of ventricular enlargement in 22q11DS mice starkly contrasts with that of rapidly developing congenital childhood hydrocephalus, a severe neurological disorder with high mortality (Del Bigio, 2010; Casey et al., 1997; Miyan et al., 2003; Vogel et al., 2012). It also contrasts with occasional sporadic hydrocephalus in mice, which is much more severe and evident at birth. Hydrocephalic animals develop severe lesions and die at 20-40 days of age (Vogel et al., 2012), but there is no abnormal mortality in 22q11DS mice at this age. In humans and mice, ventricular volumes progressively increase during normal aging (Apostolova et al., 2012; Long et al., 2012; Pfefferbaum et al., 2004); this enlargement also has been often observed in neurological disorders, such as Alzheimer disease, vascular dementia, and Parkinson disease (Kuller et al., 2005, 2016; Mak et al., 2017; Nestor et al., 2008). However, evidence of ventricular enlargement in SCZ is overwhelming and reported in more than 80% of SCZ studies (Shenton et al., 2001). The slowly progressing ventricular enlargement described here resembled that which occurs in schizophrenic patients (Brugger and Howes, 2017; van Erp et al., 2014, 2016; Kempton et al., 2010). Previous association studies suggest that a combination of genetic and environmental factors contribute to age-dependent ventriculomegaly (Horga et al., 2011; Kremen et al., 2012). Genetic influences on ventricular enlargement may increase with age: from 32% to 35% in childhood to about 75% in older age (Kremen et al., 2012). Polymorphisms in Neuregulin 1 and catechol-O-methyltransferase have been associated with ventriculomegaly in patients with first-episode psychosis (Crespo-Facorro et al., 2007; Mata et al., 2009).

The cumulative data show a strong association between aberrant ciliogenesis or ciliary beating and ventriculomegaly (Appelbe et al., 2013; Banizs et al., 2005; Friedland-Little et al., 2011; Ibañez-Tallon et al., 2004; Konjikusic et al., 2018; Lattke et al., 2012; Lechtreck et al., 2008; Lee, 2013; Matsuo et al., 2013; Swiderski et al., 2012; Tissir et al., 2010; Wang et al., 1995, 2016; Wilson et al., 2010; Wodarczyk et al., 2009). In the present study, a defect in cilia beating was detected that was associated with ventricular enlargement in 22q11DS mice. Slower motile cilia beating in 22q11DS mice may arise from structural or functional abnormalities. EM imaging revealed that 22q11DS mice have no structural defects in the motile cilium structure. Planar polarity in ependymal cells was also normal in Dgcr8$^{+/-}$ mice. The unidirectional flow of CSF is generated by the well-coordinated stroke of motile cilia and is thought to depend on the planar polarity of the cells (Bayly and Axelrod, 2011; Guirao et al., 2010; Hirota et al., 2010; Ohata et al., 2014; Tissir and Goffinet, 2013; Wallingford, 2010). Furthermore, no abnormalities were detected in SVZ neurogenesis (i.e., cell proliferation, apoptosis, neurogenesis, or neuronal migration into the olfactory bulb) in mutant mice. These findings suggest that slower ciliary beating observed in mutant mice arises from functional abnormalities.

Functional defects of motile cilia cause primary ciliary dyskinesia (PCD) (Praveen et al., 2015). PCD is associated with defects in ciliary ultrastructure and/or function of the components of the ciliary axoneme. The clinical features of PCD are present during the neonatal period and characterized by respiratory tract infections, chronic otitis media, situs inversus, male infertility, and in most severe cases, hydrocephalus (Praveen et al., 2015). Although hydrocephalus is not a consistent feature in PCD, several studies show a link between PCD and hydrocephalus in humans (al-Shroof et al., 2001; Berlucchi et al., 2012; Greenstone et al., 1984; Kosaki et al., 2004; Picco et al., 1993; De Santi et al., 1990; Vieira et al., 2012; Wessels et al., 2003) and mouse models (Banizs et al., 2005; Conductier et al., 2013; Ha et al., 2016; Ibañez-Tallon et al., 2004; Koschützke et al., 2015; Lechtreck et al., 2008; Lee et al., 2008; McKenzie et al., 2015). Despite these numerous studies, it is still not clear whether PCD-related abnormalities in ciliary function cause hydrocephalus. Similarly, it is not certain that slower ciliary beating causes enlarged ventricles in 22q11DS. Nonetheless, the rescue experiments restored the normal levels of both ciliary beating and the ventricular size in 22q11DS mice, and the mimicking experiments resulted in both deceleration of ciliary beating and enlarged LVs in WT mice, suggesting a link between ciliary function and ventricular size.

The study reveals a non-neuronal function of Drd1, specifically its role in motile ciliary beating in ependymal cells. The presence of dopamine receptors in ependymal cells and other cells in the subependymal zone and dopaminergic fibers that innervate the ventricular system have been previously reported (Hoglinger et al., 2004; Howard et al., 1998; Michaloudi and Papadopoulos, 1996; Tome et al., 2007). Dopaminergic signaling in non-neuronal cell populations in the adult subependymal zone may be mediated by paracrine mechanisms (Hoglinger et al., 2004). Drd1 expression was detected in the LV wall, including the ependymal cilia. Although it was found that both Drd1 and Drd2 are expressed in the LV wall, only Drd1 was detected on the motile cilia. Pharmacologic inhibition of Drd1 accelerates ependymal CBF in mutant mice and brings it to the WT level. This rescue experiment suggests an inverse relation between Drd1 levels in the ependymal cells and their CBF. Consistent with this hypothesis, pharmacological activation of Drd1 reduced ependymal CBF in WT mice. Several studies in different tissues have reported a role of cAMP in mechanisms of ciliary beating with various effects (Conductier et al., 2013; Doerner et al., 2015; Droguett et al., 2017; Genzen et al., 2009; Nguyen et al., 2001; Schmid et al., 2007), suggesting that although the structure and function of cilia appears to be conserved across different ciliated tissues, the mechanism regulating this function could be quite diverse (Salathe, 2007; Satir and Christensen, 2007). Canonical Drd1 signaling activates $G_s$ proteins and adenylyl cyclase, which generate cAMP. Consistent with the elevated Drd1 levels, cAMP levels were also higher in the LV wall of Dgcr8$^{+/-}$ mice. Thus, decreased ependymal CBF caused by Dgcr8 haploinsufficiency could be explained by elevated Drd1 and the cAMP-dependent pathway.

As part of the Microprocessor complex, Dgcr8 produces miRNA precursors (Denli et al., 2004; Gregory et al., 2004). Two Drd1-targeting miRNAs were identified that affect ependymal CBF and ventricular volume. Dgcr8 haploinsufficiency leads to depletion of multiple miRNAs in the LV walls. However, only two miRNAs (miR-382-3p and miR-674-3p) target the Drd1 3'UTR and regulate its expression. The mimicking and rescuing experiments suggested that the depletion of these two miRNAs is necessary and sufficient to slow ciliary beating and increase ventricular volume in 22q11DS mice. Indeed, depletion of these miRNAs in WT mice increased Drd1 expression, reduced ependymal CBF, and enlarged the brain ventricles. Conversely, replenishing miR-382-3p or miR-674-3p in ependymal cells eliminated the differences in ependymal CBF and ventricular size between WT and 22q11DS mice. These data suggest that miR-382-3p/miR-674-3p directly target Drd1 to mediate ventriculomegaly in 22q11DS. This hypothesis was confirmed by deleting the unique Drd1 13-bp seed site for miR-382-3p/miR-674-3p, which was sufficient to produce ventricular enlargement in LVs. These data strongly suggest that a Dgcr8-(miR-382-3p/miR-674-3p)-Drd1 mechanism in ependymal cells regulates ciliary beating and the stability of ventricular volumes. These data show that miR-382-3 and miR-674-3p are highly expressed in the brain, including the LV wall.

In summary, these data implicate a Dgcr8-(miR-382-3p/miR-674-3p)-Drd1 pathogenic mechanism of slower ciliary beating and ventricular enlargement in 22q11DS, a rare disease that substantially increases the risk of SCZ. These data indicate that replenishing miR-382-3p or miR-674-3p or inhibiting Drd1 in ependymal cells could be a potential therapeutic avenue for preventing progressive enlargement of brain ventricles, a robust and replicable neuroanatomical feature associated with neuropsychiatric disease.

REFERENCES 1. al-Shroof, M., Karnik, A. M., Karnik, A. A., Longshore, J., Sliman, N. A., and Khan, F. A. (2001). Ciliary dyskinesia associated with hydrocephalus and mental retardation in a Jordanian family. Mayo Clin. Proc. 76, 1219-1224.
2. Almeida, O. P., Howard, R. J., Levy, R., and David, A. S. (1995). Psychotic states arising in late life (late paraphrenia) psychopathology and nosology. Br J Psychiatry 166, 205-214.
3. Ann Ellis, E. (2006). Solutions to the Problem of Substitution of ERL 4221 for Vinyl Cyclohexene Dioxide in Spurr Low Viscosity Embedding Formulations. Micros. Today 14, 32-33.
4. Apostolova, L. G., Green, A. E., Babakchanian, S., Hwang, K S., Chou, Y.-Y., Toga, A. W., and Thompson, P. M. (2012). Hippocampal Atrophy and Ventricular Enlargement in Normal Aging, Mild Cognitive Impairment (MCI), and Alzheimer Disease. Alzheimer Dis. Assoc. Disord. 26, 17-27.
5. Appelbe, O. K., Bollman, B., Attarwala, A., Triebes, L. A., Muniz-Talavera, H., Curry, D. J., and Schmidt, J. V. (2013). Disruption of the mouse Jhy gene causes abnormal ciliary microtubule patterning and juvenile hydrocephalus. Dev. Biol. 382, 172-185.
6. Banizs, B., Pike, M M., Millican, C. L., Ferguson, W. B., Komlosi, P., Sheetz, J., Bell, P. D., Schwiebert, E. M., and Yoder, B. K. (2005). Dysfunctional cilia lead to altered ependyma and choroid plexus function, and result in the formation of hydrocephalus. Development 132, 5329-5339.
7. Bartel, D. P. (2009). MicroRNAs: target recognition and regulatory functions. Cell 136, 215-233.
8. Bassett, A. S., and Chow, E. W. (1999). 22q11 deletion syndrome: a genetic subtype of schizophrenia. Biol Psychiatry 46, 882-891.
9. Bassett, A. S., Chow, E. W., AbdelMalik, P., Gheorghiu, M., Husted, J., and Weksberg, R. (2003). The schizophrenia phenotype in 22q11 deletion syndrome. Am J Psychiatry 160, 1580-1586.
10. Bayly, R., and Axelrod, J. D. (2011). Pointing in the right direction: new developments in the field of planar cell polarity. Nat Rev Genet 12, 385-391.
11. Berlucchi, M., de Santi, M. M., Bertoni, E., Spinelli, E., Timpano, S., and Padoan, R. (2012). Ciliary aplasia associated with hydrocephalus: an extremely rare occurrence. Eur. Arch. Oto-Rhino-Laryngology 269, 2295-2299.

12. Del Bigio, M. R. (2010). Ependymal cells: biology and pathology. Acta Neuropathol 119, 55-73.
13. Brugger, S. P., and Howes, O. D. (2017). Heterogeneity and Homogeneity of Regional Brain Structure in Schizophrenia: A Meta-analysis. JAMA Psychiatry 74, 1104-1111.
14. Campbell, L. E., Daly, E., Toal, F., Stevens, A., Azuma, R., Catani, M., Ng, V., Van, A. T., Chitnis, X., Cutter, W., et al. (2006). Brain and behaviour in children with 22q11.2 deletion syndrome: a volumetric and voxel-based morphometry MRI study. Brain 129, 1218-1228.
15. Casey, A. T., Kimmings, E. J., Kleinlugtebeld, A. D., Taylor, W. A., Harkness, W. F., and Hayward, R. D. (1997). The long-term outlook for hydrocephalus in childhood. A ten-year cohort study of 155 patients. Pediatr Neurosurg 27, 63-70.
16. Chow, E. W., Mikulis, D. J., Zipursky, R. B., Scutt, L. E., Weksberg, R., and Bassett, A. S. (1999). Qualitative MRI findings in adults with 22q11 deletion syndrome and schizophrenia. Biol Psychiatry 46, 1436-1442.
17. Chow, E. W., Zipursky, R. B., Mikulis, D. J., and Bassett, A. S. (2002). Structural brain abnormalities in patients with schizophrenia and 22q11 deletion syndrome. Biol Psychiatry 51, 208-215.
18. Chow, E. W., Watson, M., Young, D. A., and Bassett, A. S. (2006). Neurocognitive profile in 22q11 deletion syndrome and schizophrenia. Schizophr Res 87, 270-278.
19. Christensen, M., Larsen, L. A., Kauppinen, S., and Schratt, G. (2010). Recombinant Adeno-Associated Virus-Mediated microRNA Delivery into the Postnatal Mouse Brain Reveals a Role for miR-134 in Dendritogenesis in Vivo. Front Neural Circuits. 3, 16.
20. Chun, S., Westmoreland, J. J., Bayazitov, I. T., Eddins, D., Pani, A. K., Smeyne, R. J., Yu, J., Blundon, J. A., and Zakharenko, S. S. (2014). Specific disruption of thalamic inputs to the auditory cortex in schizophrenia models. Science (80-.). 344, 1178-1182.
21. Chun, S., Du, F., Westmoreland, J. J., Han, S. B., Wang, Y. D., Eddins, D., Bayazitov, I. T., Devaraju, P., Yu, J., Mellado Lagarde, M. M., et al. (2017). Thalamic miR-382-3p and/or miR-674-3p mediates auditory thalamocortical disruption and its late onset in models of 22q11.2 microdeletion. Nat. Med. 23, 39-48.
22. Comaniciu, D., Ramesh, V., and Meer, P. (2003). Kernel-based object tracking. IEEE Trans. Pattern Anal. Mach. Intell. 25, 564-577.
23. Conductier, G., Brau, F., Viola, A., Langlet, F., Ramkumar, N., Dehouck, B., Lemaire, T., Chapot, R., Lucas, L., Rovère, C., et al. (2013). Melanin-concentrating hormone regulates beat frequency of ependymal cilia and ventricular volume. Nat. Neurosci. 16, 845-847.
24. Crespo-Facorro, B., Roiz-Santiáñez, R., Pelayo-Terán, J. M., Perez-Iglesias, R., Carrasco-Marín, E., Mata, I., González-Mandly, A., Jorge, R., and Vázquez-Barquero, J. L. (2007). Low-activity allele of Catechol-O-Methyltransferase (COMTL) is associated with increased lateral ventricles in patients with first episode non-affective psychosis. Prog. Neuropsychopharmacol. Biol. Psychiatry 31, 1514-1518.
25. Delling, M., DeCaen, P. G., Doerner, J. F., Febvay, S., and Clapham, D. E. (2013). Primary cilia are specialized calcium signalling organelles. Nature. 504, 311-314.
26. Denli, A. M., Tops, B. B. J., Plasterk, R. H. A., Ketting, R. F., and Hannon, G. J. (2004). Processing of primary microRNAs by the Microprocessor complex. Nature 432, 231-235.

27. Doerner, J. F., Delling, M., and Clapham, D. E. (2015). Ion channels and calcium signaling in motile cilia. Elife 4.

28. Droguett, K., Rios, M., Carreño, D. V., Navarrete, C., Fuentes, C., Villalón, M., and Barrera, N. P. (2017). An autocrine ATP release mechanism regulates basal ciliary activity in airway epithelium. J. Physiol. 595, 4755-4767.

29. Earls, L. R., Bayazitov, I. T., Fricke, R. G., Berry, R. B., Illingworth, E., Mittleman, G., and Zakharenko, S. S. (2010). Dysregulation of presynaptic calcium and synaptic plasticity in a mouse model of 22q11 deletion syndrome. J Neurosci 30.

30. Earls, L. R., Gaines Fricke, R., Yu, J., Berry, R. B., Baldwin, L. T., and Zakharenko, S. S. (2012). Age-dependent microRNA control of synaptic plasticity in 22q11 deletion syndrome and schizophrenia. J Neurosci 32.

31. Eliez, S., Schmitt, J. E., White, C. D., and Reiss, A. L. (2000). Children and adolescents with velocardiofacial syndrome: a volumetric MRI study. Am J Psychiatry 157, 409-415.

32. Ellegood, J., Markx, S., Lerch, J. P., Steadman, P. E., Genc, C., Provenzano, F., Kushner, S. A., Henkelman, R. M., Karayiorgou, M., and Gogos, J. A. (2014). Neuro-anatomical phenotypes in a mouse model of the 22q11.2 microdeletion. Mol Psychiatry 19, 99-107.

33. Eom, T. Y., Bayazitov, I. T., Anderson, K., Yu, J., and Zakharenko, S. S. (2017). Schizophrenia-Related Microdeletion Impairs Emotional Memory through MicroRNA-Dependent Disruption of Thalamic Inputs to the Amygdala. Cell Rep. 19, 1532-1544.

34. van Erp, T. G., Greve, D. N., Rasmussen, J., Turner, J., Calhoun, V. D., Young, S., Mueller, B., Brown, G. G., McCarthy, G., Glover, G. H., et al. (2014). A multi-scanner study of subcortical brain volume abnormalities in schizophrenia. Psychiatry Res 222, 10-16.

35. van Erp, T. G., Hibar, D. P., Rasmussen, J. M., Glahn, D. C., Pearlson, G. D., Andreassen, O. A., Agartz, I., West-lye, L. T., Haukvik, U. K., Dale, A. M., et al. (2016). Subcortical brain volume abnormalities in 2028 individuals with schizophrenia and 2540 healthy controls via the ENIGMA consortium. Mol Psychiatry 21, 585.

36. Felzenszwalb, P. F., Girshick, R. B., McAllester, D., and Ramanan, D. (2010). Object Detection with Discriminatively Trained Part-Based Models. IEEE Trans. Pattern Anal. Mach. Intell. 32, 1627-1645.

37. Filis, A. K., Aghayev, K., and Vrionis, F. D. (2017). Cerebrospinal Fluid and Hydrocephalus: Physiology, Diagnosis, and Treatment. Cancer Control 24, 6-8.

38. Flurkey, K., Currer, J. M., and Harrison, D. E. (2007). The Mouse in Aging Research. In The Mouse in Biomedical Research, J. G. Fox, and E. Al., eds. (Burlington, MA: American College Laboratory Animal Medicine (Elsevier)), pp. 637-672.

39. Franke, B., Stein, J. L., Ripke, S., Anttila, V., Hibar, D. P., van Hulzen, K. J. E., Arias-Vasquez, A., Smoller, J. W., Nichols, T. E., Neale, M. C., et al. (2016). Genetic influences on schizophrenia and subcortical brain volumes: large-scale proof of concept. Nat Neurosci 19, 420-431.

40. Friedland-Little, J. M., Hoffmann, A. D., Ocbina, P. J. R., Peterson, M. A., Bosman, J. D., Chen, Y., Cheng, S. Y., Anderson, K. V., and Moskowitz, I. P. (2011). A novel murine allele of Intraflagellar Transport Protein 172 causes a syndrome including VACTERL-like features with hydrocephalus. Hum. Mol. Genet. 20, 3725-3737.

41. Fusar-Poli, P., Smieskova, R., Kempton, M. J., Ho, B. C., Andreasen, N. C., and Borgwardt, S. (2013). Progressive brain changes in schizophrenia related to antipsychotic treatment? A meta-analysis of longitudinal MRI studies. Neurosci. Biobehav. Rev. 37, 1680-1691.

42. Genzen, J. R., Yang, D., Ravid, K., and Bordey, A. (2009). Activation of adenosine A2B receptors enhances ciliary beat frequency in mouse lateral ventricle ependymal cells. Cerebrospinal Fluid Res. 6, 15.

43. Gothelf, D., Frisch, A., Munitz, H., Rockah, R., Laufer, N., Mozes, T., Hermesh, H., Weizman, A., and Frydman, M. (1999). Clinical characteristics of schizophrenia associated with velo-cardio-facial syndrome. Schizophr Res 35, 105-112.

44. Green, T., Gothelf, D., Glaser, B., Debbane, M., Frisch, A., Kotler, M., Weizman, A., and Eliez, S. (2009). Psychiatric disorders and intellectual functioning throughout development in velocardiofacial (22q11.2 deletion) syndrome. J. Am. Acad. Child Adolesc. Psychiatry 48, 1060-1068.

45. Greenstone, M. A., Jones, R. W., Dewar, A., Neville, B. G., and Cole, P. J. (1984). Hydrocephalus and primary ciliary dyskinesia. Arch. Dis. Child. 59, 481-482.

46. Gregory, R I., Yan, K.-P., Amuthan, G., Chendrimada, T., Doratotaj, B., Cooch, N., and Shiekhattar, R. (2004). The Microprocessor complex mediates the genesis of microRNAs. Nature 432, 235-240.

47. Guirao, B., Meunier, A., Mortaud, S., Aguilar, A., Corsi, J. M., Strehl, L., Hirota, Y., Desoeuvre, A., Boutin, C., Han, Y. G., et al. (2010). Coupling between hydrodynamic forces and planar cell polarity orients mammalian motile cilia. Nat Cell Biol 12, 341-350.

48. Ha, S., Lindsay, A. M., Timms, A. E., and Beier, D. R. (2016). Mutations in Dnaafl and Lrrc48 Cause Hydrocephalus, Laterality Defects, and Sinusitis in Mice. G3& #58; Genes|Genomes|Genetics 6, 2479-2487.

49. Haijma, S. V, Van Haren, N., Cahn, W., Koolschijn, P.C.M.P., Hulshoff Pol, H. E., and Kahn, R. S. (2013). Brain volumes in schizophrenia: a meta-analysis in over 18 000 subjects. Schizophr. Bull. 39, 1129-1138.

50. Hirota, Y., Meunier, A., Huang, S., Shimozawa, T., Yamada, O., Kida, Y. S., Inoue, M., Ito, T., Kato, H., Sakaguchi, M., et al. (2010). Planar polarity of multiciliated ependymal cells involves the anterior migration of basal bodies regulated by non-muscle myosin II. Development 137, 3037-3046.

51. Hoglinger, G. U., Rizk, P., Muriel, M. P., Duyckaerts, C., Oertel, W. H., Caille, I., and Hirsch, E. C. (2004). Dopamine depletion impairs precursor cell proliferation in Parkinson disease. Nat Neurosci 7, 726-735.

52. Honea, R., Crow, T. J., Passingham, D., and Mackay, C. E. (2005). Regional deficits in brain volume in schizophrenia: a meta-analysis of voxel-based morphometry studies. Am J Psychiatry 162, 2233-2245.

53. Horga, G., Bernacer, J., Dusi, N., Entis, J., Chu, K., Hazlett, E. A., Haznedar, M. M., Kemether, E., Byne, W., and Buchsbaum, M. S. (2011). Correlations between ventricular enlargement and gray and white matter volumes of cortex, thalamus, striatum, and internal capsule in schizophrenia. Eur. Arch. Psychiatry Clin. Neurosci. 261, 467-476.

54. Howard, S., Landry, C., Fisher, R., Bezouglaia, O., Handley, V., and Campagnoni, A. (1998). Postnatal localization and morphogenesis of cells expressing the dopaminergic D2 receptor gene in rat brain: expression in non-neuronal cells. J Comp Neurol 391, 87-98.

55. Ibañez-Tallon, I., Pagenstecher, A., Fliegauf, M., Olbrich, H., Kispert, A., Ketelsen, U.-P.P., North, A., Heintz, N., Omran, H., Ibanez-Tallon, I., et al. (2004). Dysfunction of axonemal dynein heavy chain Mdnah5 inhibits ependymal flow and reveals a novel mechanism for hydrocephalus formation. Hum. Mol Genet 13, 2133-2141.

56. Jain, A. K., Murty, M. N., and Flynn, P. J. (1999). Data clustering: a review. ACM Comput. Surv. 31, 264-323.

57. Johnstone, E. C., Crow, T. J., Frith, C. D., Husband, J., and Kreel, L. (1976). Cerebral ventricular size and cognitive impairment in chronic schizophrenia. Lancet 2, 924-926.

58. Kahle, K. T., Kulkarni, A. V, Limbrick, D. D., and Warf, B. C. (2016). Hydrocephalus in children. Lancet 387, 788-799.

59. Karayiorgou, M., Simon, T. J., and Gogos, J. A. (2010). 22q11.2 microdeletions: linking DNA structural variation to brain dysfunction and schizophrenia. Nat Rev Neurosci 11, 402-416.

60. Kempton, M. J., Geddes, J. R., Ettinger, U., Williams, S. C. R., and Grasby, P. M. (2008). Meta-analysis, database, and meta-regression of 98 structural imaging studies in bipolar disorder. Arch. Gen. Psychiatry 65, 1017-1032.

61. Kempton, M. J., Stahl, D., Williams, S. C., and DeLisi, L. E. (2010). Progressive lateral ventricular enlargement in schizophrenia: a meta-analysis of longitudinal MRI studies. Schizophr Res 120, 54-62.

62. Konjikusic, M. J., Yeetong, P., Boswell, C. W., Lee, C., Roberson, E. C., Ittiwut, R., Suphapeetiporn, K., Ciruna, B., Gurnett, C. A., Wallingford, J. B., et al. (2018). Mutations in Kinesin family member 6 reveal specific role in ependymal cell ciliogenesis and human neurological development. PLOS Genet. 14, e1007817.

63. Kosaki, K., Ikeda, K., Miyakoshi, K., Ueno, M., Kosaki, R., Takahashi, D., Tanaka, M., Torikata, C., Yoshimura, Y., and Takahashi, T. (2004). Absent inner dynein arms in a fetus with familial hydrocephalus-situs abnormality. Am. J. Med. Genet. 129A, 308-311.

64. Koschtüzke, L., Bertram, J., Hartmann, B., Bartsch, D., Lotze, M., and von Bohlen and Halbach, O. (2015). SrGAP3 knockout mice display enlarged lateral ventricles and specific cilia disturbances of ependymal cells in the third ventricle. Cell Tissue Res. 361, 645-650.

65. Kremen, W. S., Panizzon, M. S., Neale, M C., Fennema-Notestine, C., Prom-Wormley, E., Eyler, L. T., Stevens, A., Franz, C. E., Lyons, M. J., Grant, M. D., et al. (2012). Heritability of brain ventricle volume: converging evidence from inconsistent results. Neurobiol. Aging 33, 1-8.

66. Kuller, L. H., Lopez, O. L., Jagust, W. J., Becker, J. T., DeKosky, S. T., Lyketsos, C., Kawas, C., Breitner, J. C. S., Fitzpatrick, A., and Dulberg, C. (2005). Determinants of vascular dementia in the Cardiovascular Health Cognition Study. Neurology 64, 1548-1552.

67. Kuller, L. H., Lopez, O. L., Becker, J. T., Chang, Y., and Newman, A. B. (2016). Risk of dementia and death in the long-term follow-up of the Pittsburgh Cardiovascular Health Study-Cognition Study. Alzheimer's Dement. 12, 170-183.

68. Lattke, M., Magnutzki, A., Walther, P., Wirth, T., and Baumann, B. (2012). Nuclear Factor B Activation Impairs Ependymal Ciliogenesis and Links Neuroinflammation to Hydrocephalus Formation. J. Neurosci. 32, 11511-11523.

69. Lawrie, S. M., and Abukmeil, S. S. (1998). Brain abnormality in schizophrenia. A systematic and quantitative review of volumetric magnetic resonance imaging studies. Br J Psychiatry 172, 110-120.

70. Lechtreck, K.-F., Delmotte, P., Robinson, M. L., Sanderson, M. J., and Witman, G. B. (2008). Mutations in Hydin impair ciliary motility in mice. J. Cell Biol. 180, 633-643.

71. Lee, L. (2013). Riding the wave of ependymal cilia: genetic susceptibility to hydrocephalus in primary ciliary dyskinesia. J Neurosci Res 91, 1117-1132.

72. Lee, L., Campagna, D. R., Pinkus, J. L., Mulhern, H., Wyatt, T. A., Sisson, J. H., Pavlik, J. A., Pinkus, G. S., and Fleming, M. D. (2008). Primary Ciliary Dyskinesia in Mice Lacking the Novel Ciliary Protein Pcdpl. Mol. Cell. Biol. 28, 949-957.

73. Lindsay, E. A., Botta, A., Jurecic, V., Carattini-Rivera, S., Cheah, Y. C., Rosenblatt, H. M., Bradley, A., and Baldini, A. (1999). Congenital heart disease in mice deficient for the DiGeorge syndrome region. Nature 401, 379-383.

74. Long, X., Liao, W., Jiang, C., Liang, D., Qiu, B., and Zhang, L. (2012). Healthy Aging. Acad. Radiol. 19, 785-793.

75. Lowe, D. G., and G., D. (2004). Distinctive Image Features from Scale-Invariant Keypoints. Int. J. Comput. Vis. 60, 91-110.

76. Machado, A. M., Simon, T. J., Nguyen, V., McDonald-McGinn, D. M., Zackai, E. H., and Gee, J. C. (2007). Corpus callosum morphology and ventricular size in chromosome 22q11.2 deletion syndrome. Brain Res 1131, 197-210.

77. Madisen, L., Zwingman, T. A., Sunkin, S. M., Oh, S. W., Zariwala, H. A., Gu, H., Ng, L. L., Palmiter, R D., Hawrylycz, M. J., Jones, A. R., et al. (2010). A robust and high-throughput Cre reporting and characterization system for the whole mouse brain. Nat. Neurosci 13, 133-140.

78. Mak, E., Su, L., Williams, G. B., Firbank, M. J., Lawson, R. A., Yarnall, A. J., Duncan, G. W., Mollenhauer, B., Owen, A. M., Khoo, T. K., et al. (2017). Longitudinal whole-brain atrophy and ventricular enlargement in non-demented Parkinson's disease. Neurobiol. Aging 55, 78-90.

79. Mata, I., Perez-Iglesias, R., Roiz-Santiañez, R., Tordesillas-Gutierrez, D., Gonzalez-Mandly, A., Vazquez-Barquero, J. L., and Crespo-Facorro, B. (2009). A Neuregulin 1 Variant Is Associated with Increased Lateral Ventricle Volume in Patients with First-Episode Schizophrenia. Biol. Psychiatry 65, 535-540.

80. Matsuo, M., Shimada, A., Koshida, S., Saga, Y., and Takeda, H. (2013). The establishment of rotational polarity in the airway and ependymal cilia: analysis with a novel cilium motility mutant mouse. Am J Physiol Lung Cell Mol Physiol 304, L736-L745.

81. McKenzie, C. W., Craige, B., Kroeger, T. V., Finn, R., Wyatt, T. A., Sisson, J. H., Pavlik, J. A., Strittmatter, L., Hendricks, G. M., Witman, G. B., et al. (2015). CFAP54 is required for proper ciliary motility and assembly of the central pair apparatus in mice. Mol. Biol. Cell 26, 3140-3149.

82. Michaloudi, H. C., and Papadopoulos, G. C. (1996). Catecholaminergic and serotoninergic fibres innervate the ventricular system of the hedgehog CNS. J Anat 189 (Pt 2, 273-283.

83. Mirzadeh, Z., Han, Y. G., Soriano-Navarro, M., Garcia-Verdugo, J. M., and Alvarez-Buylla, A. (2010a). Cilia organize ependymal planar polarity. J Neurosci 30, 2600-2610.

84. Mirzadeh, Z., Doetsch, F., Sawamoto, K., Wichterle, H., and Alvarez-Buylla, A. (2010b). The Subventricular Zone En-face: Wholemount Staining and Ependymal Flow. J. Vis. Exp 1938.

85. Miyan, J. A., Nabiyouni, M., and Zendah, M. (2003). Development of the brain: a vital role for cerebrospinal fluid. Can J Physiol Pharmacol 81, 317-328.

86. Mueser, K. T., and McGurk, S. R. (2004). Schizophrenia. Lancet 363, 2063-2072.

87. Murphy, K. C. (2002). Schizophrenia and velo-cardio-facial syndrome. Lancet 359, 426-430.

88. Murphy, K. C., Jones, L. A., and Owen, M. J. (1999). High rates of schizophrenia in adults with velo-cardio-facial syndrome. Arch Gen Psychiatry 56, 940-945.

89. Narr, K. L., Thompson, P. M., Szeszko, P., Robinson, D., Jang, S., Woods, R. P., Kim, S., Hayashi, K. M., Asunction, D., Toga, A. W., et al. (2004). Regional specificity of hippocampal volume reductions in first-episode schizophrenia. Neuroimage. 21, 1563-1575.

90. Nestor, S. M., Rupsingh, R., Borne, M., Smith, M., Accomazzi, V., Wells, J. L., Fogarty, J., Bartha, R., and Alzheimer's Disease Neuroimaging Initiative (2008). Ventricular enlargement as a possible measure of Alzheimer's disease progression validated using the Alzheimer's disease neuroimaging initiative database. Brain 131, 2443-2454.

91. Nguyen, T., Chin, W. C., O'Brien, J. A., Verdugo, P., and Berger, A. J. (2001). Intracellular pathways regulating ciliary beating of rat brain ependymal cells. J. Physiol. 531, 131-140.

92. Ohata, S., Nakatani, J., Herranz-Perez, V., Cheng, J., Belinson, H., Inubushi, T., Snider, W. D., Garcia-Verdugo, J. M., Wynshaw-Boris, A., and Alvarez-Buylla, A. (2014). Loss of Dishevelleds disrupts planar polarity in ependymal motile cilia and results in hydrocephalus. Neuron 83, 558-571. 93. Olabi, B., Ellison-Wright, I., McIntosh, A. M., Wood, S. J., Bullmore, E., and Lawrie, S. M. (2011). Are there progressive brain changes in schizophrenia? A meta-analysis of structural magnetic resonance imaging studies. Biol. Psychiatry 70, 88-96.

94. Pfefferbaum, A., Sullivan, E. V, and Carmelli, D. (2004). Morphological changes in aging brain structures are differentially affected by time-linked environmental influences despite strong genetic stability. Neurobiol. Aging 25, 175-183.

95. Picco, P., Leveratto, L., Cama, A., Vigliarolo, M. A., Levato, G. L., Gattorno, M., Zammarchi, E., and Donati, M. A. (1993). Immotile cilia syndrome associated with hydrocephalus and precocious puberty: a case report. Eur. J. Pediatr. Surg. 3 Suppl 1, 20-21.

96. Piskorowski, R. A., Nasrallah, K., Diamantopoulou, A., Mukai, J., Hassan, S. I., Siegelbaum, S. A., Gogos, J. A., and Chevaleyre, V. (2016). Age-dependent specific changes in area CA2 of the hippocampus and social memory deficit in a mouse model of the 22q11.2 deletion syndrome. Neuron 89, 163-176.

97. Praveen, K., Davis, E. E., and Katsanis, N. (2015). Unique among ciliopathies: primary ciliary dyskinesia, a motile cilia disorder. F1000Prime Rep. 7, 36.

98. Pulver, A. E., Nestadt, G., Goldberg, R., Shprintzen, R. J., Lamacz, M., Wolyniec, P. S., Morrow, B., Karayiorgou, M., Antonarakis, S. E., Housman, D., et al. (1994). Psychotic illness in patients diagnosed with velo-cardio-facial syndrome and their relatives. J Nery Ment Dis 182, 476-478.

99. Salathe, M. (2007). Regulation of Mammalian Ciliary Beating. Annu. Rev. Physiol. 69, 401-422.

100. De Santi, M. M., Magni, A., Valletta, E. A., Gardi, C., and Lungarella, G. (1990). Hydrocephalus, bronchiectasis, and ciliary aplasia. Arch. Dis. Child. 65, 543-544.

101. Satir, P., and Christensen, S. T. (2007). Overview of Structure and Function of Mammalian Cilia. Annu. Rev. Physiol. 69, 377-400.

102. Schmid, A., Sutto, Z., Nlend, M.-C., Horvath, G., Schmid, N., Buck, J., Levin, L. R., Conner, G. E., Fregien, N., and Salathe, M. (2007). Soluble adenylyl cyclase is localized to cilia and contributes to ciliary beat frequency regulation via production of cAMP. J. Gen. Physiol. 130, 99-109.

103. Schneider, M., Debbane, M., Bassett, A. S., Chow, E. W., Fung, W. L., van den Bree, M., Owen, M., Murphy, K. C., Niarchou, M., Kates, W. R., et al. (2014). Psychiatric disorders from childhood to adulthood in 22q11.2 deletion syndrome: results from the International Consortium on Brain and Behavior in 22q11.2 Deletion Syndrome. Am. J. Psychiatry 171, 627-639.

104. Shenton, M. E., Dickey, C. C., Frumin, M., and McCarley, R. W. (2001). A review of MRI findings in schizophrenia. Schizophr Res 49, 1-52.

105. Shprintzen, R. J., Goldberg, R., Golding-Kushner, K. J., and Marion, R. W. (1992). Late-onset psychosis in the velo-cardio-facial syndrome. Am J Med Genet 42, 141-142.

106. Simon, T. J., Ding, L., Bish, J. P., McDonald-McGinn, D. M., Zackai, E. H., and Gee, J. (2005). Volumetric, connective, and morphologic changes in the brains of children with chromosome 22q11.2 deletion syndrome: an integrative study. Neuroimage 25, 169-180.

107. Small, E. M., and Olson, E. N. (2011). Pervasive roles of microRNAs in cardiovascular biology. Nature 469, 336-342.

108. Stark, K. L., Xu, B., Bagchi, A., Lai, W. S., Liu, H., Hsu, R., Wan, X., Pavlidis, P., Mills, A. A., Karayiorgou, M., et al. (2008). Altered brain microRNA biogenesis contributes to phenotypic deficits in a 22q11-deletion mouse model. Nat Genet 40, 751-760.

109. Steen, R. G., Mull, C., McClure, R., Hamer, R. M., and Lieberman, J. A. (2006). Brain volume in first-episode schizophrenia: systematic review and meta-analysis of magnetic resonance imaging studies. Br J Psychiatry 188, 510-518.

110. Styner, M., Lieberman, J. A., McClure, R. K., Weinberger, D. R., Jones, D. W., and Gerig, G. (2005). Morphometric analysis of lateral ventricles in schizophrenia and healthy controls regarding genetic and disease-specific factors. Proc Natl Acad Sci USA 102, 4872-4877.

111. Swiderski, R. E., Agassandian, K., Ross, J. L., Bugge, K., Cassell, M. D., and Yeaman, C. (2012). Structural defects in cilia of the choroid plexus, subfornical organ and ventricular ependyma are associated with ventriculomegaly. Fluids Barriers CNS 9, 22.

112. Sztriha, L., Guerrini, R., Harding, B., Stewart, F., Chelloug, N., and Johansen, J. G. (2004). Clinical, MRI, and pathological features of polymicrogyria in chromosome 22q11 deletion syndrome. Am J Med Genet A 127A, 313-317.

113. Tissir, F., and Goffinet, A. M. (2013). Shaping the nervous system: role of the core planar cell polarity genes. Nat Rev Neurosci 14, 525-535.

114. Tissir, F., Qu, Y., Montcouquiol, M., Zhou, L., Komatsu, K., Shi, D., Fujimori, T., Labeau, J., Tyteca, D., Courtoy, P., et al. (2010). Lack of cadherins Celsr2 and Celsr3 impairs ependymal ciliogenesis, leading to fatal hydrocephalus. Nat Neurosci 13, 700-707.

115. Todd, K. L., Brighton, T., Norton, E. S., Schick, S., Elkins, W., Pletnikova, O., Fortinsky, R. H., Troncoso, J. C., Molfese, P. J., Resnick, S. M., et al. (2018). Ventricular and Periventricular Anomalies in the Aging and Cognitively Impaired Brain. Front. Aging Neurosci. 9, 445.

116. Tome, M., Moreira, E., Perez-Figares, J. M., and Jimenez, A. J. (2007). Presence of D1- and D2-like dopamine receptors in the rat, mouse and bovine multiciliated ependyma. J Neural Transm 114, 983-994.

117. Vieira, J. P., Lopes, P., and Silva, R. (2012). Primary Ciliary Dyskinesia and Hydrocephalus With Aqueductal Stenosis. J. Child Neurol. 27, 938-941.

118. Vita, A., De, P. L., Silenzi, C., Dieci, M., De Peri, L., Silenzi, C., and Dieci, M. (2006). Brain morphology in first-episode schizophrenia: a meta-analysis of quantitative magnetic resonance imaging studies. Schizophr Res 82, 75-88.

119. Vogel, P., Read, R. W., Hansen, G. M., Payne, B. J., Small, D., Sands, A. T., and Zambrowicz, B. P. (2012). Congenital hydrocephalus in genetically engineered mice. Vet Pathol 49, 166-181.

120. Wallingford, J. B. (2010). Planar cell polarity signaling, cilia and polarized ciliary beating. Curr Opin Cell Biol 22, 597-604.

121. Wang, X., Merzenich, M. M., Beitel, R., and Schreiner, C. E. (1995). Representation of a species-specific vocalization in the primary auditory cortex of the common marmoset: temporal and spectral characteristics. J. Neurophysiol. 74, 2685-2706.

122. Wang, X., Zhou, Y., Wang, J., Tseng, I.-C., Huang, T., Zhao, Y., Zheng, Q., Gao, Y., Luo, H., Zhang, X., et al. (2016). SNX27 Deletion Causes Hydrocephalus by Impairing Ependymal Cell Differentiation and Ciliogenesis. J. Neurosci. 36, 12586-12597.

123. Wang, Y., Medvid, R., Melton, C., Jaenisch, R., and Blelloch, R. (2007). DGCR8 is essential for microRNA biogenesis and silencing of embryonic stem cell self-renewal. Nat Genet 39, 380-385.

124. Wessels, M. W., den Hollander, N. S., and Willems, P. J. (2003). Mild fetal cerebral ventriculomegaly as a prenatal sonographic marker for Kartagener syndrome. Prenat. Diagn. 23, 239-242.

125. Wilson, G. R., Wang, H. X., Egan, G. F., Robinson, P. J., Delatycki, M. B., O'Bryan, M. K., and Lockhart, P. J. (2010). Deletion of the Parkin co-regulated gene causes defects in ependymal ciliary motility and hydrocephalus in the quakingviable mutant mouse. Hum. Mol. Genet. 19, 1593-1602.

126. Wodarczyk, C., Rowe, I., Chiaravalli, M., Pema, M., Qian, F., and Boletta, A. (2009). A Novel Mouse Model Reveals that Polycystin-1 Deficiency in Ependyma and Choroid Plexus Results in Dysfunctional Cilia and Hydrocephalus. PLoS One 4, e7137.

127. Wright, I. C., Rabe-Hesketh, S., Woodruff, P. W., David, A. S., Murray, R. M., and Bullmore, E. T. (2000). Meta-analysis of regional brain volumes in schizophrenia. Am J Psychiatry 157, 16-25.

128. Yamazaki, Y., Hirai, Y., Miyake, K., and Shimada, T. (2014). Targeted gene transfer into ependymal cells through intraventricular injection of AAV1 vector and long-term enzyme replacement via the CSF. Sci. Rep. 4, 5506.

129. Zhang, Y., Huang, G., Shornick, L. P., Roswit, W. T., Shipley, J. M., Brody, S. L., and Holtzman, M. J. (2007). A transgenic FOXJ1-Cre system for gene inactivation in ciliated epithelial cells. Am. J Respir. Cell Mol Biol 36, 515-519.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

LIST OF SEQUENCES

| SEQ ID NO: | Type | Source | Sequence | Description |
|---|---|---|---|---|
| 1 | RNA | Human | AAUCAUUCACGGACAACACUU | Human hsa-miR-382-3p (mature miRNA) |
| 2 | RNA | Mouse | UCAUUCACGGACAACACUUUUU | Mouse mmu-miR-382-3p (mature miRNA) |
| 3 | RNA | Mouse | CACAGCUCCCAUCUCAGAACAA | Mouse mmu-miR-674-3p (mature miRNA) |
| 4 | RNA | Human | UACUUGAAGAGAAGUUGUUCGUGGUGGAUUCG CUUUACUUAUGACGAAUCAUUCACGGACAACA CUUUUUUUCAGUA | Human mir-382 gene |
| 5 | RNA | Mouse | UACUUGAAGAGAAGUUGUUCGUGGUGGAUUCG CUUUACUUGUGACGAAUCAUUCACGGACAACA CUUUUUUUCAGUA | Mouse mir-382 gene |
| 6 | RNA | Mouse | GGCCUAGUCAUCACCCUGAGCCUUGCACUGAG AUGGGAGUGGUGUAAGGCUCAGGUAUGCACAG CUCCCAUCUCAGAACAAGGCUCGGGUGUGCUC AGCU | Mouse mir-674 gene |

| SEQ ID NO: | Type | Source | Sequence | Description |
|---|---|---|---|---|
| 7 | DNA | Artificial sequence | TTTGTGACGTTGCAGCT | mmu-miR-153-5p forward primer |
| 8 | DNA | Artificial sequence | TCATTCACGGACAACACTTTTT | mmu-miR-382-3p forward primer |
| 9 | DNA | Artificial sequence | CACAGCTCCCATCTCAGAACAA | mmu-miR-674-3p forward primer |
| 10 | DNA | Artificial sequence | ATGGCTCCTAACACTTCTACCA | Drd1 forward |
| 11 | DNA | Artificial sequence | GGGTATTCCCTAAGAGAGTGGAC | Drd1 reverse |
| 12 | DNA | Artificial sequence | CCACGACCATCCTCAGACATTG | Dgcr8 forward |
| 13 | DNA | Artificial sequence | ATGAAAATCTCCCCTCCCCACAGCC | Dgcr8 reverse |
| 14 | DNA | Artificial sequence | CGCTTCGGCAGCACATATAC | U6 snRNA forward |
| 15 | DNA | Artificial sequence | TTCACGAATTTGCGTGTCAT | U6 snRNA reverse |
| 16 | DNA | Artificial sequence | GTACAGCTGTTGACAGTGAGCGACTTTGTGACG TTGCAGCTTGTGAA | miR-153-5p-1 primer |
| 17 | DNA | Artificial sequence | CCATCTGTGGCTTCACAAGCTGCAACGTCACAA AGTCGCTCACTGTCAACAGCT | miR-153-5p-2 primer |
| 18 | DNA | Artificial sequence | GCCACAGATGGAGCTGCAACGTCACAAAGCTGC CTACTGCCTCGGAA | miR-153-5p-3 primer |
| 19 | DNA | Artificial sequence | AGCTTTCCGAGGCAGTAGGCAGCTTTGTGACGT TGCAGCT | miR-153-5p-4 primer |
| 20 | DNA | Artificial sequence | GTACAGCTGTTGACAGTGAGCGACTCATTCACG GACAACACTTTTTGTGAA | miR-382-3p-1 primer |
| 21 | DNA | Artificial sequence | CCATCTGTGGCTTCACAAAAAAGTGTTGTCCGT GAATGAGTCGCTCACTGTCAACAGCT | miR-382-3p-2 primer |
| 22 | DNA | Artificial sequence | GCCACAGATGGAAAAGTGTTGTCCGTGAATGA GCTGCCTACTGCCTCGGAA | miR-382-3p-3 primer |
| 23 | DNA | Artificial sequence | AGCTTTCCGAGGCAGTAGGCAGCTCATTCACGG ACAACACTTTTT | miR-382-3p-4 primer |
| 24 | DNA | Artificial sequence | GTACAGCTGTTGACAGTGAGCGACCACAGCTCC CATCTCAGAACAATGTGAA | miR-674-3p-1 primer |
| 25 | DNA | Artificial sequence | CCATCTGTGGCTTCACATTGTTCTGAGATGGGAG CTGTGGTCGCTCACTGTCAACAGCT | miR-674-3p-2 primer |
| 26 | DNA | Artificial sequence | GCCACAGATGGTTGTTCTGAGATGGGAGCTGTG GCTGCCTACTGCCTCGGAA | miR-674-3p-3 primer |
| 27 | DNA | Artificial sequence | AGCTTTCCGAGGCAGTAGGCAGCCACAGCTCCC ATCTCAGAACAA | miR-674-3p-4 primer |
| 28 | DNA | Artificial sequence | TTGTTCTGAGATGGGAGCTGTG | miR-382-3p sponge |
| 29 | DNA | Artificial sequence | TCATTCACGGACAACACTTTT | miR-674-3p sponge |
| 30 | DNA | Artificial sequence | GACACTGTGAGCGAAGACATA | scrambled control |

-continued

| LIST OF SEQUENCES | | | | |
|---|---|---|---|---|
| SEQ ID NO: | Type | Source | Sequence | Description |
| 31 | DNA | Artificial sequence | TAATGAGCTGTGCCTCATCG A | mDrd1Δ7bp.sgRN A |
| 32 | DNA | Artificial sequence | AGTATCCTCTCTTAAAAAAAAAAAAAAAGCTC TTTAATGTTAGTGGTAAACTAGCTAATGCCTCAT CGTGGAAGTATACACTTCTGTTGTTGGTGGGGG GAATAGAAGAACCCCTTCCC | mDrd1Δ7bp.donor |
| 33 | DNA | Artificial sequence | CACTCTTTCCCTACACGACGCTCTTCCGATCTagtc acaggtcacagcagcccctcc | mDrd1Δ7bp.NGS.F |
| 34 | DNA | Artificial sequence | GTGACTGGAGTTCAGACGTGTGCTCTTCCGATCT actgttgcaatacccccacccgagg | mDrd1Δ7bp.NGS.R |
| 35 | DNA | Artificial sequence | CAGGATTAAGATGTGCATCG | mDrd1Δ13bp.sgRNA |
| 36 | DNA | Artificial sequence | TGCTTGAAATGGCTTTCTGAAACAAACAAATGA CTGTCCAGGATTAAGATGTGCATCGAGAAAGTC ACAGGTCACAGCAGCCCCTCCGATAGTTGGGCT CATCGCTGGTTCTTCATCTGC | mDrd1Δ13bp.donor |
| 37 | DNA | Artificial sequence | CACTCTTTCCCTACACGACGCTCTTCCGATCTatgg cagaggctttcccccgaggcaa | mDrd1Δ13bp.NGS.F |
| 38 | DNA | Artificial sequence | GTGACTGGAGTTCAGACGTGTGCTCTTCCGATCT acaaaagtagcccccttgagcagccg | mDrd1Δ13bp.NGS.R |
| 39 | DNA | Artificial sequence | TGGTAAACTAGCTAATGAGCTGTGCCTCATCGT GGAAGTA | Drd1 region 1 |
| 40 | DNA | Artificial sequence | TGGTAAACTAGCTAATG------- CCTCATCGTGGAAGTA | Drd1Δ7bp |
| 41 | DNA | Artificial sequence | GATGTGCATCGAGGTGAATGAGCTGTAAAGTCA CAGGTCA | Drd1 region 2 |
| 42 | DNA | Artificial sequence | GATGTGCATCGAG------------- AAAGTCACAGGTCA | Drd1Δ13bp |

What is claimed is:

1. A method for decreasing ventricular enlargement in a subject in need thereof, said method comprising administering to the subject a therapeutically effective amount of (i) miR-382-3p and/or miR-674-3p, or (ii) a vector expressing miR-382-3p and/or miR-674-3p.

2. The method of claim 1, wherein the ventricular enlargement is associated with a schizophrenia (SCZ), 22q11 deletion syndrome (22q11DS), Alzheimer's disease, Parkinson's disease, vascular dementia, age-dependent ventriculomegaly, spontaneous ventriculomegaly, hydrocephalus, primary ciliary dyskinesia, or normal aging.

3. The method of claim 1, wherein miR-382-3p comprises the sequence AAUCAUUCACGGACAACACUU (SEQ ID NO: 1) or UCAUUCACGGACAACACUUUUU (SEQ ID NO: 2).

4. The method of claim 3, wherein miR-382-3p consists of the sequence AAUCAUUCACGGACAACACUU (SEQ ID NO: 1) or UCAUUCACGGACAACACUUUUU (SEQ ID NO: 2).

5. The method of claim 1, wherein the miR-674-3p comprises the sequence CACAGCUCCCAU-CUCAGAACAA (SEQ ID NO: 3).

6. The method of claim 5, wherein miR-674-3p consists of the sequence CACAGCUCCCAUCUCAGAACAA (SEQ ID NO: 3).

7. The method of claim 1, wherein the administration is inside the ventricles of the subject.

8. The method of claim 7, wherein the administration is by intracerebroventricular injection.

9. The method of claim 1, wherein the administration results in a decrease in ventricular enlargement, an increase in ciliary beating on ependymal cells lining the walls of lateral ventricles (LVs) of the subject, a decrease of dopamine receptor (Drd1) expression and/or function in ependymal cells lining the walls of ventricles of the subject, and/or an increase in the level of miR-382-3p and/or miR-674-3p in ependymal cells lining the walls of ventricles of the subject.

10. The method of claim 9, wherein the administration results in a decrease in ventricular enlargement of one or more of the brain lateral ventricles (LVs) and/or third ventricle (TV) of the subject.

11. The method of claim 1, wherein the subject has an increased size of one or more brain ventricles, a decreased ciliary beating on ependymal cells lining the walls of lateral ventricles (LVs), an increased dopamine receptor (Drd1) expression and/or function in ependymal cells lining the walls of ventricles, and/or a decreased level of miR-382-3p and/or miR-674-3p in ependymal cells lining the walls of ventricles as compared to a control.

12. The method of claim 11, wherein the brain ventricles are lateral ventricles (LVs) and/or third ventricle (TV).

13. The method of claim 11, wherein the control is a predetermined standard, or the value in a healthy age- and gender-matched subject, or an average value for several such subjects.

14. The method of claim 1, wherein the vector is selected from adeno-associated virus (AAV) vectors, lentivirus vectors, adenoviral vector, retroviral vectors, alphaviral vectors, vaccinia virus vectors, herpes simplex virus (HSV) vectors, rabies virus vectors, and Sindbis virus vectors.

15. The method of claim 1, further comprising administering to the subject an additional treatment agent.

16. The method of claim 15, wherein the additional treatment agent is an antipsychotic.

17. The method of claim 1, wherein the ventricular enlargement is caused by decreased ciliary beating on ependymal cells.

\* \* \* \* \*

SEQUENCE LISTING

<160> NUMBER OF SEQ ID NOS: 47

<210> SEQ ID NO 1
<211> LENGTH: 21
<212> TYPE: RNA
<213> ORGANISM: Homo sapiens

<400> SEQUENCE: 1
aaucauucac ggacaacacu u                                        21

<210> SEQ ID NO 2
<211> LENGTH: 22
<212> TYPE: RNA
<213> ORGANISM: Mus musculus

<400> SEQUENCE: 2
ucauucacgg acaacacuuu uu                                       22

<210> SEQ ID NO 3
<211> LENGTH: 22
<212> TYPE: RNA
<213> ORGANISM: Mus musculus

```
<400> SEQUENCE: 3
cacagcuccc aucucagaac aa                                              22

<210> SEQ ID NO 4
<211> LENGTH: 76
<212> TYPE: RNA
<213> ORGANISM: Homo sapiens

<400> SEQUENCE: 4
uacuugaaga gaaguuguuc gugguggauu cgcuuuacuu augacgaauc auucacggac    60
aacacuuuuu ucagua                                                    76

<210> SEQ ID NO 5
<211> LENGTH: 76
<212> TYPE: RNA
<213> ORGANISM: Mus musculus

<400> SEQUENCE: 5
uacuugaaga gaaguuguuc gugguggauu cgcuuuacuu gugacgaauc auucacggac    60
aacacuuuuu ucagua                                                    76

<210> SEQ ID NO 6
<211> LENGTH: 100
<212> TYPE: RNA
<213> ORGANISM: Mus musculus

<400> SEQUENCE: 6
ggccuaguca ucacccugag ccuugcacug agaugggagu gguguaaggc ucagguaugc    60
acagcuccca ucucagaaca aggcucgggu gugcucagcu                          100

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttgtgacgt tgcagct                                                   17

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcattcacgg acaacacttt tt                                             22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacagctccc atctcagaac aa                                             22
```

```
<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggctccta acacttctac ca                                              22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggtattccc taagagagtg gac                                             23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccacgaccat cctcagacat tg                                              22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgaaaatct cccctcccca cagcc                                           25

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgcttcggca gcacatatac                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttcacgaatt tgcgtgtcat                                                 20
```

```
<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtacagctgt tgacagtgag cgactttgtg acgttgcagc ttgtgaa                     47

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccatctgtgg cttcacaagc tgcaacgtca caaagtcgct cactgtcaac agct            54

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccacagatg gagctgcaac gtcacaaagc tgcctactgc ctcggaa                     47

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agctttccga ggcagtaggc agctttgtga cgttgcagct                             40

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtacagctgt tgacagtgag cgactcattc acggacaaca cttttttgtg aa              52

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccatctgtgg cttcacaaaa aagtgttgtc cgtgaatgag tcgctcactg tcaacagct       59

<210> SEQ ID NO 22
```

```
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gccacagatg gaaaaagtgt tgtccgtgaa tgagctgcct actgcctcgg aa           52

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agctttccga ggcagtaggc agctcattca cggacaacac ttttt              45

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtacagctgt tgacagtgag cgaccacagc tcccatctca gaacaatgtg aa           52

<210> SEQ ID NO 25
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccatctgtgg cttcacattg ttctgagatg ggagctgtgg tcgctcactg tcaacagct      59

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccacagatg gttgttctga gatgggagct gtggctgcct actgcctcgg aa           52

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agctttccga ggcagtaggc agccacagct cccatctcag aacaa              45

<210> SEQ ID NO 28
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttgttctgag atgggagctg tg                                            22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcattcacgg acaacacttt t                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gacactgtga gcgaagacat a                                             21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taatgagctg tgcctcatcg                                               20

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
agtatcctct cttaaaaaaa aaaaaaaaag ctctttaatg ttagtggtaa actagctaat     60
gcctcatcgt ggaagtatac acttctgttg ttggtggggg gaatagaaga accccttccc    120

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cactctttcc ctacacgacg ctcttccgat ctagtcacag gtcacagcag cccctcc        57

<210> SEQ ID NO 34
```

```
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgactggag ttcagacgtg tgctcttccg atctactgtt gcaataccccc cacccgagg      59

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caggattaag atgtgcatcg                                                  20

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
tgcttgaaat ggctttctga aacaaacaaa tgactgtcca ggattaagat gtgcatcgag      60
aaagtcacag gtcacagcag cccctccgat agttgggctc atcgctggtt cttcatctgc     120

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cactctttcc ctacacgacg ctcttccgat ctatggcaga ggctttcccc gaggcaa        57

<210> SEQ ID NO 38
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtgactggag ttcagacgtg tgctcttccg atctacaaaa gtagcccctt gagcagccg       59

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tggtaaacta gctaatgagc tgtgcctcat cgtggaagta                            40
```

-continued

```
<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tggtaaacta gctaatgcct catcgtggaa gta                              33

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gatgtgcatc gaggtgaatg agctgtaaag tcacaggtca                       40

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gatgtgcatc gagaaagtca caggtca                                     27

<210> SEQ ID NO 43
<211> LENGTH: 23
<212> TYPE: RNA
<213> ORGANISM: Mus musculus

<400> SEQUENCE: 43
ugcaucgagg ugaaugagcu gua                                         23

<210> SEQ ID NO 44
<211> LENGTH: 25
<212> TYPE: RNA
<213> ORGANISM: Mus musculus

<400> SEQUENCE: 44
gguaaacuag cuaaugagcu gugcc                                       25

<210> SEQ ID NO 45
<211> LENGTH: 22
<212> TYPE: RNA
<213> ORGANISM: Mus musculus

<400> SEQUENCE: 45
cacaccuccc aucucagaac aa                                          22

<210> SEQ ID NO 46
<211> LENGTH: 46
<212> TYPE: DNA
<213> ORGANISM: Mus musculus

<400> SEQUENCE: 46
taagatgtgc atcgaggtga atgagctgta aagtcacagg tcacag                46
```

-continued

```
<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taagatgtgc atcgagaaag tcacaggtca cag                                    33
```